United States Patent [19]

Sadaki et al.

[11] Patent Number: 4,717,767

[45] Date of Patent: Jan. 5, 1988

[54] 7-AMINO-3-(PYRAZINYLMETHYL) OR (PYRIDAZINYLMETHYL)-CEPHALOSPORINS

[75] Inventors: Hiroshi Sadaki; Hiroyuki Imaizumi; Takashi Nagai; Kenji Takeda; Isao Myokan, all of Toyama; Takihiro Inaba, Namerikawa; Yasuo Watanabe, Toyama; Yoshikazu Fukuoka, Toyama; Shinzaburo Minami, Toyama; Isamu Saikawa, Toyama, all of Japan

[73] Assignee: Toyama Chemical Co., Ltd., Tokyo, Japan

[21] Appl. No.: 860,317

[22] Filed: Jul. 22, 1986

Related U.S. Application Data

[62] Division of Ser. No. 552,468, Nov. 16, 1983, Pat. No. 4,618,606.

[30] Foreign Application Priority Data

| | | | |
|---|---|---|---|
| Nov. 17, 1982 | [JP] | Japan | 57-200382 |
| Apr. 19, 1983 | [JP] | Japan | 58-67871 |

[51] Int. Cl.⁴ .......... C07D 501/18

[52] U.S. Cl. .......... 540/222

[58] Field of Search .......... 540/222, 221

[56] References Cited

U.S. PATENT DOCUMENTS

| | | | |
|---|---|---|---|
| 4,423,213 | 12/1983 | Takaya et al. | 540/222 |
| 4,431,803 | 2/1984 | Kukalja et al. | 540/222 |
| 4,489,072 | 12/1984 | Sadaki et al. . | |
| 4,614,819 | 9/1986 | Nagai et al. | 540/222 |

FOREIGN PATENT DOCUMENTS 3137854 4/1982 Fed. Rep. of Germany .

OTHER PUBLICATIONS

Takeda, Derwent Abstract, 65150.

*Primary Examiner*—Donald G. Daus
*Assistant Examiner*—Barbara Cassatt
*Attorney, Agent, or Firm*—Oblon, Fisher, Spivak, McClelland, & Maier

[57] ABSTRACT

This invention relates to a 7-amino-3-(pyrazinylmethyl)- or (pyridazinylmethyl)-cephalosporins of the formula:

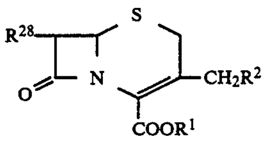

wherein $R^1$ represents a hydrogen atom or a carboxyl-protecting group; $R^2$ represents a group of the formula:

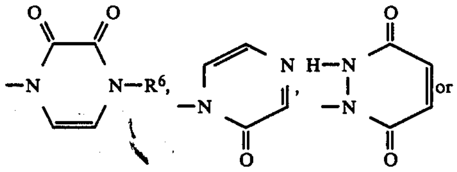

or

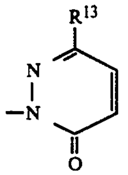

in which $R^6$ represents a hydrogen atom, a $C_{1-5}$alkyl group or a di-$C_{1-5}$alkylamino group; $R^{13}$ represents a $C_{1-5}$alkyl group; and $R^{28}$ represents an amino group.

6 Claims, No Drawings

7-AMINO-3-(PYRAZINYLMETHYL) OR (PYRIDAZINYLMETHYL)-CEPHALOSPORINS

This is a division of application Ser. No. 552, 468, filed Nov. 16, 1983, now U.S. Pat. No. 4,618,606.

This invention relates to novel cephalosporins, processes for producing said cephalosporins, an antibacterial agent containing said cephalosporins, intermediates for the production of said cephalosporins and a process for producing said intermediates.

The present inventors have conducted studies with the aim of discovering compounds having a broad antibacterial spectrum, exhibiting an excellent antibacterial activity against gram-positive and gram-negative bacteria, being stable to β-lactamase produced by bacteria, having a low toxicity, being at the same time well absorbable upon oral or parenteral administration and having an excellent therapeutic effect on the diseases of human beings and animals. As a result, it has been found that novel cephalosporins characterized in that a substituted or unsubstituted 2,3-dioxo-1,2,3,4-tetrahydropyrazinyl, 2-oxo-1,2-dihydropyrazinyl, 3,6-dioxo-1,2,3,6-tetrahydropyradazinyl or 6-oxo-1,6-dihydropyridazinyl group is attached to the exomethylene group at the 3-position of the cephem ring through a carbon-nitrogen bond and the following group is attached to the amino group at the 7-position, have the above-mentioned excellent properties:

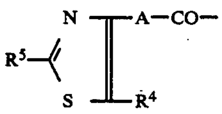

wherein A, $R^4$ and $R^5$ are as defined below.

It is an object of this invention to provide novel cephalosporins having the above-mentioned chemical structural characteristic features, having a broad antibacterial spectrum, being stable against β-lactamase produced by bacteria, having a low toxicity, being well absorbed upon oral or parenteral administration, and having an excellent therapeutic effect on the diseases of human beings and animals.

It is another object of this invention to provide a process for producing said novel cephalosporins.

It is a further object of this invention to provide an antibacterial agent containing said cephalosporins.

It is a still further object of this invention to provide intermediates for the production of said novel cephalosporins and to provide a process for producing said intermediates.

Other objects and advantages of this invention will become apparent from the following description.

According to this invention, there is provided a novel cephalosporin, particularly a cephalosporin represented by the following formula, or a salt thereof:

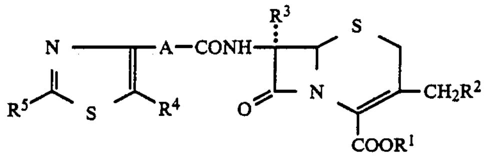

[I]

wherein $R^1$ represents a hydrogen atom or a carboxyl-protecting group; $R^2$ represents a group of the formula,

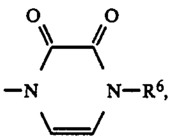

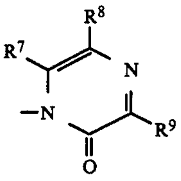

,

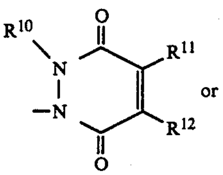

or

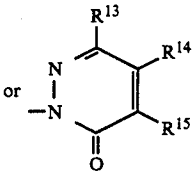

in which $R^6$ represents a hydrogen atom, a hydroxyl group, a nitro group, a carbamoyl group, a thiocarbamoyl group, a sulfamoyl group or a substituted or unsubstituted alkyl, alkenyl, alkynyl, alkadienyl, cycloalkyl, cycloalkenyl, cycloalkadienyl, aryl, aralkyl, acyl, alkoxy, alkylthio, acyloxy, cycloalkyloxy, aryloxy, alkoxycarbonyl, cycloalkyloxycarbonyl, acyloxycarbonyl, aralkyloxycarbonyl, alkylsulfonyl, cycloalkylsulfonyl, arylsulfonyl, heterocyclic sulfonyl, alkylcarbamoyl, dialkylcarbamoyl, alkylthiocarbamoyl, dialkylthiocarbamoyl, acylcarbamoyl, acylthiocarbamoyl, alkylsulfonylcarbamoyl, arylsulfonylcarbamoyl, alkylsulfonylthiocarbamoyl, arylsulfonylthiocarbamoyl, alkylsulfamoyl, dialkylsulfamoyl, alkoxythiocarbonyl, alkylideneamino, cycloalkylmethyleneamino, arylmethyleneamino, heterocyclic methyleneamino, or heterocyclic group, or a group of the formula,

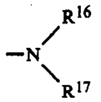

(each of $R^{16}$ and $R^{17}$, which may be the same or different, represents a hydrogen atom or an alkyl group or $R^{16}$ and $R^{17}$ together with their adjacent nitrogen atom may form a ring); each of $R^7$, $R^8$, $R^9$, $R^{10}$, $R^{11}$, $R^{12}$, $R^{14}$ and $R^{15}$, which may be the same or different, represents a hydrogen atom, a halogen atom or a substituted or unsubstituted alkyl, aralkyl or aryl group; $R^{13}$ represents a hydrogen atom, a halogen atom, a carboxyl, sulfo, carbamoyl or thiocarbamoyl group, or a substituted or unsubstituted alkyl, aralkyl, aryl, alkoxy, alkylthio, acyl, alkoxycarbonyl, cycloalkyloxycarbonyl, acyloxycarbonyl, aralkyloxycarbonyl, alkylsulfonyl, cycloalkylsulfonyl, arylsulfonyl, heterocyclic sulfonyl, alkylcarbamoyl, dialkylcarbamoyl, alkylthiocarbamoyl, dialkylthiocarbamoyl, acylcarbamoyl, acylthiocarbamoyl, alkylsulfonylcarbamoyl, arylsulfonylcarbamoyl, alkylsulfonylthiocarbamoyl or arylsulfonylthiocarbamoyl group; $R^3$ represents a hydrogen atom or an alkoxy group; $R^4$ represents a hydrogen atom or a halogen atom; $R^5$ represents a hydrogen atom or a protected or unprotected amino group; and A represents a group of the formula, $-CH_2-$ or a group of the formula,

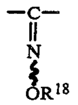

in which $R^{18}$ represents a hydrogen atom, a substituted or unsubstituted alkyl, alkenyl, alkynyl, cycloalkyl, cycloalkenyl, aralkyl, aryl, heterocyclic group or a hydroxyl-protecting group; or a group of the formula,

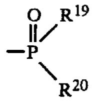

(each of $R^{19}$ and $R^{20}$, which may be the same or different, represents a hydroxyl, alkyl, aralkyl, aryl, alkoxy, aralkyloxy, or aryloxy group), and the bond ∿∿ means that the compound may be a syn-isomer or an anti-isomer or a mixture thereof.

This invention also provides a process for producing said cephalosporins and salts thereof, an antibacterial agent containing said cephalosporins, intermediates for the production of said cephalosphorins and a process for producing said intermediates.

This invention will be further illustrated in detail below.

Herein, unless otherwise specified, the term "alkyl" means a straight or branched chain $C_{1-14}$alkyl and includes, for example, methyl, ethyl, n-propyl, isopropyl, n-butyl, isobutyl, sec.-butyl, tert.-butyl, pentyl, hexyl, heptyl, octyl, dodecyl, lauryl and the like; the term "alkoxy" means O-alkyl in which the alkyl is as defined above; the term "lower alkyl" means a straight or branched chain $C_{1-5}$alkyl and includes, for example, methyl, ethyl, n-propyl, isopropyl, n-butyl, isobutyl, sec.-butyl, tert.-butyl, pentyl and the like; the term "lower alkoxy" means —O—lower alkyl in which the lower alkyl is as defined above, the term "acyl" means a formyl group; a $C_{2-5}$alkanoyl group which includes, for example, acetyl, propionyl, isovaleryl, pivaloyl, pentanecarbonyl and the like; a $C_{5-8}$cycloalkanecarbonyl group which includes, for example, cyclopentylcarbonyl, cyclohexylcarbonyl and the like; an aroyl group which includes, for example, benzoyl, toluoyl, 2-naphthoyl and the like; and a heterocyclic carbonyl group which includes, for example, thenoyl, 3-furoyl, nicotinoyl and the like, the term "acyloxy" means —O—acyl in which the acyl is as defined above; the term "alkylthio" means —S—alkyl in which the alkyl is as defined above; the term "alkenyl" means $C_{2-10}$alkenyl and includes, for example, vinyl, allyl, isopropenyl, 2-pentenyl, butenyl and the like; the term "alkynyl" means $C_{2-10}$alkynyl and includes, for example, ethynyl, 2-propynyl and the like; the term "cycloalkyl" means $C_{3-7}$cycloalkyl and includes, for example, cyclopropyl, cyclobutyl, cyclopentyl, cyclohexyl, cycloheptyl and the like; the term "alkadienyl" means $C_{4-10}$alkadienyl and includes, for example, 1,3-butadienyl, 1,4-hexadienyl and the like; the term "cycloalkenyl" means $C_{5-7}$cycloalkenyl and includes, for example, cyclopentenyl, cyclohexenyl and the like; the term "cycloalkadienyl" means $C_{5-7}$cycloalkadienyl and includes, for example, cyclopentadienyl, cyclohexadienyl and the like; the term "aryl" includes, for example, phenyl, naphthyl, indanyl and the like; the term "aralkyl" includes, for example, benzyl, phenethyl, 4-methylbenzyl, naphthylmethyl and the like; the term "heterocyclic group" means a heterocyclic group containing at least one hetero atom selected from oxygen, nitrogen and sulfur and includes, for example, furyl, thienyl, pyrrolyl, pyrazolyl, imidazolyl, thiazolyl, isothiazolyl, oxazolyl, isoxazolyl, thiadiazolyl, oxadiazolyl, thiatriazolyl, oxatriazolyl, triazolyl, tetrazolyl, pyridyl, 4-(5-methyl-2-pyrrolinyl), 4-(2-pyrrolinyl), N-methylpiperidinyl, quinolyl, phenazinyl, 1,3-benzodioxolanyl, benzofuryl, benzothienyl, benzoxazolyl, benzothiazolyl, phthalidyl, coumarinyl and the like; the term "heterocyclic alkyl" means a group consisting of the above-defined heterocyclic group and the abovedefined alkyl group; and the term "halogen atom" includes, for example, flourine, chlorine, bromine and iodine.

The symbol $R^1$ in the formulas in this specification represents a hydrogen atom or a carboxyl-protecting group, and the carboxyl-protecting group includes those which are conventionally used in the fields of penicillins and cephalosporins, for example, an ester-forming group which can be removed by a catalytic hydrogenation, a chemical reduction, or a treatment under other mild conditions; an ester-forming group which can be easily removed in a living body; or an organic silyl-containing group, an organic phosphorus-containing group, or an organic tin-containing group or the like, which can easily be removed upon treating with water or an alcohol; and other various well-known ester-forming groups.

Among these protecting groups, preferable groups are as follows:

(a) alkyl groups, for example, $C_{1-4}$alkyl, (b) substituted lower alkyl groups wherein at least one of the substituents is selected from a halogen atom, or a nitro, acyl, alkoxy, oxo, cyano, hydroxyl, cycloalkyl, aryl, alkylthio, alkylsulfinyl, alkylsulfonyl, alkoxycarbonyl, 5-alkyl-2-oxo-1,3-dioxol-4-yl, 1-indanyl, 2-indanyl, furyl, pyridyl, 4-imidazolyl, phthalimido, succinimido, azetidino, aziridino, pyrrolidino, piperidino, morpholino, thiomorpholino, N-lower-alkylpiperazino, pyrrolyl, pyrazolyl, thiazolyl, isothiazolyl, oxazolyl, isoxazolyl, thiadiazolyl, oxadiazolyl, thiatriazolyl, oxatriazolyl, triazolyl, tetrazolyl, quinolyl, phenazinyl, benzofuryl, benzothienyl, benzoxazolyl, benzothiazolyl, coumarinyl, 2,5-dimethylpyrrolidino, 1,4,5,6-tetrahydropyrimidinyl, 4-methylpiperidino, 2,6-dimethylpiperidino, 4-(5-methyl-2-pyrrolinyl), 4-(2-pyrrolinyl), N-methylpiperidinyl, 1,3-benzodioxolanyl, alkylamino, dialkylamino, acyloxy, acylthio, acylamino, dialkylaminocarbonyl, alkoxycarbonylamino, alkenyloxy, aryloxy, aralkyloxy, cycloalkyloxy, cycloalkenyloxy, heterocyclic oxy, alkoxycarbonyloxy, alkenyloxycarbonyloxy, aryloxycarbonyloxy, aralkyloxycarbonyloxy, heterocyclic oxycarbonyloxy, alkenyloxycarbonyl, aryloxycarbonyl, aralkyloxycarbonyl, cycloalkyloxycarbonyl, cycloalkenyloxycarbonyl, heterocyclic oxycarbonyl or alkylanilino group or an alkylanilino group substituted by a halogen atom, a lower alkyl or lower alkoxy group, (c) cycloalkyl group; lower alkyl-substituted cycloalkyl group; or (2,2-di-lower-alkyl-1,3-dioxol-4-yl)methyl groups, (d) alkenyl groups, (e) alkynyl groups, (f) phenyl group; substituted phenyl groups wherein at least one of the substituents are selected from the substituents specifically mentioned in above (b); or aryl groups such as groups represented by the formula:

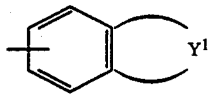

wherein $-Y^1-$ is $-CH{=}CH-O-$, $-CH{=}CH-S-$, $-CH_2CH_2S-$, $-CH{=}N-CH{=}N-$, $-CH{=}CH-CH{=}CH-$, $-CO-CH{=}CH-CO-$, or $-CO-CO-CH{=}CH-$, or a substituted derivative thereof wherein the substituents are selected from those specifically mentioned in above (b), or groups represented by the formula:

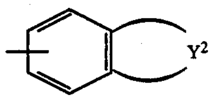

wherein $-Y^2-$ is a lower alkylene group such as $-(CH_2)_3-$ or $-(CH_2)_4-$, or a substituted derivative thereof wherein the substituents are selected from those specifically mentioned in above (b), (g) aralkyl groups such as benzyl or substituted benzyl groups wherein at least one of the substituents are selected from those specifically mentioned in above (b), (h) heterocyclic group or substituted heterocyclic groups wherein at least one of the substituents are selected from those specifically mentioned in above (b), (i) indanyl or phthalidyl groups or substituted derivatives thereof wherein the substituents are methyls or halogens; tetrahydronaphthyl groups are substituted derivatives thereof wherein the substituents are methyls or halogens; trityl, cholesteryl, bicyclo[4,4,0]decyl; or the like, (j) phthalidylidene-lower-alkyl groups or substituted derivatives thereof wherein the substituents are halogens or lower alkyl groups.

The above-mentioned carboxyl-protecting groups are typical examples, and the carboxyl-protecting group may also be selected from the other protecting groups described in the following literature: U.S. Pat. Nos. 3,499,909, 3,573,296 and 3,641,018; DT-OS Nos. 2,301,014, 2,253,287 and 2,337,105.

Among these carboxyl-protecting groups, preferable are diphenylmethyl, 5-lower alkyl-2-oxo-1,3-dioxol-4-yl-lower alkyl groups, acyloxyalkyl groups, acylthioalkyl groups, phthalidyl group, indanyl group, phenyl group, substituted or unsubstituted phthalidylidene lower alkyl groups or those groups which can easily be removed in a living body such as groups represented by the following formulas:

$$-\underset{R^{22}}{\underset{|}{CH}}(CH_2)_mOR^{21},\ -\underset{R^{22}}{\underset{|}{CH}}OCOOR^{21},\ \text{and}\ -\underset{R^{23}}{\underset{|}{CH}}(CH_2)_mCOOR^{21}$$

wherein $R^{21}$ represents a known substituted or unsubstituted alkyl, alkenyl, aryl, aralkyl, alicyclic or heterocyclic group; $R^{22}$ represents a hydrogen atom or a known substituted or unsubstituted alkyl, alkenyl, aryl, aralkyl, alicyclic or heterocyclic group; $R^{23}$ represents a hydrogen atom, a halogen atom or a known substituted or unsubstituted alkyl, cycloalkyl, aryl or heterocyclic group, or $-(CH_2)_nCOOR^{21}$ ($R^{21}$ has the same meaning as defined above, and n represents 0, 1 or 2); and m represents 0, 1 or 2.

More specifically, there may be used 5-lower alkyl-2-oxo-1,3-dioxol-4-yl-methyl groups such as 5-methyl-2-oxo-1,3-dioxol-4-yl-methyl, 5-ethyl-2-oxo-1,3-dioxol-4-yl-methyl, 5-propyl-2-oxo-1,3-dioxol-4-yl-methyl and the like; acyloxyalkyl groups such as acetoxymethyl, pivaloyloxymethyl, propionyloxymethyl, butyryloxymethyl, isobutyryloxymethyl, valeryloxymethyl, 1-acetoxyethyl, 1-acetoxy-n-propyl, 1-pivaloyloxyethyl, 1-pivaloyloxy-n-propyl and the like; acylthioalkyl groups such as acetylthiomethyl, pivaloylthiomethyl, benzoylthiomethyl, p-chlorobenzoylthiomethyl, 1-acetylthioethyl, 1-pivaloylthioethyl, 1-benzoylthioethyl, 1-(p-chlorobenzoylthio)ethyl and the like; alkoxymethyl groups such as methoxymethyl, ethoxymethyl, propoxymethyl, isopropoxymethyl, n-butyloxymethyl and the like; alkoxycarbonyloxyalkyl groups such as methoxycarbonyloxymethyl, ethoxycarbonyloxymethyl, propoxycarbonyloxymethyl, isopropoxycarbonyloxymethyl, n-butoxycarbonyloxymethyl, tert.-butoxycarbonyloxymethy, 1-methoxycarbonyloxyethyl, 1-ethoxycarbonyloxyethyl, 1-propoxycarbonyloxyethyl, 1-isopropoxycarbonyloxyethyl, 1-tert.-butoxycarbonyloxyethyl, 1-n-butoxycarbonyloxyethyl and the like; alkoxycarbonylmethyl groups such as methoxycarbonylmethyl, ethoxycarbonylmethyl and the like; phthalidyl group; indanyl group; phenyl group; phthalidilidenealkyl groups such as 2-(phthalidylidene)ethyl, 2-(5-fluorophthalidylidene)ethyl, 2-(6-chlorophthalidylidene)ethyl, 2-(6-methoxyphthalidylidene)ethyl and the like; etc.

$R^2$ represents a group of the formula:

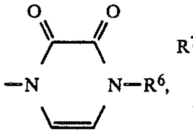
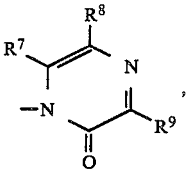
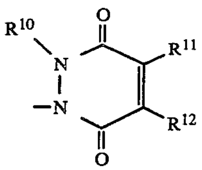
or
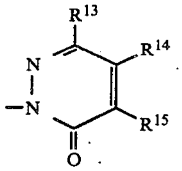

in which $R^6$ represents a hydrogen atom, a hydroxyl group, a nitro group, a carbamoyl group, a thiocarbamoyl group, a sulfamoyl group, or a substituted or unsubstituted alkyl, alkenyl, alkynyl, alkadienyl, cycloalkyl, cycloalkenyl, cycloalkadienyl, aryl, aralkyl, acyl, alkoxy, alkylthio, acyloxy, cycloalkyloxy, aryloxy, alkoxycarbonyl, cycloalkyloxycarbonyl, acyloxycarbonyl, aralkyloxycarbonyl, alkylsulfonyl, cycloalkylsulfonyl, arylsulfonyl, heterocyclic sulfonyl, alkylcarbamoyl, dialkylcarbamoyl, alkylthiocarbamoyl, dialkylthiocarbamoyl, acylcarbamoyl, acylthiocarbamoyl, alkylsulfonylcarbamoyl, arylsulfonylcarbamoyl, alkylsulfonylthiocarbamoyl, arylsulfonylthiocarbamoyl, alkylsulfamoyl, dialkylsulfamoyl, alkoxythiocarbonyl, alkylideneamino, cycloalkylmethyleneamino, arylmethyleneamino, heterocyclic methyleneamino or heterocyclic group; a group of the formula,

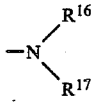

(each of $R^{16}$ and $R^{17}$, which may be the same or different, represents a hydrogen atom or an alkyl group, or $R^{16}$ and $R^{17}$ together with their adjacent nitrogen atom may form a ring), each of $R^7$, $R^8$, $R^9$, $R^{10}$, $R^{11}$, $R^{12}$, $R^{14}$ and $R^{15}$, which may be the same or different, represents a hydrogen atom, a halogen atom, or a substituted or unsubstituted alkyl, aralkyl or aryl group; $R^{13}$ represents a hydrogen atom, a halogen atom, a carboxyl group, a sulfo group, a carbamoyl group, a thiocarbamoyl group, or a substituted or unsubstituted alkyl, aralkyl, aryl, alkoxy, alkylthio, acyl, alkoxycarbonyl, cycloalkyloxycarbonyl, acyloxycarbonyl, aralkyloxycarbonyl, alkylsulfonyl, cycloalkylsulfonyl, arylsulfonyl, heterocyclic sulfonyl, alkylcarbamoyl, dialkylcarbamoyl, alkylthiocarbamoyl, dialkylthiocarbamoyl, acylcarbamoyl, acylthiocarbamoyl, alkylsulfonylcarbamoyl, arylsulfonylcarbamoyl, alkylsulfonylthiocarbamoyl or arylsulfonylthiocarbamoyl group. In each of the groups for $R^6$ and $R^{13}$ mentioned above, the term "cycloalkyloxy" means —O-cycloalkyl, the term "aryloxy" means —O-aryl, the term "alkoxycarbonyl" means

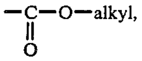

the term "cycloalkyloxycarbonyl" means

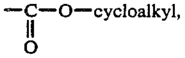

the term "acyloxycarbonyl" means

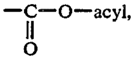

the term "aralkyloxycarbonyl" means

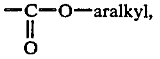

the term "alkylsulfonyl" means —$SO_2$-alkyl, the term "cycloalkylsulfonyl" means —$SO_2$-cycloalkyl, the term "arylsulfonyl" means —$SO_2$-aryl, the term "heterocyclic sulfonyl" means —$SO_2$-heterocyclic ring, the term "alkylcarbamoyl" means

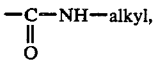

the term "dialkyl carbamoyl" means

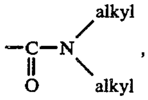

the term "alkylthiocarbamoyl" means

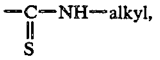

the term "dialkylthiocarbamoyl" means

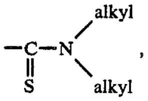

the term "acylcarbamoyl" means

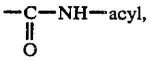

the term "acylthiocarbamoyl" means

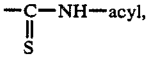

the term "alkylsulfonylcarbamoyl" means

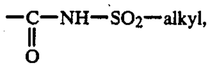

the term "arylsulfonylcarbamoyl" means

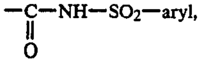

the term "alkylsulfonylthiocarbamoyl" means

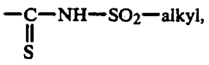

the term "arylsulfonylthiocarbamoyl" means

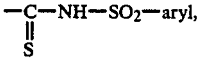

the term "alkylsulfamoyl" means —$SO_2$—NH-alkyl, the term "dialkylsulfamoyl" means

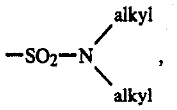

the term "alkoxythiocarbonyl" means

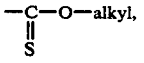

the term "alkylideneamino" means —N═CH-alkyl, the term "cycloalkylmethyleneamino" means —N═CH-cycloalkyl, the term "arylmethyleneamino" means —N═CH-aryl, and the term "heterocyclic methyleneamino" means —N═CH-heterocyclic ring.

The groups of the formula,

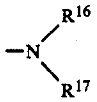

wherein $R^{16}$ and $R^{17}$ have the same meanings as defined above include amino group, alkylamino groups represented by —NH-alkyl, dialkylamino groups represented by

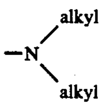

and groups represented by the formulas

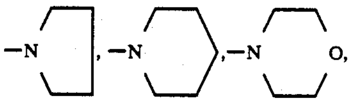

-continued

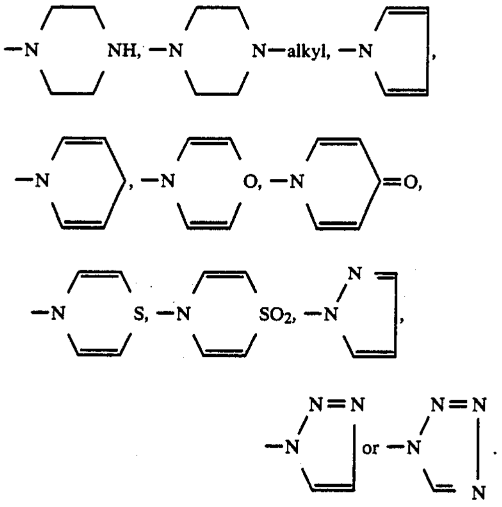

The substituents for the various groups mentioned above include halogen atoms, alkyl groups, aralkyl groups, aryl groups, alkenyl groups, hydroxyl group, oxo group, alkoxy groups, alkylthio groups, nitro group, cyano group, amino group, acyl groups, acyloxy groups, carboxyl group, carbamoyl group, sulfo group, sulfamoyl group, alkylamino groups represented by —NH-alkyl, dialkylamino groups represented by

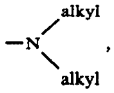

acylamino groups represented by —NH-acyl, alkoxycarbonyl groups represented by

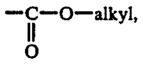

acylalkyl groups such as acetylmethyl, propionylmethyl and the like, aminoalkyl groups such as aminomethyl, aminoethyl and the like, N-alkylaminoalkyl groups such as N-methylaminomethyl, N-methylaminoethyl and the like, N,N-dialkylaminoalkyl groups such as N,N-dimethylaminomethyl, N,N-dimethylaminoethyl and the like, hydroxyalkyl groups such as hydroxymethyl, hydroxyethyl and the like, hydroxyiminoalkyl groups such as hydroxyiminomethyl, hydroxyiminoethyl and the like, alkoxyalkyl groups such as methoxymethyl, methoxyethyl, ethoxymethyl, ethoxyethyl and the like, carboxyalkyl groups such as carboxymethyl, carboxyethyl and the like, alkoxycarbonylalkyl groups such as methoxycarbonylmethyl, methoxycarbonylethyl, ethoxycarbonylmethyl, ethoxycarbonylethyl and the like, aralkyloxycarbonylalkyl groups such as benzyloxycarbonylmethyl, benzyloxycarbonylethyl and the like, sulfoalkyl groups such as sulfomethyl, sulfoethyl and the like, sulfamoylalkyl groups such as sulfamoylmethyl, sulfamoylethyl and the like, carbamoylalkyl groups such as carbamoylmethyl, carbamoylethyl and the like, carbamoylalkenyl groups such as carbamoylallyl and the like, N-hydroxycarbamoylalkyl groups such as N-hydroxycarbamoylmethyl, N-hydroxycarbamoylethyl and the like, a group of the formula

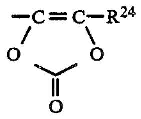

in which $R^{24}$ represents a lower alkyl group, etc. The above-mentioned various groups as to $R^6$, $R^7$, $R^8$, $R^9$, $R^{10}$, $R^{11}$, $R^{12}$, $R^{13}$, $R^{14}$ and $R^{15}$ may be substituted by at least one of the above-mentioned substituents. Among the above substituents, the hydroxyl group, the amino group and the carboxyl group may be protected by a suitable protecting group usually available in the art. The hydroxyl-protecting groups include all hydroxyl-protecting groups which can be usually used, such as easily removable acyl groups, for example, benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, tert.-butoxycarbonyl, 1,1-dimethylpropoxycarbonyl, isopropoxycarbonyl, diphenylmethoxycarbonyl, 2,2,2-trichloroethoxycarbonyl, 2,2,2-tribromoethoxycarbonyl, 2-furfuryloxycarbonyl, 1-adamantyloxycarbonyl, 1-cyclopropylethoxycarbonyl, 8-quinolyloxycarbonyl, formyl, acetyl, chloroacetyl, benzoyl, trifluoroacetyl and the like; alkylsulfonyl groups, for example, methanesulfonyl, ethanesulfonyl and the like; arylsulfonyl groups, for example, phenylsulfonyl, toluenesulfonyl and the like; benzyl group; diphenylmethyl group; trityl group; methoxymethyl group; tetrahydropyranyl group; tetrahydrofuranyl group; 2-nitrophenylthio group; 2,4-dinitrophenylthio group; and the like.

In addition, the amino-protecting groups include all usually usable amino-protecting groups such as easily removable acyl groups, for example, 2,2,2-trichloroethoxycarbonyl, 2,2,2-tribromoethoxycarbonyl, benzyloxycarbonyl, p-toluenesulfonyl, 4-nitrobenzyloxycarbonyl, 2-bromobenzyloxycarbonyl, acetyl, (mono-, di-, tri-)chloroacetyl, trifluoroacetyl, formyl, tert.-amyloxycarbonyl, tert.-butoxycarbonyl, 4-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, pyridine-1-oxide-2-ylmethoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl and the like; further easily removable groups, for example, trityl, o-nitrophenylsulfonyl, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene, 4-nitrofurfurylidene and the like; di- or trialkylsilyl group; and the like. Then, the carboxyl-protecting groups include all usually usable carboxyl-protecting groups, and there are cases where the carboxyl group is protected by such a group as methyl, ethyl, n-propyl, isopropyl, tert.-butyl, n-butyl, benzyl, diphenylmethyl, trilyl, 4-nitrobenzyl, 4-methoxybenzyl, benzoylmethyl, acetylmethyl, 4-nitrobenzoylmethyl, p-bromobenzoylmethyl, 4-methanesulfonylbenzoylmethyl, phthalimidomethyl, 2,2,2-trichloroethyl, 1,1-dimethyl-2-propenyl, 1,1-dimethylpropyl, acetoxymethyl, propionyloxymethyl, pivaloyloxymethyl, 3methyl-3-butynyl, succinimidomethyl, 1-cyclopropylethyl, methylthiomethyl, phenylthiomethyl, dimethylaminomethyl, quinoline-1-oxide-2-ylmethyl, pyridine-1-oxide-2-ylmethyl, bis(p-methoxyphenyl)methyl and the like, where the carboxyl group is protected by a non-metal compound such as titanium tetrachloride, and where the carboxyl group is protected by a silyl compound such as dimethylchlorosilane as described in Japanese Patent Application Kokai (laid-Open) No. 7073/71 and Dutch Patent Application No. 7105259 (Laid-Open).

$R^5$ represents a hydrogen atom or a protected or unprotected amino group, and such amino-protecting groups include many groups usually employed in the fields of penicillins and cephalosporins, specifically all the amino-protecting groups mentioned above as to $R^2$.

A represents a group of the formula, $-CH_2-$ or a group of the formula,

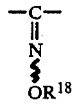

in which $R^{18}$ represents a hydrogen atom; a substituted or unsubstituted alkyl, alkenyl, alkynyl, cycloalkyl, cycloalkenyl, aralkyl, aryl, heterocyclic group or a hydroxyl-protecting group, or a group of the formula

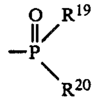

(each of $R^{19}$ and $R^{20}$, which may be the same or different, represents a hydroxyl, alkyl, aralkyl, aryl, alkoxy, aralkyloxy or aryloxy group) and the bond ∿ means that the compound may be a syn-isomer or an anti-isomer or a mixture thereof. The said hydroxyl-protecting group includes the hydroxyl-protecting groups mentioned as to $R^2$. In addition, the above-mentioned various groups for $R^{18}$ may be substituted by at least one substituent selected from halogen atoms, oxo group, cyano group, hydroxyl group, alkoxy groups, amino group, alkylamino groups, dialkylamino groups, heterocyclic groups and groups of the formulas:

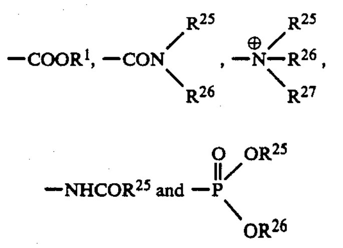

wherein $R^1$ has the same meaning as defined above, and each of $R^{25}$, $R^{26}$ and $R^{27}$, which may be the same or different, represents a hydrogen atom, an alkyl group, an aralkyl group or an aryl group. Among these substituents, the hydroxyl group, the amino group, and the carboxyl group may be protected respectively by the hydroxyl-protecting group and the amino-protecting group mentioned as to $R^2$ and the carboxyl-protecting group mentioned as to $R^1$.

The oximes of the formula,

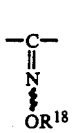

include syn- and anti-isomers and mixtures thereof.

In the

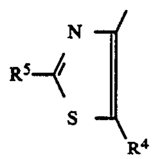

group of each formula in this invention, there are tautomers as shown by the following equilibrium formulas where $R^5$ is a protected or unprotected amino group, and such tautomers are included in this invention:

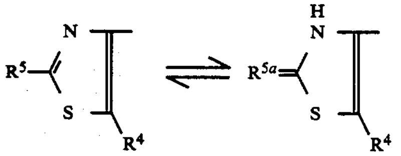

wherein $R^4$ and $R^5$ have the same meanings as defined above, and $R^{5a}$ represents a protected or unprotected imino group. In the above formulas, the imino-protecting group for $R^{5a}$ includes those groups used in the fields of penicillins and cephalosporins, and specifically, same groups as the monovalent groups among the amino-protecting groups mentioned above as to $R^2$.

When the $-CH_2R^2$ group in the formula [I] is a group of the formula:

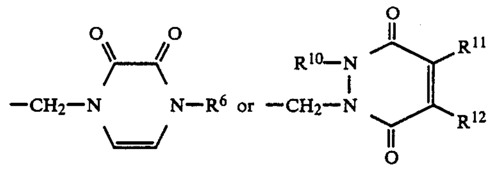

wherein $R^6$, $R^{10}$, $R^{11}$ and $R^{12}$ have the same meanings as defined above, there are tautomers as shown in the following equilibrium formulas when each of $R^6$ and $R^{10}$ is a hydrogen atom, and the tautomers are also included in this invention:

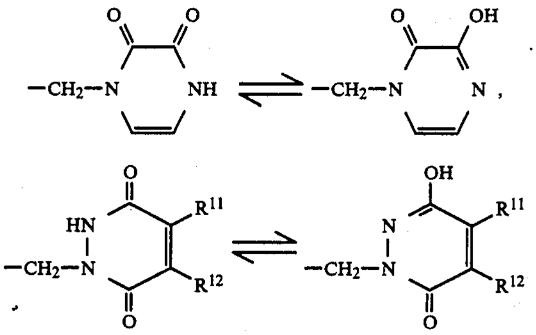

The salts of the compounds of the formula [I] include salts at the basic group and the acidic group which are well-known in the fields of penicillins and cephalosporins. The salts at the basic group include salts with mineral acids such as hydrochloric acid, nitric acid, sulfuric acid and the like; salts with organic carboxylic acids such as oxalic acid, succinic acid, formic acid, trichloroacetic acid, trifluoroacetic acid and the like; and salts with sulfonic acids such as methanesulfonic acid, ethanesulfonic acid, benzenesulfonic acid, toluene-2-sulfonic acid, toluene-4-sulfonic acid, mesitylenesulfonic acid (2,4,6-trimethylbenzenesulfonic acid), naphthalene-1-sulfonic acid, naphthalene-2-sulfonic acid, phenylmethanesulfonic acid, benzene-1,3-disulfonic acid, toluene-3,5-disulfonic acid, naphthalene-1,5-disulfonic acid, naphthalene-2,6-disulfonic acid, napthalene-2,7-disulfonic acid, benzene-1,3,5-trisulfonic acid, benzene-1,2,4-trisulfonic acid, naphthalene-1,3,5-trisulfonic acid and the like. The salts at the acidic group include salts with alkali metals such as sodium, potassium, and the like; salts with alkaline earth metals such as calcium, magnesium and the like; ammonium salts; and salts with nitrogen-containing organic bases such as procaine, dibenzylamine, N-benzyl-$\beta$-phenethylamine, 1-ephenamine, N,N-dibenzylethylenediamine, triethylamine, trimethylamine, tributylamine, pyridine, N,N-dimethylaniline, N-methylpiperidine, N-methylmorpholine, diethylamine, dicyclohexylamine and the like.

This invention includes all optical isomers and the racemic compounds of cephalosphorins of the formula [I] and their salts, and also all crystal forms and hydrates of the said compounds. More specifically, preferable examples of the compounds represented by the formula [I] are oximes in which A is a group of the formula,

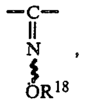

particularly syn-isomers thereof, in which $R^{18}$ is preferably an alkyl group, especially methyl, ethyl; or a substituted alkyl group, especially $-CH_2COOR^1$ or 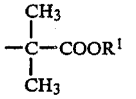

($R^1$ has the same meaning as defined above).

Preferable examples of $R^2$ are groups of the formula,

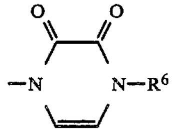

in which $R^6$ is a hydrogen atom, a substituted or unsubstituted lower alkyl group or a group of the formula,

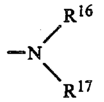

($R^{16}$ and $R^{17}$ have the same meanings as defined above); groups of the formula,

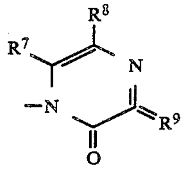

in which each of $R^7$, $R^8$ and $R^9$, which may be the same or different, represents a hydrogen atom or an alkyl group; groups of the formula,

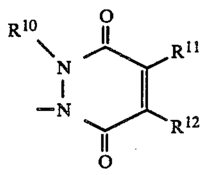

in which each of $R^{10}$, $R^{11}$ and $R^{12}$, which may be the same or different, represents a hydrogen atom, a halogen atom or an alkyl group; and groups of the formula,

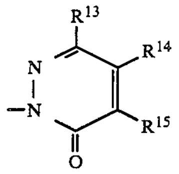

in which each of $R^{13}$, $R^{14}$ and $R^{15}$, which may be the same or different represents a hydrogen atom or an alkyl group.

Next, pharmacological effects are shown on some typical compounds represented by the formupla [I].

(1) Antibacterial activity (Table 1)

According to the standard method of Japan Society of Chemotherapy ["CHEMOTHERAPY", Vol. 23, pp. 1-2 (1975)], a bacterial solution obtained by culturing in Heart Infusion broth (manufactured by Eiken Kagaku) at 37° C. for 20 hours was inoculated onto a Heart Infusion agar containing a drug and cultured at 37° C. for 20 hours, after which the growth of the bacteria was observed, to determine the minimum concentration at which the growth of the bacteria was inhibited as MIC (μg/ml). The amount of the inoculated bacteria was $10^4$ cells/plate ($10^6$ cells/ml). The MIC values of the following test compounds are as shown in Table 1:

(A) trifluoroacetic acid salt of 7-[2-(2-aminothiazol-4-yl)-2-(syn)-methoxyiminoacetamido]-3-{[1-(2,3-dioxo-1,2,3,4-tetrahydropyrazinyl)]methyl}-$\Delta^3$-cephem-4-carboxylic acid, (B) trifluoroacetic acid salt of 7-[2-(2-aminothiazol-4yl)-2-(syn)-methoxyiminoacetamido]-3-{[1-(4-methyl-2,3-dioxo-1,2,3,4-tetrahydropyrazinyl)]methyl}-$\Delta^3$-cephem-4-carboxylic acid, (C) trifluoroacetic acid salt of 7-[2-(2-aminothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylic acid, (D) trifluoroacetic acid salt of 7-[2-(2-aminothiazol-4-yl)-(syn)-methoxyiminoacetamido]-3-{[1-(4-isopropyl-2,3-dioxo-1,2,3,4-tetrahydropyrazinyl)]methyl}-$\Delta^3$-cephem-4-carboxylic acid, (E) trifluoroacetic acid salt of 7-[2-(2-aminothiazol-4-yl)-2-(syn)-methoxyiminoacetamido]-3-{[1-(4-dimethylamino-2,3-dioxo-1,2,3,4-tetrahydropyrazinyl)]-methyl}-$\Delta^3$-cephem-4-carboxylic acid, (F) 7-[2-(2-aminothiazol-4-yl)-2-(syn)-carboxymethoxyiminoacetamido]-3-{[1-(2,3-dioxo-1,2,3,4-tetrahydropyrazinyl)]methyl}-$\Delta^3$-cephem-4-carboxylic acid, (G) trifluoroacetic acid salt of 7-[2-(2-aminothiazol-4-yl)-2-(syn)-carboxymethoxyiminoacetamido-9 -3-{[1-(4-methyl-2,3-dioxo-1,2,3,4-tetrahydropyrazinyl)]methyl}-$\Delta^3$-cephem-4-carboxylic acid, (H) trifluoroacetic acid salt of 7-[2-(2-aminothiazol-4-yl)-2-(syn)-carboxymethoxyiminoacetamido]-3-{[1-(4-ethyl-2,3-dioxo-1,2,3,4-tetrahydropyrazinyl)]methyl}-$\Delta^3$-cephem-4-carboxylic acid, (I) trifluoroacetic acid salt of 7-[2-(2-aminothiazol-4-yl)-2-(syn)-carboxymethoxyiminoacetamido]-3-{[1-(4-dimethylamino-2,3-dioxo-1,2,3,4-tetrahydropyrazinyl)]methyl}-$\Delta^3$-cephem-4-carboxylic acid, (J) trifluoroacetic acid salt of 7-[2-(2-aminothiazol-4-yl)-2-(syn)-methoxyiminoacetamido]-3-{[1-(2-oxo-1,2-

TABLE 1

Antibacterial Activity

MIC (μg/ml)

| Organism | Compound A | B | C | D | E | F | G | H | I | J | K | L | M | N |
|---|---|---|---|---|---|---|---|---|---|---|---|---|---|---|
| *E. coli* NIHJ | ≦0.1 | ≦0.1 | ≦0.1 | ≦0.1 | ≦0.1 | ≦0.1 | ≦0.1 | ≦0.1 | ≦0.1 | ≦0.1 | ≦0.1 | ≦0.1 | ≦0.1 | ≦0.1 |
| *E. coli* TK-3* | ≦0.1 | ≦0.1 | ≦0.1 | ≦0.1 | ≦0.1 | ≦0.1 | 0.2 | ≦0.1 | ≦0.1 | 0.2 | 0.2 | 0.78 | 0.2 | 0.2 |
| *Kl. pneumoniae* Y-50 | ≦0.1 | ≦0.1 | ≦0.1 | ≦0.1 | ≦0.1 | ≦0.1 | 0.2 | 0.2 | 0.2 | ≦0.1 | ≦0.1 | 0.78 | 0.2 | 0.39 |
| *Kl. pneumoniae* Y-41 | ≦0.1 | ≦0.1 | ≦0.1 | ≦0.1 | ≦0.1 | 0.39 | ≦0.1 | ≦0.1 | 0.2 | — | — | — | — | — |
| *Kl. pneumoniae* Y-4* | ≦0.1 | 0.2 | ≦0.1 | 0.39 | ≦0.1 | 0.2 | 0.2 | 0.2 | 0.39 | — | — | — | — | — |
| *Ser. marcescens* W-134 | ≦0.1 | ≦0.1 | ≦0.1 | ≦0.1 | ≦0.1 | ≦0.1 | ≦0.1 | ≦0.1 | ≦0.1 | 0.39 | ≦0.1 | ≦0.1 | 0.78 | ≦0.1 |
| *Ser. marcescens* IID620 | ≦0.1 | ≦0.1 | ≦0.1 | ≦0.1 | ≦0.1 | ≦0.1 | ≦0.1 | ≦0.1 | ≦0.1 | ≦0.1 | ≦0.1 | 1.56 | 0.2 | ≦0.1 |
| *Pro. morganii* T-216 | ≦0.1 | ≦0.1 | ≦0.1 | ≦0.1 | ≦0.1 | ≦0.1 | ≦0.1 | ≦0.1 | ≦0.1 | ≦0.1 | ≦0.1 | ≦0.1 | 0.2 | ≦0.1 |
| *Pro. mirabilis* T-111 | ≦0.1 | ≦0.1 | ≦0.1 | 0.2 | ≦0.1 | ≦0.1 | ≦0.1 | ≦0.1 | ≦0.1 | 0.2 | ≦0.1 | ≦0.1 | 0.2 | ≦0.1 |
| *Pro. vulgaris* GN76** | ≦0.1 | 0.2 | 1.56 | 0.39 | 1.56 | ≦0.1 | ≦0.1 | ≦0.1 | ≦0.1 | 0.78 | ≦0.1 | ≦0.1 | 0.2 | ≦0.1 |
| *Cit. freundii* N-7 | 0.39 | 1.56 | 0.78 | 1.56 | 0.78 | 0.78 | 1.56 | 1.56 | 1.56 | 0.78 | 0.78 | 3.13 | 0.78 | 0.78 |
| *Ps. aeruginosa* GN918** | 12.5 | 25 | 6.25 | — | — | — | — | 6.25 | 12.5 | — | — | — | — | — |

Note:
*Penicillinase-producing strain
**Cephalosporinase-producing strain dihydropyrazinyl)]methyl}-$\Delta^3$-cephem-4-carboxylic acid, (K) trifluoroacetic acid salt of 7-[2-(2-aminothiazol-4-yl)-2-(syn)-methoxyiminoacetamido]-3-{[1-(3,6-dioxo-1,2,3,6-tetrahydropyridazinyl)]methyl}-$\Delta^3$-cephem-4-carboxylic acid, (L) formic acid salt of 7-[2-(2-aminothiazol-4-yl)-2-(syn)-carboxymethoxyiminoacetamido]-3-{[1-(3,6-dioxo-1,2,3,6-tetrahydropyridazinyl)]methyl}-$\Delta^3$-cephem-4-carboxylic acid, (M) trifluoroacetic acid salt of 7-[2-(2aminothiazol-4-yl)-2-(syn)-methoxyiminoacetamido]-3-{[1-(3-methyl-6-oxo-1,6-dihydropyridazinyl)]methyl}-$\Delta^3$-cephem-4-carboxylic acid, and (N) formic acid salt of 7-[2-(2-aminothiazol-4-yl)-2-(syn)-carboxymethoxyiminoacetamido]-3-{[1-(3-methyl-6-oxo-1,6-dihydropyridazinyl]methyl}-$\Delta^3$-cephem-4-carboxylic acid.

(2) Urinary recovery

A test compound was orally administered to mice (ICR, male, 4 weeks old) in an amount of 1 mg/mouse, and a urinary recovery was determined. The results obtained are shown in Table 2.

In the test compounds (No. 1 and No. 2), the ester group is easily removed in a living body, whereby the compounds are converted into the corresponding free carboxylic acids. Therefore, the urinary recovery was determined by quantitatively measuring the free carboxylic acids excreted into urine.

Administration method: A test compound suspended in 0.5% CMC (Carboxy Methyl Cellulose) was orally administered.

Quantitative measurement method: The amount of free carboxylic acid was measured by bioassay (a paper-disc method) using the test organism mentioned in Table 2.

TABLE 2

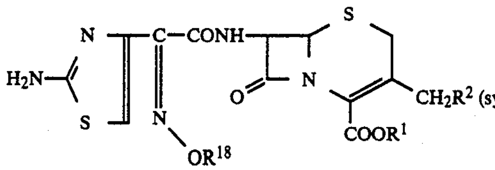

(syn-isomer)

| No. | Compound $R^{18}$ | $R^1$ | $R^2$ | Test organism | Urinary Recovery* (%) |
|---|---|---|---|---|---|
| 1 | $-CH_3$ | $-CH_2OCOC(CH_3)_3$ | 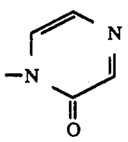 | *Kl. pneumoniae* ATCC 10031 | 15.9 ± 1.6 |

TABLE 2-continued

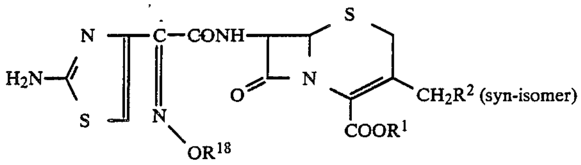

| No. | Compound R[18] | R[1] | R[2] | Test organism | Urinary Recovery* (%) |
|---|---|---|---|---|---|
| 2 | $-CH_3$ | $-CH_2OCOC(CH_3)_3$ | 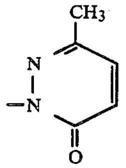 | *Kl. pneumoniae* ATCC 10031 | 20.4 ± 3.7 |
| 3 | $-CH_2COOH$ | —H | 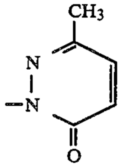 | *Kl. pneumoniae* ATCC 10031 | 10.4 ± 1.1 |

Note:
*0–6 hours, one group; 5 mice (mean ±S.E.)

(3) Acute toxicity $LD_{50}$ values of the following test compounds were 3 g/kg or more when the compounds were intravenously administered to mice (ICR, male, body weight 20–24 g).

Test compounds:

Sodium 7-[2-(2-aminothiazol-4-yl)-2-(syn)methoxyiminoacetamido)]-3-{[1-(2,3-dioxo-1,2,3,4-tetrahydropyrazinyl]methyl}-$\Delta^3$-cephem-4-carboxylate, sodium 7-[2-(2-aminothiazol-4-yl)-2-(syn)methoxyiminoacetamido]-3-{[1-(4-methyl-2,3-dioxo-1,2,3,4-tetrahydropyrazinyl)]methyl}-$\Delta^3$-cephem-4-carboxylate, sodium 7-[2-(2-aminothiazol-4-yl)-2-(syn)methoxyiminoacetamido]-3-{[1-(3,6-dioxo-1,2,3,6-tetrahydropyridazinyl)]methyl}-$\Delta^3$-cephem-4-carboxylate, and sodium 7-[2-(2-aminothiazol-4-yl)-2-(syn)methoxyiminoacetamido]-3-{[1-(3-methyl-6-oxo-1,6-dihydropyridazinyl)]methyl}-$\Delta^3$-cephem-4-carboxylate.

Next, an explanation is made below of production processes.

The compound of this invention can be prepared by the following processes:

Production Route 1
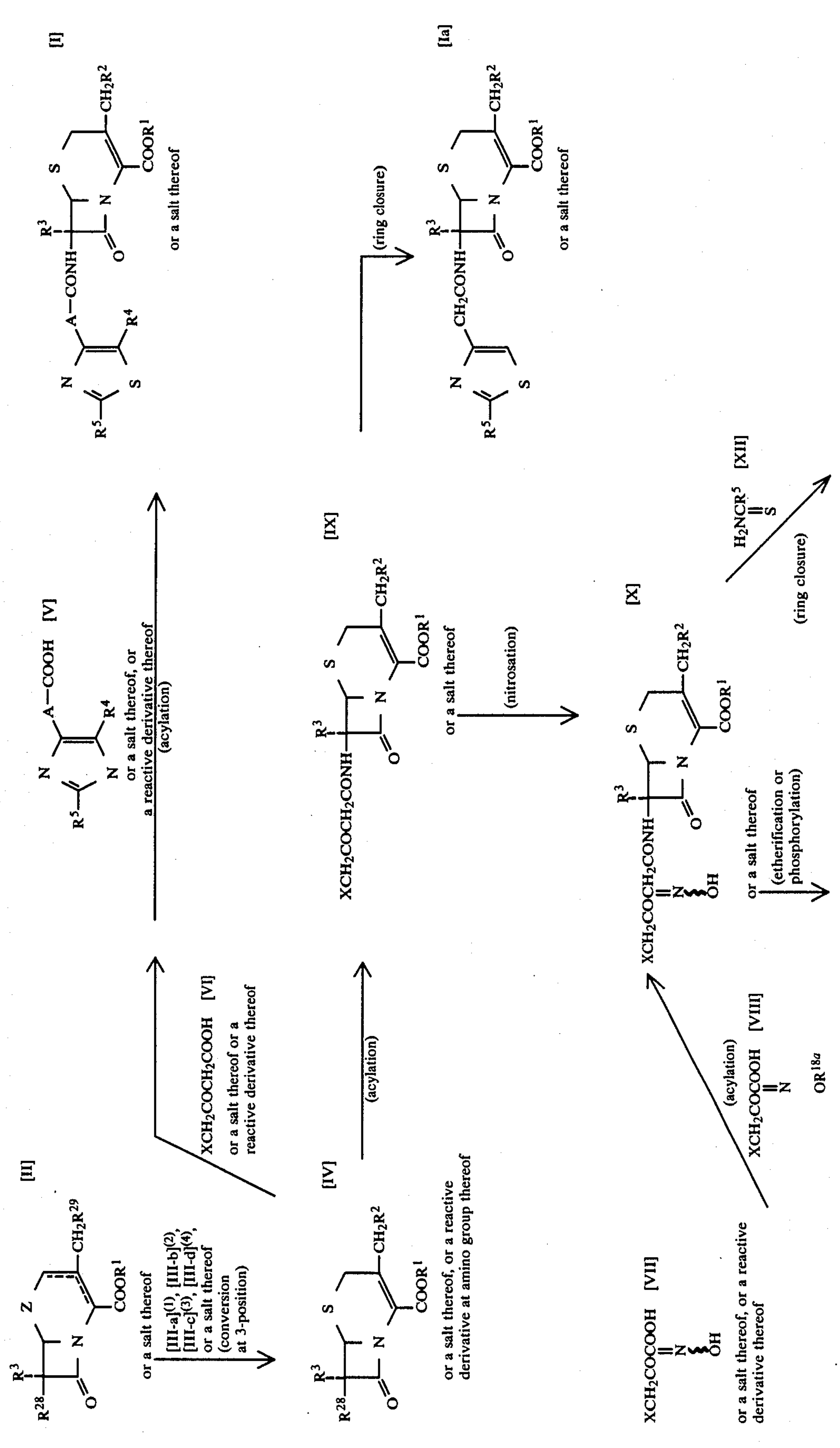

-continued
Production Route 1
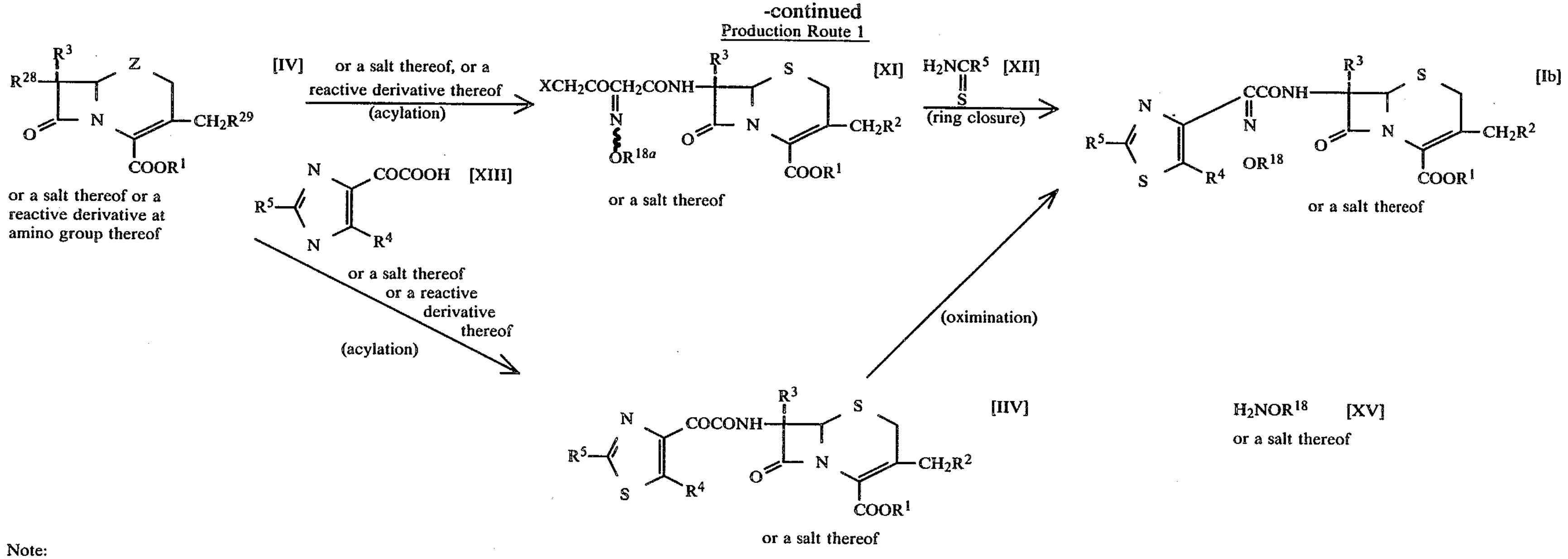
Note:
(1)Formula [III-a] is 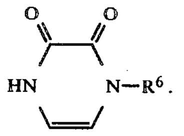
(2)Formula [III-b] is 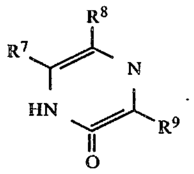
(3)Formula [III-c] is 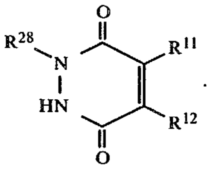
(4)Formula [III-d] is 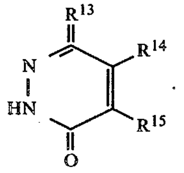

Production Route 2

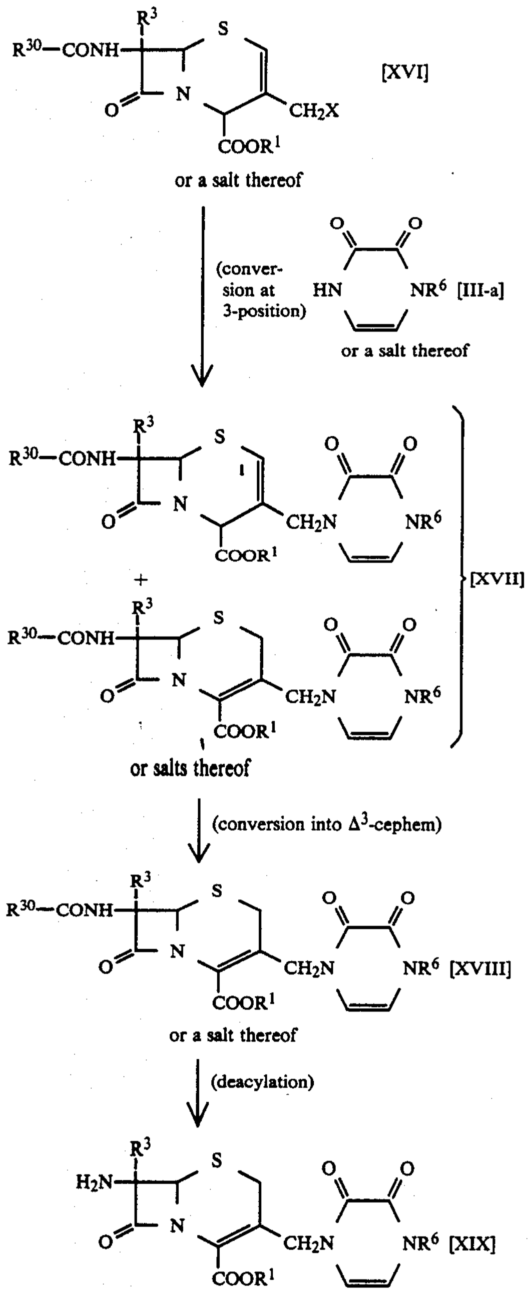

In the above formulas, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{18}$, A and the bond ∿∿ have the same meanings as defined above; $R^{18a}$ represents the groups for $R^{18}$ except a hydrogen atom; $R^{28}$ represents an amino group, or a group of the formula,

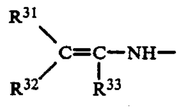

in which each of $R^{31}$, $R^{32}$ and $R^{33}$, which may be the same or different, represents a hydrogen atom or an organic residue not participating in the reaction, or a group of the formula,

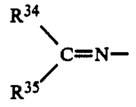

in which each of $R^{34}$ and $R^{35}$, which may be the same or different, represents a hydrogen atom or an organic residue not participating in the reaction; $R^{29}$ represents a substituted or unsubstituted acyloxy or carbamoyloxy group; $R^{30}$ represents benzyl, phenoxymethyl or a group of the formula,

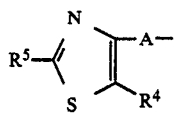

in which $R^4$, $R^5$ and A have the same meanings as defined above; X represents a halogen atom; >Z represents >S or >S→O; and the dotted line in the ring represents a double bond between the 2- and 3-positions or the 3- and 4-positions.

A further detailed explanation is made below. $R^{28}$ represents an amino group, a group of the formula,

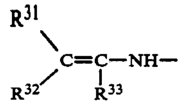

or a group of the formula,

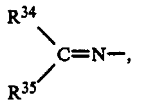

and the group of the formula,

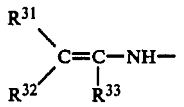

includes the group of the formula,

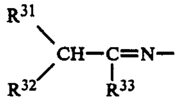

which is its isomer. The organic residues not participating in the reaction for $R^{31}$, $R^{32}$, $R^{33}$, $R^{34}$ and $R^{35}$ include those well-known in the art, specifically substituted or unsubstituted aliphatic residues, alicyclic residues, aromatic residues, aromatic-aliphatic residues, heterocyclic residues, acyl groups and the like. More specifically, the following groups are included:

(1) aliphatic residues: alkyl groups; alkenyl groups, (2) alicyclic residues: cycloalkyl groups; cycloalkenyl groups, (3) aromatic residues: aryl groups, (4) aromatic-aliphatic residues: aralkyl groups, (5) heterocyclic residues: heterocyclic groups, (6) acyl groups: acyl groups which can be derived from organic carboxylic acids which include aliphatic carboxylic acids, alicyclic carboxylic acids and alicycloaliphatic carboxylic acids; and also include aromatic aliphatic carboxylic acids, aromatic-oxyaliphatic carboxylic acids, aromatic-thioaliphatic carboxylic acids, heterocyclic aliphatic carboxylic acids, heterocyclicoxyaliphatic carboxylic acids, and heterocyclicthioaliphatic carboxylic acids, in which an aromatic residue or a heterocyclic group is bonded, directly or through an oxygen or sulfur atom, to an aliphatic carboxylic acid; organic carboxylic acids wherein an aromatic residue, an aliphatic group or an alicyclic group is bonded to the carbonyl group through an oxygen, nitrogen or sulfur atom; aromatic carboxylic acids; heterocyclic carboxylic acids; and the like.

The above aliphatic carboxylic acids include formic acid, acetic acid, propionic acid, butanoic acid, isobutanoic acid, pentanoic acid, methoxyacetic acid, methylthioacetic acid, acrylic acid, crotonic acid and the like, the above alicyclic carboxylic acids include cyclohexanoic acid and the like and the above alicycloaliphatic carboxylic acids include cyclopentaneacetic acid, cyclohexaneacetic acid, cyclohexanepropionic acid, cyclohexadieneacetic acid and the like.

Also, the aromatic residues in the above-mentioned organic carboxylic acids include phenyl, naphthyl and the like.

Each of the groups constituting these organic carboxylic acids may be further substituted by a substituent such as a halogen atom, a hydroxyl group, a protected hydroxyl group, an alkyl group, an alkoxy group, an acyl group, a nitro group, an amino group, a protected amino group, a carboxyl group, or a protected carboxyl group.

Also, the substituted or unsubstituted acyloxy and carbamoyloxy groups for $R^{29}$ include alkanoyloxy groups such as acetoxy, propionyloxy, butyryloxy and the like; alkenoyloxy groups such as acryloyloxy and the like; aroyloxy groups such as benzoyloxy, naphthoyloxy and the like; and carbamoyloxy group. These groups may be substituted by one or more substituents such as halogen atoms, nitro group, amino group, alkyl groups, alkoxy groups, alkylthio groups, acyloxy groups, acylamino groups, hydroxyl group, carboxyl group, sulfamoyl group, carbamoyl group, alkoxycarbonylcarbamoyl groups, aroylcarbamoyl groups, alkoxycarbonylsulfamoyl groups, aryl groups, carbamoyloxy group and the like.

In the above-mentioned substituents for $R^{29}$, hydroxyl group, amino group, carboxyl group and the like may be protected with protecting groups which are usually employed, and the protecting groups include, specifically the hydroxyl-protecting groups, amino-protecting groups and carboxyl-protecting groups which have been mentioned above as to $R^2$.

(a) Conversion reaction at 3-position 7-substituted or unsubstituted amino-3-substituted methyl cephem carboxylic acid of the formula [IV] or a salt thereof can be produced in a high yield with a high purity using an industrially easy procedure by reacting a 2,3-dioxo-1,2,3,4-tetrahydropyrazine of the formula III-α], α 2-oxo-1,2-dihydropyrazine of the formula [III-b], a 3,6-dioxo-1,2,3,6-tetrahydropyridazine of the formula [III-c], or a 6-oxo-1,6-dihydropyridazine of the formula [III-d], or a salt thereof with a cephalosporanic acid represented by the formula [II] or a salt thereof in the presence of an acid or a complex compound of an acid, then if desired, removing the protecting group, protecting the carboxyl group or converting the obtained compound to a salt thereof. Further, the above-mentioned 2,3-dioxo-1,2,3,4-tetrahydropyrazine can be prepared by the method described in the Journal of Chemical Society, Perkin I, pp. 1888–1890 (1975).

Furthermore, if necessary, the substituent on the amino group at the 7-position can be removed in a conventional manner to form a 7-unsubstituted amino compound. According to this procedure, not only $\Delta^3$-cephem compounds but also $\Delta^2$-cephem compounds can be used as the starting compounds, and where the $\Delta^2$-cephem compounds are used as the starting compounds, the reaction product $\Delta^2$-cephem compounds are further converted to $\Delta^3$-cephem compounds.

Also, not only compounds where $>Z$ is $>S$ but also compounds where $>Z$ is $>S\rightarrow O$ can be used as the starting materials, and in the latter case $>S\rightarrow O$ can be converted to $>S$ during the reaction or in an after-treatment step.

If the 2,3-dioxo-1,2,3,4-tetrahydropyrazine of the formula [III-a], the 2-oxo-1,2-dihydropyrazine of the formula [III-b], the 3,6-dioxo-1,2,3,6-tetrahydropyridazine of the formula [III-c] or the 6-oxo-1,6-dihydropyridazine of the formula [III-d] which is used as a reactant in the reaction, has basic or acidic group as the substituents, these compounds may, if necessary, be applied in the form of the corresponding salt to the reaction. In this case, the salts at the basic groups and the salts at the acidic groups include those mentioned as to the salts of the compounds of the formula [I].

Also, the salts of the compounds of the formulas [III] and [IV] include salts at the basic groups and at the acidic groups, and these salts include those mentioned about the salts of the compounds of the formula [I]. The salts of the compounds of the formula [II] may be previously isolated and then used, or may be prepared in situ.

As the acids or the complex compounds of acids used in the reaction, there are mentioned, for example, protonic acids, Lewis acids or complex compounds of Lewis acids. The protonic acids include sulfuric acids, sulfonic acids and super acids (super acids means acids stronger than 100% sulfuric acid and includes some of the above-mentioned sulfuric acids and sulfonic acids). More specifically, the protonic acids include sulfuric acids such as sulfuric acid, chlorosulfuric acid, fluorosulfuric acid and the like, sulfonic acids, for example, alkyl (mono- or di-)sulfonic acids such as methanesulfonic acid, trifluoromethanesulfonic acid and the like, aryl(mono-, di or tri-)sulfonic acids such as p-toluenesulfonic acid and the like, super acids, such as perchloric acid, magic acid ($FSO_3H$-$SbF_5$), $FSO_3H$-$AsF_5$, $CF_3SO_3H$-$SbF_5$, HF-$BF_3$, $H_2SO_4$-$SO_3$ and the like.

The Lewis acids include, for example, boron trifluoride, and the complex compounds of Lewis acids include complex compounds of boron trifluoride with dialkyl ethers such as diethyl ether, di-n-propyl ether, di-n-butyl ether and the like; with amines such as ethylamine, n-propylamine, n-butylamine, triethanolamine and the like; with esters such as ethyl formate, ethyl acetate and the like; with aliphatic acids such as acetic acid, propionic acid and the like; and with nitriles such as acetonitrile, propionitrile and the like.

The reaction is preferably conducted in the presence of an organic solvent. The organic solvents used include all organic solvents inert to the reaction, for example, nitroalkanes such as nitromethane, nitroethane, nitropropane and the like; organic carboxylic acids such as formic acid, acetic acid, trifluoroacetic acid, dichloroacetic acid, propionic acid and the like; ketones such as acetone, methyl ethyl ketone, methyl isobutyl ketone and the like; ethers such as diethyl ether, diisopropyl ether, dioxane, tetrahydrofuran, ethyleneglycol dimethyl ether, anisole, dimethyl Cellosolve and the like; esters such as ethyl formate, diethyl carbonate, methyl acetate, ethyl acetate, ethyl chloroacetate, butyl acetate and the like; nitriles such as acetonitrile, butyronitrile and the like; and sulfolanes such as sulfolane and the like. These solvents may be used in admixture of two or more. In addition, complex compounds formed from these organic solvents and Lewis acids can be used as the solvent. It is sufficient that the amount of the acid or the complex compound of the acid used is at least equimolar to the amount of the compound represented by the formula [II] or a salt thereof, and the amount may be varied depending on the respective cases. In particular, the use in a proportion of 2–10 moles per mole of the compound of the formula [II] or a salt thereof is preferred. Where the complex compound of the acid is used, it can be used per se as a solvent, and two or more of the complex compounds may be used in admixture.

It is sufficient that the amount of the 2,3-dioxo-1,2,3,4-tetrahydropyrazine of the formula [III-a], the 2-oxo-1,2-dihydropyrazine of the formula [III-b], the 3,6-dioxo-1,2,3,6-tetrahydropyridazine of the formula [III-c] or the 6-oxo-1,6-dihydropyridazine of the formula [III-d] or a salt thereof is at least equimolar to the amount of the compound represented by the formula [II] or a salt thereof, and particularly, the use in the amount of about 1.0–5.0 moles per mole is preferred.

This reaction is usually carried out at 0°–80° C., and completes in ten minutes to thirty hours. The presence of water in the reaction system may cause undesirable side reactions such as lactonization of the starting material or products and cleavage of β-lactam ring, so that is desirable to keep the system under the anhydrous conditions. In order to fulfill this requirement, it is sufficient to add, to the reaction system, a suitable dehydrating agent, for example, a phosphorus compound such as phosphorus pentoxide, polyphosphoric acid, phosphorus pentachloride, phosphorus trichloride, phosphorus oxychloride or the like; an organic silylating agent such as N,O-bis(trimethylsilyl)acetamide, trimethylsilylacetamide, trimethylchlorosilane, dimethyldichlorosilane or the like; an organic acid chloride such as acetyl chloride, p-toluenesulfonyl chloride or the like; an acid anhydride such as acetic anhydride, trifluoroacetic anhydride or the like; an inorganic dehydrating agent such as anhydrous magnesium sulfate, anhydrous calcium chloride, a molecular sieve, calcium carbide or the like.

If a compound represented by the formula [II] wherein $R^1$ represents a carboxyl-protecting group is used as the starting material, a compound represented by the formula [IV] wherein $R^1$ represents a hydrogen atom can, in some cases, be directly obtained by the reaction, or can be obtained by removing the protecting group in a conventional manner.

Next, conversion reaction at 3-position, which is described in Production Route 2, is explained.

The halogenated compound represented by the formula [XVI] can be prepared according to the method described in Tetrahedron Letters, No. 46, pp. 3991–3994 (1974) and Tetrahedron Letters No. 40, pp. 2915–3918 (1981).

The compound represented by the formula [XVII] or a salt thereof can be prepared by the reaction of a halogenated compound represented by the formula [XVI] or a salt thereof with a 2,3-dioxo-1,2,3,4-tetrahydropyrazine of the formula [III-a] or a salt thereof in the presence of a base. The base includes alkali metal carbonates (for example, sodium carbonate, potassium carbonate or the like); alkali metal hydrogencarbonates (for example, sodium hydrogencarbonate, potassium hydrogencarbonate and the like); alkali metal hydroxides (for example, sodium hydroxide, potassium hydroxide, and the like); nitrogen-containing organic bases, for example, triethylamine, pyridine, N,N-dimethylaniline and the like.

The conversion at 3-position is generally carried out in a suitable solvent. The solvent includes halogenated hydrocarbons such as chloroform, methylene chloride and the like; ethers such as tetrahydrofuran, dioxane and the like; N,N-dimethylformamide; N,N-dimethylacetamide; acetone; water; and mixtures thereof.

In this case, the compound represented by the formula [III-a] or a salt thereof is preferably used in an amount of about 1.0–2.0 moles per mole of the compound represented by the formula [XVI] or a salt thereof. The reaction is generally carried out at a temperature of 0–50° C. for 30 minutes to 10 hours.

The mixture of a $\Delta^2$- and $\Delta^3$-cephem compound thus obtained, that is, a compound represented by the formula [XVII] or a salt thereof, can be easily converted into the $\Delta^3$-cephem compound, to prepare the compound of the formula [XVIII] or a salt thereof, which is then converted into the compound of the formula [XIX] or a salt thereof by the deacylation. Said conversion reaction and deacylation are known in the fields of penicillins and cephalosporins and are specifically described in the Journal of Organic Chemistry, Vol. 35, No. 7, pp. 2430–2433 (1970) and "Cephalosporins and Penicillins" (by Flynn, Academic Press), pp. 56–64.

If the substituents of the 2,3-dioxo-1,2,3,4-tetrahydropyrazine of the formula [III-a], the 2-oxo-1,2-dihydropyrazine of the formula [III-b], the 3,6-dioxo-1,2,3,6-tetrahydropyridazine of the formula [III-c], or the 6-oxo-1,6-dihydropyridazine of the formula [III-d] or the salt thereof, which are used as the reactants in the reaction, are substituted by a hydroxyl group, an amino group, a carboxyl group or the like, these groups may be protected by the above-mentioned protecting groups prior to the reaction and subjected to a conventional removal reaction after the completion of the reaction to obtain a desired compound.

Also, the compound represented by the formula [IV] or [XIX] can, if necessary, be protected at the carboxyl group or converted into the salt according to a conventional method, to obtain the objective compound. Also, the compound represented by the formula [IV] wherein $R^{28}$ represents an amino group can be converted into a reactive derivative at the amino group or the compound represented by the formula [XIX] as mentioned hereinafter by a conventional method.

(b) Acylation

When the compound represented by the formula [V], [VI], [VII], [VIII] or [XIII], or a salt thereof, or a reactive derivative thereof is reacted with a compound represented by the formula [IV] or a salt thereof or a reactive derivative at the amino group, a compound represented by the formula [I], [IX], [X], [XI] or [XIV], or a salt thereof is obtained.

The salts of the compound represented by the formula [V], [VI], [VII], [VIII] or [XIII] include salts at the basic group or the acidic group, which specifically include those mentioned as to the salts of the compound represented by the formula [I].

The reactive derivatives at the amino group of the compound represented by the formula [IV] include all derivatives which are often used in acylation, for example, an isocyanate; a Schiff base produced by the reaction of the compound represented by the formula [IV] or a salt thereof with a carbonyl compound such as an aldehyde, a ketone, or the like (ketimine type or its isomer, namely, enamine type); a silyl derivative, a phosphorus derivative or a tin derivative, produced by the reaction of a compound represented by the formula [IV] or a salt thereof with a silyl compound such as bis(trimethylsilyl)acetamide, trimethylsilylacetamide, trimethylsilyl chloride, or the like, a phosphorus compound such as phosphorus trichloride,

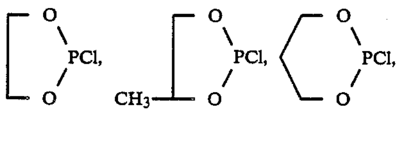

$(CH_3CH_2O)_2PCl$, $(CH_3CH_2)_2PCl$ or the like, or a tin compound such as $(C_4H_9)_3SnCl$ or the like.

The reactive derivatives of the compounds represented by the formulas [V], [VI], [VII], [VIII] and [XIII] include specifically acid halides, acid anhydrides, mixed acid anhydrides, active acid amides, active esters, reactive derivatives obtained by reaction of the compounds represented by the formulas [V], [VI], [VII], [VIII] and [XIII] with a Vilsmeier reagent. The mixed acid anhydride includes a mixed acid anhydride with a monoalkyl carbonate such as monoethyl carbonate, monoisobutyl carbonate and the like, a mixed acid anhydride with a lower alkanoic acid which may be substituted by a halogen, such as pivalic acid, trichloroacetic acid or the like. The active acid amide includes N-acylsaccharin, N-acylimidazole, N-acylbenzoylamide, N,N'-dicyclohexyl-N-acylurea, N-acylsulfonamide and the like. The active ester includes cyanomethyl ester, substituted phenyl esters, substituted benzyl esters, substituted thienyl esters and the like.

The reactive derivatives obtained by reaction with a Vilsmeier reagent include those obtained by reaction with a Vilsmeier reagent obtained by reacting an acid amide such as N,N-dimethylformamide, N,N-dimethylacetamide or the like with a halogenating agent such as phosgene, thionyl chloride, phosphorus trichloride, phosphorus tribromide, phosphorus oxychloride, phosphorus pentachloride, trichloromethyl chloroformate, oxalyl chloride or the like.

If each of the compounds represented by the formulas [V], [VI], [VII], [VIII] and [XIII] is used in the form of a free acid or a salt, a suitable condensing agent is used. The condensing agent includes N,N'-disubstituted carbodiimides such as N,N'-dicyclohexylcarbodiimide; azolide compounds such as N,N'-thionyldiimidazole; dehydrating agents such as N-ethoxycarbonyl-2-ethoxy-1,2-dihydroquinoline, phosphorus oxychloride, alkoxyacetylenes and the like; 2-halogenopyridinium salts such as 2-chloropyridiniummethyl iodide and 2-fluoropyridiniummethyl iodide; and the like.

This acylation reaction is usually carried out in a suitable solvent in the presence or absence of a base. As the solvent, there may be used a solvent inert to the reaction, for example, a halogenated hydrocarbon such as chloroform, methylene chloride or the like; an ether such as tetrahydrofuran, dioxane or the like; N,N-dimethylformamide; N,N-dimethylacetamide; acetone; water; or a mixture thereof. As the base, there may be used an inorganic base such as an alkali metal hydroxide, an alkali metal hydrogencarbonate, an alkali metal carbonate, an alkali metal acetate or the like; a tertiary amine such as trimethylamine, triethylamine, tributylamine, pyridine, N-methylpiperidine, N-methylmorpholine, lutidine, collidine or the like; or a secondary amine such as dicyclohexylamine, diethylamine or the like.

The compound represented by the formula [IX] or a salt thereof which can be converted into the compound represented by the formulas [Ia] or [Ib] or a salt thereof can be produced by the following procedure:

In order to obtain the compound represented by the formula [IX] or a salt thereof using the compound represented by the formula [IV] or a salt thereof, a 4-halogeno-3-oxo-butyryl halide which is obtained by the reaction of diketene with a halogen such as chlorine or bromine [Journal of the Chemical Society, 97, 1987 (1910)] may be reacted with the compound represented by the formula [IV] or a salt thereof according to a usual method. Reaction conditions and procedures which are known in the art can be applied to this reaction. And the salt of the compound represented by the formula [IX] can easily be prepared according to a usual method, and the salt includes the same salts as mentioned above as to the salts of the compound represented by the formula [I]. Although the compound represented by the formula [IX] or a salt thereof may be isolated and purified, it can be used for the subsequent reaction without isolation.

In addition, the compound represented by the formura [V], [VI], [VII], [VIII] or [XIII] or a salt thereof or a reactive derivative thereof is preferably used in an amount of about one mole to several moles per mole of the compound represented by the formula [IV] or a salt thereof or its reactive derivative at the amino group. The reaction is usually carried out at a temperature ranging from −50° to 40° C. The reaction time is usually 10 minutes to 48 hours.

Furthermore, the compounds represented by the formulas [I], [IX], [X], [XI] and [XIV] wherein $R^1$ is a carboxyl-protecting group can be converted to the compounds represented by the formulas [I], [IX], [X], [XI] and [XIV] wherein $R^1$ is a hydrogen atom, or their salts according to the usual method; and similarly the compounds represented by the general formulas [I], [IX], [X], [XI] and [XIV] wherein $R^1$ is a hydrogen atom can be converted to the compounds represented by the formulas [I], [IX], [X], [XI] and [XIV] wherein $R^1$ is a carboxyl-protecting group or salts thereof; and the salts of the compounds represented by the formulas [I], [IX], [X], [XI] and [XIV] can be converted to the corresponding free acid forms, respectively.

Also, in this acylation reaction, if $R^1$, $R^2$ and $R^5$ contain groups active to the reaction, these groups can suitably be protected with conventional protecting groups prior to the reaction, and the protecting groups can also be removed by a usual method after the reaction.

The compound represented by the formula [I] or a salt thereof of this invention obtained by the above-mentioned method can be isolated by a conventional method.

(c) Nitrosation

Subsequently, in order to obtain the compound represented by the formula [X] or a salt thereof from the compound represented by the formula [IX] or a salt thereof, a nitrosating agent is reacted with the compound represented by the formula [IX] or a salt thereof. The reaction is usually carried out in a solvent, and as the solvent, there may be used a solvent inert to the reaction such as water, acetic acid, benzene, methanol, ethanol, tetrahydrofuran or the like. Preferable examples of the nitrosating agent include nitric acid and derivatives thereof, for example, nitrosyl halides such as nitrosyl chloride, nitrosyl bromide and the like, alkali metal nitrites such as sodium nitrite, potassium nitrite and the like, alkyl nitrites such as butyl nitrite, pentyl nitrite and the like. If a nitrous acid salt is used as the nitrosating agent, it is preferable to carry out the reaction in the presence of an inorganic or organic acid such as hydrochloric acid, sulfuric acid, formic acid, acetic acid or the like. If an alkyl nitrite is used as the nitrosating agent, it is preferable to carry out the reaction in the presence of a strong base such as an alkali metal alkoxide or the like. The reaction is usually carried out at a temperature ranging from −15° to 30° C., and the reaction time is usually 10 minutes to 10 hours. The salt of the compound represented by the formula [X] can easily be prepared according to a usual method, and the salt includes the same salts as mentioned above as to the salts of the compound represented by the formula [I]. Although the compound represented by the formula [X] or a salt thereof thus obtained can be isolated and purified by a well-known method, it can be used for the subsequent reaction without isolation.

(d) Etherification and phosphorylation

In order to obtain the compound represented by the formula [XI] or a salt thereof from the compound represented by the formula [X] or a salt thereof, the compound represented by the formula [X] or a salt thereof is subjected to etherification reaction or phosphorylation reaction.

The etherification reaction and the phosphorylation reaction can be carried out by a usual method such as described in Japanese Patent Application Kokai (Laid-Open) Nos. 137,988/78, 105,689/80, 149,295/80 and the like.

For example, alkylation can be carried out according to a usual method. The reaction is generally carried out at a temperature of −20° to 60° C. and completes in 5 minutes to 10 hours.

As the solvent, there may be used a solvent inert to the reaction, for example, tetrahydrofuran, dioxane, methanol, ethanol, chloroform, methylene chloride, ethyl acetate, butyl acetate, N,N-dimethylformamide, N,N-dimethylacetamide, water, or a mixture thereof.

As the alkylating agent, there may be used, for example, a lower alkyl halide such as methyl iodide, methyl bromide, ethyl iodide, ethyl bromide or the like, dimethyl sulfate, diethyl sulfate, diazomethane, diazoethane, methyl p-toluenesulfonate or the like. If an alkylating agent other than diazomethane and diazoethane is used, the reaction is carried out in the presence of an alkali metal carbonate such as sodium carbonate, potassium carbonate or the like; an alkali metal hydroxide such as sodium hydroxide, potassium hydroxide or the like; or an organic base such as triethylamine, pyridine, N,N-dimethylaniline or the like.

Also, the salt of the compound represented by the formula [XI] can easily be obtained according to a usual method, and the salt includes the same salts as mentioned above as to the salts of the compound represented by the formula [I].

In addition, a protecting group can be introduced and removed according to a usual method, whereby a compound can be changed into a corresponding objective compound.

Although the compound represented by the formula [XI] or a salt thereof thus obtained may be isolated and purified by a usual method, they can be used for the subsequent reaction without isolation.

(e) Ring closure reaction

The compound represented by the formula [Ia] or [Ib] or a salt thereof of this invention can be obtained by the reaction of the compound represented by the formula [IX], [X] or [XI] or a salt thereof with the thioformamide or thiourea represented by the formula [XII]. This reaction is usually carried out in a solvent. As the solvent, there may be used a solvent inert to the reaction, for example, water, methanol, ethanol, acetone, tetrahydrofuran, dioxane, N,N-dimethylformamide, N,N-dimethylacetamide, N-methylpyridone, alone or in admixture of two or more. Although it is not essential to add an acid-removing agent, the reaction sometimes proceeds smoothly by adding an acid-removing agent in such an amount that the cephalosporin skeleton will not be influenced. The acid-removing agent used for the reaction includes inorganic and organic bases such as alkali metal hydroxides, alkali metal hydrogencarbonates, triethylamine, pyridine, and the like. The reaction is usually carried out at a temperature of 0°-100° C. Thioformamide or thiourea is usually used in an amount of about one mole to several moles per mole of the compound represented by the formula [IX], [X] or [XI] or a salt thereof. The reaction time is 1-48 hours, preferably 1-10 hours. Furthermore, in the compound represented by the formula [Ia] or [Ib], the protection of the carboxyl group and removal of the carboxyl protecting group or conversion of the product to a salt can be carried out according to a usual method to convert the compound to the corresponding objective compound. If $R^1$, $R^2$, and $R^5$ in the formula [Ia] or [Ib] contain groups active to the reaction, these groups can be suitably protected by a conventional protecting group prior to the reaction and the protecting group can be removed by a usual method after the reaction. The objective compound represented by the formula [Ia] or [Ib] or its salt thus obtained can be isolated by a usual method.

(f) Oximination

The compound represented by the formula [Ib] or a salt thereof is obtained by reacting the compound represented by the formula [XIV] or a salt thereof with the compound represented by the formula [XV] or a salt thereof. The salt of the compound represented by the formula [XV] includes hydrochlorides, hydrobromides, sulfates and the like. This reaction is usually carried out not only in a solvent such as water, an alcohol, N,N-dimethylacetamide or the like but also in other solvents inert to the reaction or a mixed solvent thereof. The reaction is carried out at a temperature of 0° to 100° C., preferably in a range of 10° to 50° C. The reaction time is usually 10 minutes to 48 hours. The compound represented by the formula [XV] or a salt thereof is used in an amount of about one mole to several moles per mole of the compound represented by the formula [XIV] or a salt thereof. Although the salt of the compound represented by the formula [XV] can be used per se for the reaction, it can also be reacted in the presence of a base, for example, an inorganic base such as an alkali metal hydroxide (for example, sodium hydroxide, potassium hydroxide or the like), an alkaline earth metal hydroxide (for example, magnesium hydroxide, calcium hydroxide or the like), an alkali metal carbonate (for example, sodium carbonate, potassium carbonate or the like), an alkaline earth metal carbonate (for example, magnesium carbonate, calcium carbonate or the like), an alkali metal hydrogencarbonate (for example, sodium hydrogencarbonate, potassium hydrogencarbonate or the like), an alkaline earth metal phosphate (for example, magnesium phosphate, calcium phosphate or the like), an alkali metal hydrogenphosphate (for example, disodium hydrogenphosphate, dipotassium hydrogenphosphate) or an alkali metal acetate (for example, sodium acetate, potassium acetate), an organic base such as a trialkylamine (for example, trimethylamine, triethylamine, or the like), picoline, N-methylpyrrolidine, N-methylmorpholine, 1,5-diazabicyclo[4,3,0]-5-nonene, 1,4-diazabicyclo[2,2,2]octane, 1,5-diazabicyclo[5,4,0]-7-undecene or the like. The compound represented by the formula [Ib] or a salt thereof of this invention thus obtained can undergo conversion of $R^1$ in a conventional manner, and can also be isolated by a usual method.

(g) Alkoxylation

The compound represented by the formula [IV] wherein $R^3$ is an alkoxy group can be synthesized from the compound represented by the formula [IV] wherein $R^3$ is a hydrogen atom by a method known per se, for example, the method described in the Journal of Synthetic Organic Chemistry, Japan, 35, (7), 563-574 (1977).

Furthermore, the compound represented by the formulas [I], [Ia], [Ib], [IX], [X], [XI] and [XIV] wherein $R^3$ is an alkoxy group can be synthesized from the respective compound represented by the formula [I], [Ia], [Ib], [IX], [X], [XI] or [XIV] wherein $R^3$ is a hydrogen atom in a manner known per se, for example, the method described in Japanese Patent Application Kokai (Laid-Open) Nos. 24,888/79 and 103,889/79.

The compound represented by the formula [I] or a salt thereof thus obtained can be administered to human beings and animals in the form of a free acid or in the form of a pharmaceutically acceptable salt or ester for the purpose of the treatment of and protection against bacterial infections. It is preferable to parenterally administer the compound in the form of a free acid or a pharmaceutically acceptable salt or orally administer the compound in the form of a pharmaceutically acceptable ester. In that case, it is sufficient that the compound is formed into a dosage form usually used in cephalosporin medicines, for example, tablet, capsule, powder, fine granule, granule, syrup, injection (including drip), suppository or the like. When the above-mentioned medicine is formed into a dosage form, there may be used diluents and/or additives, for example, vehicles such as starch, lactose, sugar, calcium phosphate, calcium carbonate or the like; bonding agents such as gum arabic, starch, microcrystalline cellulose, carboxymethyl cellulose, hydroxypropyl cellulose or the like; lubricants such as talc, magnesium stearate or the like; disintegrating agents such as carboxymethyl calcium, talc or the like.

When the compound represented by the formula [I] or a salt thereof is administered, the dosage, the administration time and the administration method can be varied depending on the symptoms of patient, and generally it is sufficient to administer orally or parenterally to an adult in a dose of about 50-5000 mg in 1 to 4 portions a day.

This invention is explained below with reference to Referential Examples and Examples which are merely by way of illustration and not by way of limitation.

REFERENTIAL EXAMPLE 1

(1) To a solution of 20.0 g of ethyl N-(2,2-diethoxyethyl)oxamate in 60 ml of ethanol was added 6.1 ml of 70% by weight aqueous ethylamine solution, and the mixture was subjected to reaction at room temperature for 1 hour. After the completion of the reaction, the precipitated crystals were collected by filtration and recrystallized from ethanol to obtain 17.0 g (yield: 85.1%) of N-ethyl-N'-(2,2-diethoxyethyl)oxamide having a melting point of 131°-132° C.

IR (KBr) $cm^{-1}$: $\nu_{C=O}$ 1650.

In a similar manner, the compounds shown in Table 3 were obtained.

TABLE 3

$(CH_3CH_2O)_2CHCH_2NHCOCONHR^6$

| Compound $R^6$ | Solvent for recrystallization | m.p. (°C.) | IR (KBr) $cm^{-1}$: $\nu_{C=O}$ |
|---|---|---|---|
| $-H$ | Ethyl acetate | 141-142 | 1650, 1635 |
| $-CH_3$ | Ethanol | 135-136 | 1645 |
| $-(CH_2)_2CH_3$ | Acetone | 84-85 | 1645 |
| 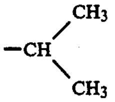 | Acetone n-Hexane | 145-146 | 1650, 1635 |
| $-(CH_2)_3CH_3$ | n-Hexane | 111-112 | 1645 |
| $-(CH_2)_4CH_3$ | n-Hexane | 92-93 | 1650 |
| $-(CH_2)_5CH_3$ | n-Hexane | 87-88 | 1650 |
| $-(CH_2)_7CH_3$ | n-Hexane | 110-111 | 1645 |
| $-(CH_2)_{11}CH_3$ | n-Hexane | 83-84 | 1645 |
| 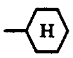 | Ethanol | 154-155 | 1640 |
| 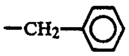 | n-Hexane | 113-114 | 1655 |
| $-CH_2CH_2OH$ | Ethanol | 118-119 | — |
| 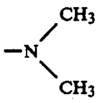 | Ethanol | 157-158 | 1645 |
| 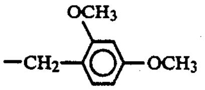 | — | 128-129 | 1655 |

(2) To a solution of the 17.0 g of N-ethyl-N'-(2,2-diethoxyethyl)oxamide obtained in above (1) in 85 ml of acetic acid was added 0.05 ml of concentrated hydrochloric acid. The mixture was refluxed for 30 minutes. After completion of the reaction, the solvent was removed by distillation under reduced pressure, and 70 ml of acetone was added to the residue, and crystals were collected by filtration. The crystals were recrystallized from methanol to obtain 6.8 g (yield: 61.8%) of 4-ethyl-2,3-dioxo-1,2,3,4-tetrahydropyrazine having a melting point of 173°-174° C.

IR (KBr) $cm^{-1}$: $\nu_{C=O}$ 1680-1620.

In a similar manner, the compounds shown in Table 4 were obtained.

TABLE 4

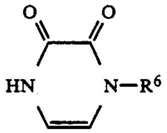

| Compound $R^6$ | Solvent for recrystallization | m.p. (°C.) | IR (KBr) $cm^{-1}$: $\nu_{C=O}$ |
|---|---|---|---|
| $-H$ | — | >280 | 1680-1640 |
| $-CH_3$ | Ethanol | 220-231 | 1690-1635 |
| $-(CH_2)_2CH_3$ | Acetone | 182-183 | 1680-1640 |
| 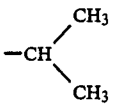 | Acetone | 215-219 | 1680, 1625 |
| $-(CH_2)_3CH_3$ | Acetone | 149-150 | 1680, 1640 |
| $-(CH_2)_4CH_3$ | Acetone | 171-172 | 1685, 1660, 1620 |
| $-(CH_2)_5CH_3$ | Acetone | 141-142 | 1685, 1660, 1620 |
| $-(CH_2)_7CH_3$ | Acetone | 145-146 | 1670, 1635 |
| $-(CH_2)_{11}CH_3$ | Ethanol | 145-146 | 1660, 1625 |
| 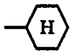 | Acetone | 254-255 | 1670, 1635 |
| 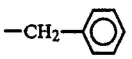 | Acetic acid | 225 | 1665, 1635 |
| $-CH_2CH_2OCOCH_3$ | Methanol | 178-180 | 1720, 1675, 1625 |
| 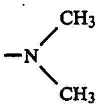 | Ethanol | 229-230 | 1700-1625 |
| 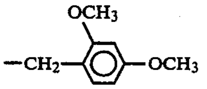 | — | 175-176 | 1740-1620 |

(3) To a suspension of 5.2 g of the 4-(2,4-dimethoxybenzyl)-2,3-dioxo-1,2,3,4-tetrahydropyrazine obtained in above (2) in 26 ml of N,N-dimethylformamide was added 4.1 g of potassium carbonate, and the mixture was stirred at room temperature for 30 minutes. Subsequently, 5.8 g of 4-bromomethyl-5-methyl-1,3-dioxol-2-one was added thereto, and the mixture was subjected to reaction at 50°-60° C. for 3 hours. The reaction mixture was introduced into a mixed solvent of 200 ml of ethyl acetate and 200 ml of water, after which the organic layer was separated, washed with 100 ml of water and dried over anhydrous magnesium sulfate. The solvent was removed by distillation under reduced pressure, and the residue was purified by a column chromatography (Wako Silica Gel C-200, eluent; chloroform) to obtain 4.9 g (yield, 66.0%, of 1-(2,4-dimethoxybenzyl)-4-(5-methyl-2-oxo-1,3-dioxol-4-yl)methyl-2,3-dioxo-1,2,3,4-tetrahydropyrazine having a melting point of 154°-156° C.

IR (KBr) $cm^{-1}$: $\nu_{C=O}$ 1820, 1675, 1630.

In a similar manner, the compounds shown in Table 5 were obtained.

TABLE 5

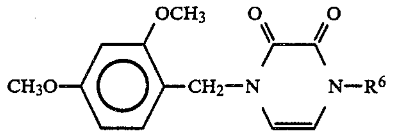

| Compound $R^6$ | m.p. (°C.) | IR (KBr) $cm^{-1}$: $\nu_{C=O}$ |
|---|---|---|
| 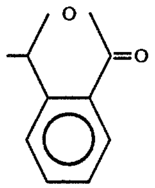 | 188-190 | 1775, 1700, 1650 |
| $-CH_2OCOC(CH_3)_3$ | 100-101 | 1750, 1690, 1660, 1640 |
| $-CH_2COOC(CH_3)_3$ | 105-106 | 1740, 1690, 1650 |

(4) In a mixed solvent of 37 ml of trifluoroacetic acid and 10.8 g of anisole was dissolved 3.7 g of 1-(2,4-dimethoxybenzyl)-4-(5-methyl-2-oxo-1,3-dioxol-4-yl)methyl-2,3-dioxo-1,2,3,4-tetrahydropyrazine obtained in above (3) and the mixture was reacted at 50° C. to 60° C. for 2 hours. Subsequently, the solvent was removed by distillation under reduced pressure. To the residue was added 30 ml of diethyl ether and crystals were collected by filtration to obtain 2.0 g (yield, 90.9%) of 4-(5-methyl-2-oxo-1,3-dioxol-4-yl)methyl-2,3-dioxo-1,2,3,4-tetrahydropyrazine having a melting point of 225°-226° C.

IR (KBr) $cm^{-1}$: $\nu_{C=O}$ 1825, 1805, 1725, 1690, 1670.

In a similar manner, the compounds shown in Table 6 were obtained.

TABLE 6

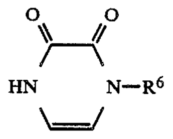

| Compound $R^6$ | m.p.(°C.) | IR(KBr)$cm^{-1}$: $\nu_{C=O}$ |
|---|---|---|
| 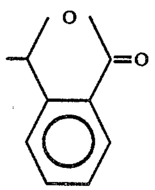 | >270 | 1790, 1775, 1730, 1690 |
| $-CH_2OCOC(CH_3)_3$ | 166-167 | 1740, 1700, 1660 |
| $-CH_2COOH$ | 282(decomp.) | 1730, 1670-1630 |

(5) To a solution of 2.6 g of 1-carboxymethyl-2,3-dioxo-1,2,3,4-tetrahydropyrazine in 13 ml of N,N-dimethylacetamide was added 3.9 g of diphenyldiazomethane at room temperature, and the mixture was subjected to reaction for for 10 minutes. The reaction mixture was introduced into a mixed solvent of 25 ml of ethyl acetate and 25 ml of water, and the mixture was stirred for 15 minutes. Precipitated crystals were collected by filtration, and washed with 10 ml of ethyl acetate and 10 ml of diethyl ether in this order to obtain 2.9 g (yield, 80.4%) of 1-diphenylmethyloxycarbonylmethyl-2,3-dioxo-1,2,3,4-tetrahydropyrazine having a melting point of 97°-98° C.

IR(KBr)$cm^{-1}$: $\nu_{C=O}$ 1750, 1675, 1645.

EXAMPLE 1

(1) To a solution of 10 ml of ethyl acetate containing 2.71 g of boron trifluoride were added 2.72 g of 7-aminocephalosporanic acid (hereinafter referred to as 7-ACA) and 1.54 g of 4-ethyl-2,3-dioxo-1,2,3,4-tetrahydropyrazine, and the mixture was subjected to reaction at room temperature for 16 hours. After completion of the reaction, the reaction mixture was introduced into 50 ml of methanol with cooling, and then 3.16 g of pyridine was added dropwise thereto. Precipitated crystals were collected by filtration, washed sufficiently with 30 ml of methanol, and thereafter dried to obtain 3.10 g (yield, 88.1%) of 7-amino-3-{[1-(4-ethyl-2,3-dioxo-1,2,3,4-tetrahydropyrazinyl)]methyl}-$\Delta^3$-cephem-4-carboxylic acid having a metling point of 191°-195° C. (decomp.).

IR(KBr)$cm^{-1}$: $\nu_{C=O}$ 1795, 1670, 1620.

NMR ($CF_3COOD$) $\delta$ values: 1.44 (3H, t, J=7 Hz, $>NCH_2C\underline{H_3}$), 3.69 (2H, bs, $C_2$—H), 4.08 (2H, q, J=7 Hz, $>NC\underline{H_2}CH_3$), 5.14, 5.51 (2H, ABq, J=15 Hz,

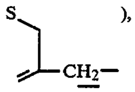
), 5.48 (2H, s, $C_6$—H, $C_7$—H), 6.74, 7.00 (2H, ABq, J-6 Hz,

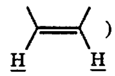
)

(2) The conversion reaction at 3-position mentioned in above (1) was carried out under the reaction conditions shown in Table 7 to obtain 7-amino-3-{[1-(4-ethyl-2,3-dioxo-1,2,3,4-tetrahydropyrazinyl)]methyl}-$\Delta^3$-cephem-4-carboxylic acid in the yields shown in Table 7.

TABLE 7

| No. | Starting material: 7-ACA | Starting material: 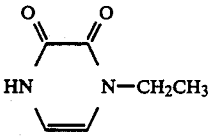 | Solvent | Acid or complex compound of acid | Reaction conditions | Amount (Yield) |
|---|---|---|---|---|---|---|
| 1 | 2.72 g | 1.54 g | Sulfolane 10 ml | Boron trifluoride 2.71 g | Room temperature 2 hours | 2.6 g (73.9%) |
| 2 | 2.72 g | 1.54 g | Nitromethane 14 ml | Boron trifluoride-diethyl ether complex 5.7 g | Room temperature 16 hours | 2.85 g (81.0%) |

(3) In a similar manner to that in above (1), the compounds shown in Table 8 were obtained. (In this case, the objective compounds were obtained by pouring into ice-water the reaction mixture after completion of the conversion at 3-position and adjusting to pH 3.5 with 28% by weight aqueous ammonia solution with ice-cooling.)

TABLE 8

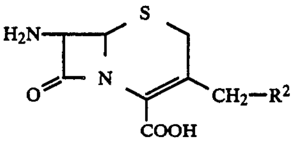

| No. | Compound $R^2$ | m.p. (°C.) | IR (KBr) $cm^{-1}$: $\nu_{C=O}$ | NMR ($d_6$-DMSO) δ values: |
|---|---|---|---|---|
| 1 | 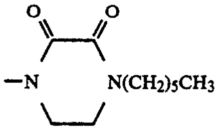 | 189.5-191.0 (decomp.) | 1800, 1680~1620 | 0.87 (3H, t, J=6Hz, >N(CH2)5CH3), 1.05-1.49 (8H, m, >NCH2(CH2)4CH3), 3.44 (2H, bs, $C_2$—H), 3.55-3.88 (2H, m, >NCH2(CH2)4CH3), 4.44, 5.05 (2H, ABq, J=15Hz, 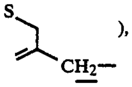 ), 4.88 (1H, d, J=5Hz, $C_6$—H), 5.06 (1H, d, J=5Hz, $C_7$—H), 6.71 (2H, s, 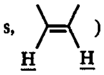 ) |
| 2 | 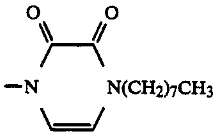 | 191.5-192.5 (decomp.) | 1800, 1680~1620 | 0.87 (3H, t, J=6Hz, >N(CH2)7CH3), 1.03-1.50 (12H, m, >NCH2(CH2)6CH3), 3.40 (2H, bs, $C_2$—H), 3.52-3.86 (2H, m, >NCH2(CH2)6CH3), 4.43, 5.04 (2H, ABq, J=15Hz, 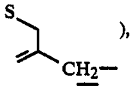 ), 4.86 (1H, d, J=6Hz, $C_6$—H), 5.04 (1H, d, J=6Hz, $C_7$—H), 6.69 (2H, |

TABLE 8-continued

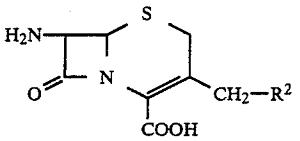

| No. | Compound $R^2$ | m.p. (°C.) | IR (KBr) $cm^{-1}$: $\nu_{C=O}$ | NMR ($d_6$-DMSO) δ values: |
|---|---|---|---|---|
| | | | | s, 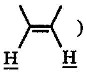 ) |
| 3 | 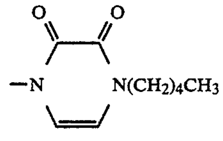 | 196–199 (decomp.) | 1800, 1678, 1630 | 0.91 (3H, t, J=7Hz, $N(CH_2)_4CH_3$), 1.10–1.95 (6H, m, $NCH_2(CH_2)_3CH_3$), 3.63 (2H, bs, $C_2$—H), 3.77 (2H, t, J=7Hz, $NCH_2(CH_2)_3CH_3$), 4.34, 4.82 (2H, ABq, J=15Hz, 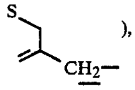 ), 5.32 (2H, bs, $C_6$—H, $C_7$—H), 6.76 (2H, bs, 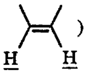 ) |
| 4 | 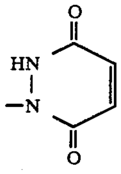 | >200 | 1790, 1655, 1630, 1600 | 3.72 (2H, bs, $C_2$—H), 5.41, 5.72 (2H, ABq, J=15Hz, 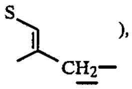 ), 5.47 (2H, s, $C_6$—H, $C_7$—H), 1.58 (2H, s, 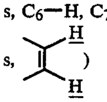 ) Measured in $CF_3COOH$ |

(4) The conversion reaction at 3-position mentioned in above (1) was carried out under the reaction conditions shown in Table 9 to obtain 7-amino-3-{[1-(3,6-dioxo-1,2,3,6-tetrahydropyridazinyl)]methyl}-$\Delta^3$-cephem-4-carboxylic acid in the yields shown in Table 9.

TABLE 9

| No. | Starting material 7-ACA | Starting material Maleic hydrazide | Solvent | Acid or complex compound of acid | Reaction conditions | Amount (Yield) |
|---|---|---|---|---|---|---|
| 1 | 2.0 g | 0.91 g | Trifluoroacetic acid 10 ml | Boron trifluoride-diethyl ether complex 4.17 g | Room temperature 16 hours | 1.72 g (72.3%) |
| 2 | 2.72 g | 1.23 g | Sulfolane 10 ml | Boron trifluoride 2.71 g | Room temperature 3 hours | 2.75 g (84.9%) |

(5) In a similar manner to that in above (1), the crude crystals shown in Table 10 were obtained.

TABLE 10

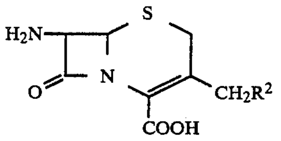

| No. | Compound $R^2$ |
|---|---|
| 1 | 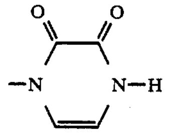 *1 |
| 2 | 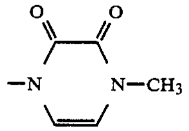 |

TABLE 10-continued

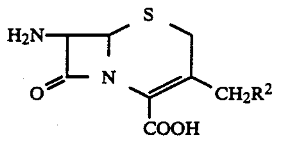

| No. | Compound $R^2$ |
|---|---|
| 3 | 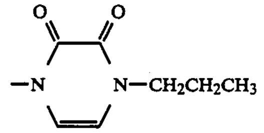 |
| 4 | 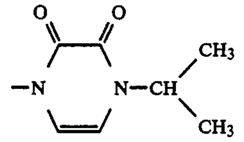 |
| 5 | 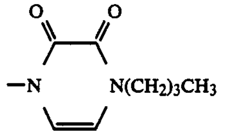 |
| 6 | 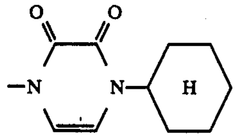 |
| 7 | 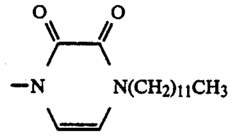 |
| 8 | 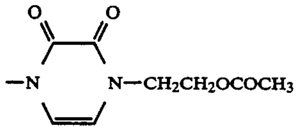 |
| 9 | 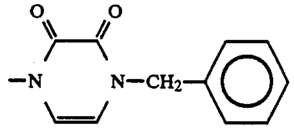 |
| 10 | 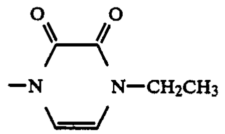 |
| 11 | 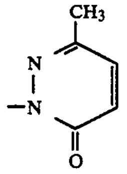 |

TABLE 10-continued

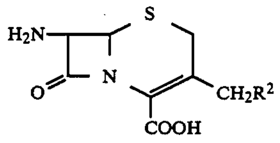

| No. | Compound $R^2$ |
|---|---|
| 12 | 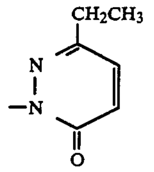 |
| 13 | 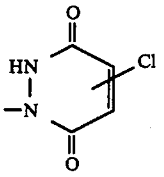 *2 |
| 14 | 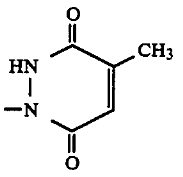 + 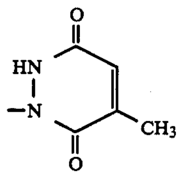 *3 |
| 15 | 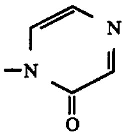 |
| 16 | 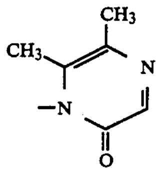 |

Note: The compounds in Nos. 10, 11, 12, 13, 14 and 15 were obtained by the reaction using sulfolane as a solvent.
*1: This compound was obtained by the procedure of introduction into methanol, filtration of insolubles and addition of pyridine into the filtrate.
*2: The representation was taken because it was not confirmed whether the chlorine atom was placed at 4- or 5-position, and whether the product was composed of a single compound or a mixture. (Such representations in Tables appearing hereinafter have the same meaning.)
*3: The representation means that the product was a mixture of a 4-substituted compound and a 5-substituted compound. (Such representations in Tables appearing hereinafter have the same meaning.)

EXAMPLE 2

To a suspension of 3.0 g of the 7-amino-3-{[1-(4-ethyl-2,3-dioxo-1,2,3,4-tetrahydropyrazinyl)]methyl}-$\Delta^3$-cephem-4-carboxylic acid obtained in Example 1-(1) in 30 ml of methanol was added 1.62 g of p-toluenesulfonic acid monohydrate to form a solution, and then 5.0 g of diphenyldiazomethane was slowly added to the solution, after which the resulting mixture was subjected to reaction at room temperature for 15 minutes. After completion of the reaction, the solvent was removed by distillation under reduced pressure, and the residue thus obtained was dissolved in a mixed solvent of 20 ml of ethyl acetate and 20 ml of water. The solution was adjusted to pH 7.0 with sodium hydrogencarbonate. Subsequently, the organic layer was separated and dried over anhydrous magnesium sulfate, and the solvent was removed by distillation under reduced pressure. The residue was purified by a column chromatography (Wako Silica Gel C-200, eluent; benzene:ethyl acetate=1:4 by volume) to obtain 3.1 g (yield, 70.3%) of diphenylmethyl 7-amino-3-{[1-(4-ethyl-2,3-dioxo-1,2,3,4-tetrahydropyrazinyl)]methyl}-$\Delta^3$-cephem-4-carboxylate having a melting point of 183°-186° C. (decomp.).

IR(KBr)cm$^{-1}$: $\nu_{C=O}$ 1765, 1730, 1680, 1630.

In a similar manner, the compounds shown in Table 11 were obtained.

TABLE 11

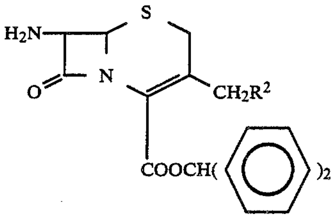

| Compound $R^2$ | m.p. (°C.) | IR (KBr) cm$^{-1}$: $\nu_{C=O}$ |
|---|---|---|
| 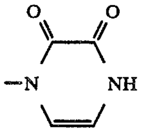 | 129-130 (decomp) | 1765, 1725, 1690, 1630 |
| 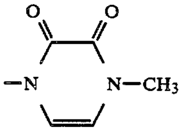 | 127-128 (decomp) | 1770, 1725, 1690, 1640 |
| 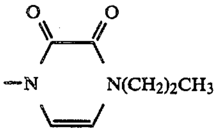 | 169-171 (decomp) | 1765, 1730, 1685, 1635 |
| 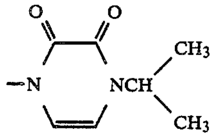 | 179-180.5 (decomp) | 1760, 1720, 1685, 1635 |
| 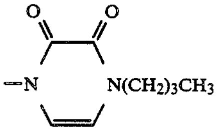 | 180-189 (decomp) | 1760, 1725, 1680, 1630 |
| 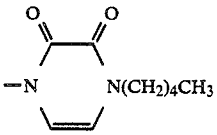 | 185-194 (decomp) | 1765, 1730, 1685, 1630 |

TABLE 11-continued

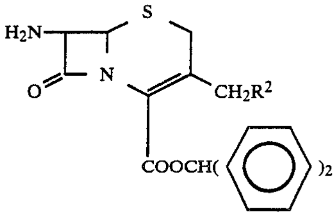

| Compound $R^2$ | m.p. (°C.) | IR (KBr) cm$^{-1}$: $\nu_{C=O}$ |
|---|---|---|
| 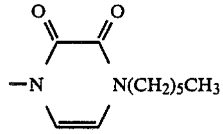 | 170-174 (decomp) | 1765, 1730, 1685, 1635 |
| 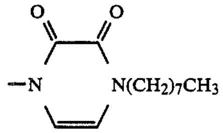 | 186-188 (decomp) | 1765, 1730, 1685, 1635 |
| 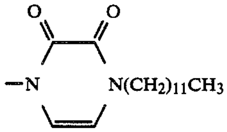 | 164-172 (decomp) | 1765, 1730, 1685, 1635 |
| 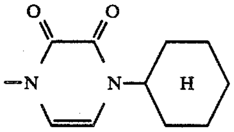 | 165-168 (decomp) | 1765, 1725, 1680, 1625 |
| 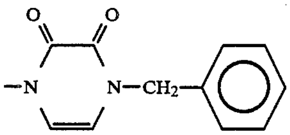 | 155-160 (decomp) | 1770, 1725, 1680, 1630 |
| 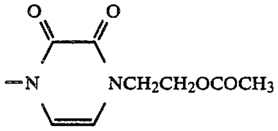 | 146-148 (decomp) | 1770, 1725, 1678, 1623 |
| 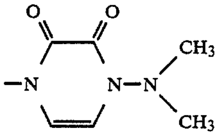 | 172-175 | 1760, 1720, 1680, 1630 |
| 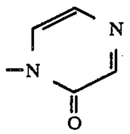 | 82-85 (decomp) | 1775, 1720, 1650 |
| 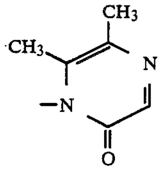 | 108-114 (decomp) | 1765, 1725, 1650 |

TABLE 11-continued

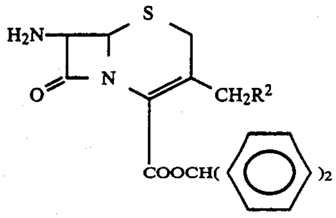

| Compound $R^2$ | m.p. (°C.) | IR (KBr) $cm^{-1}$: $\nu_{C=O}$ |
|---|---|---|
| 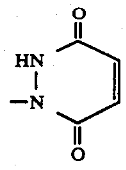 | 132–135 (decomp) | 1780, 1730, 1665 |
| 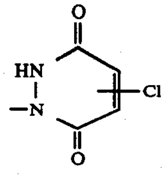 | 178–181 (decomp) | 1780, 1730, 1660 |
| 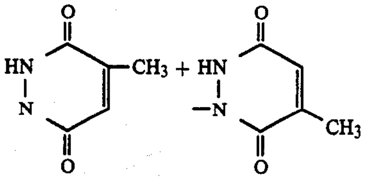 | 137–139 (decomp.) | 1780, 1730, 1660 |
| 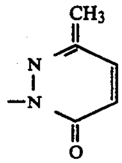 | 90–93 (decomp.) | 1770, 1720, 1660 |
| 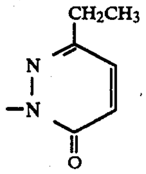 | 138–143 (decomp.) | 1770, 1720, 1660 |

EXAMPLE 3

In a mixed solvent of 25 ml of trifluoroacetic acid and 10 ml of anisole was dissolved 4.9 g of diphenylmethyl 7-amino-3-[1-(2,3-dioxo-1,2,3,4-tetrahydropyrazinyl)-methyl]-$\Delta^3$-cephem-4-carboxylate and the solution was subjected to reaction at room temperature for 2 hours. After completion of the reaction, the solvent was removed by distillation under reduced pressure, and 50 ml of diethyl ether was added to the residue, after which crystals were collected by filtration. The crystals were sufficiently washed with 40 ml of diethyl ether and then dried to obtain 4.25 g (yield, 97.0%) of trifluoroacetic acid salt of 7-amino-3-{[1-(2,3-dioxo-1,2,3,4-tetrahydropyrazinyl)]methyl}-$\Delta^3$-cephem-4-carboxylic acid having a melting point of 105°–106° C. (decomp.)

IR(KBr)$cm^{-1}$: $\nu_{C=O}$ 1780, 1700–1630.

NMR ($CF_3COOD$) $\delta$ values: 3.72 (2H, bs, $C_2$—H), 5.14, 5.52 (2H, ABq, J=15 Hz,

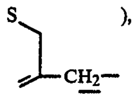

5.44 (2H, s, $C_6$—H, $C_7$—H), 6.78, 6.98 (2H, ABq, J=6 Hz,

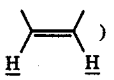

In a similar manner, the compounds shown in Table 12 were obtained.

TABLE 12
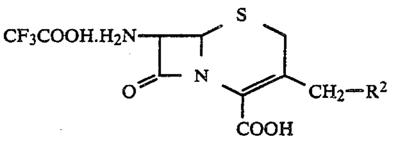
| Compound $R^2$ | m.p. (°C.) | IR (KBr) $cm^{-1}$: $\nu_{C=O}$ | NMR ( $(d_6\text{-DMSO} + CF_3COOD)^{*1}$ / $(CF_3COOD)^{*2}$ / $(d_6\text{-DMSO} + D_2O)^{*3}$ ) δ values: |
|---|---|---|---|
| 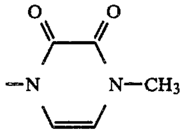 | 109–110 (decomp.) | 1795, 1680, 1635 | 3.36 (3H, s, $NCH_3$), 3.50 (2H, bs, $C_2$—H), 4.53, 5.11 (2H, ABq, J=15Hz, 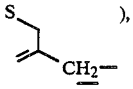 ), 5.06 (1H, d, J=5Hz, $C_6$—H), 5.17 (1H, d, J=5Hz, $C_7$—H), 6.73 (2H, bs, 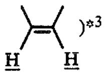 )*3 |
| 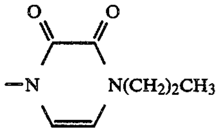 | 152–155 (decomp.) | 1780, 1675, 1635 | 0.91 (3H, t, J=7Hz, $N(CH_2)_2CH_3$), 1.35–2.08 (2H, m, $NCH_2CH_2CH_3$), 3.52 (2H, bs, $C_2$—H), 3.77 (2H, t, J=7Hz, $NCH_2CH_2CH_3$), 4.31, 4.86 (2H, ABq, J=15Hz, 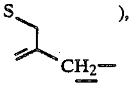 ), 5.35 (2H, bs, $C_6$—H, $C_7$—H), 6.73 (2H, bs, 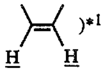 )*1 |
| 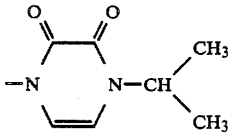 | 159.5–161.5 (decomp.) | 1780, 1680～1620 | 1.46 (6H, d, J=7Hz, 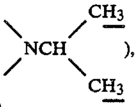 ), 3.70 (2H, bs, $C_2$—H), 4.77–5.60 (3H, m, 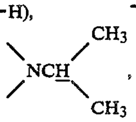 , 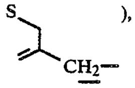 ), 5.46 (2H, bs, $C_6$—H, $C_7$—H), 6.82, 7.04 (2H, ABq, J=6Hz, 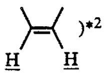 )*2 |

TABLE 12-continued

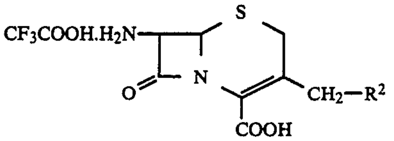

| Compound $R^2$ | m.p. (°C.) | IR (KBr) $cm^{-1}$: $\nu_{C=O}$ | NMR ( $(d_6\text{-DMSO} + CF_3COOD)^{*1}$ / $(CF_3COOD)^{*2}$ / $(d_6\text{-DMSO} + D_2O)^{*3}$ ) δ values: |
|---|---|---|---|
| 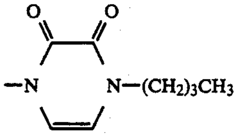 | 158–162 (decomp.) | 1780, 1675, 1635 | 0.92 (3H, t, J=7Hz, $N(CH_2)_3C\underline{H_3}$),<br>1.10–1.90 (4H, m, $NCH_2(C\underline{H_2})_2CH_3$),<br>3.62 (2H, bs, $C_2$—H),<br>3.75 (2H, t, J=7Hz, $NC\underline{H_2}(CH_2)_2CH_3$),<br>4.56, 5.18 (2H, ABq, J=15Hz, 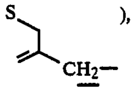 ),<br>5.29 (2H, s, $C_6$—H, $C_7$—H),<br>6.70 (2H, bs, 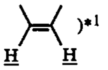 )*1 |
| 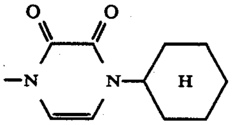 | 167–169 (decomp.) | 1780, 1680~1620 | 1.15–2.35 (10H, m, 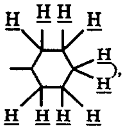 ),<br>3.69 (2H, bs, $C_2$—H),<br>4.47–5.07(1H, m, 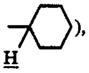 ),<br>5.21–5.54 (2H, m, 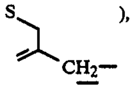 ),<br>5.47 (2H, s, $C_6$—H, $C_7$—H),<br>6.81–6.98 (2H, ABq, J=6Hz, 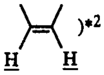 )*2 |
| 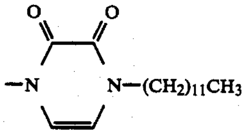 | 138–143 (decomp.) | 1775, 1675, 1635 | 0.89 (3H, t, J=7Hz, $NCH_2(CH_2)_{10}C\underline{H_3}$),<br>1.02–1.85 (20H, m, $NCH_2\underline{(CH_2)_{10}}CH_3$),<br>3.63 (2H, bs, $C_2$—H),<br>3.76 (2H, t, J=7Hz, $NC\underline{H_2}(CH_2)_{10}CH_3$),<br>4.57, 5.21 (2H, ABq, J=15Hz, 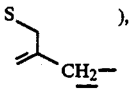 ),<br>5.32 (2H, bs, $C_6$—H, $C_7$—H),<br>6.67 (2H, bs, 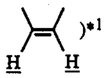 )*1 |

TABLE 12-continued

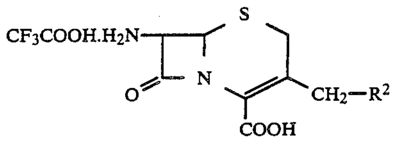

| Compound $R^2$ | m.p. (°C.) | IR (KBr) $cm^{-1}$: $\nu_{C=O}$ | NMR ((d6-DMSO + $CF_3COOD$)*1 ($CF_3COOD$)*2 (d6-DMSO + $D_2O$)*3) δ values: |
|---|---|---|---|
| 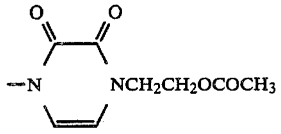 | 86-91 (decomp.) | 1780, 1725, 1675, 1635 | 2.03 (3H, s, $-OCOCH_3$), 3.59 (2H, bs, $C_2-H$), 3.86-4.54 (4H, m, 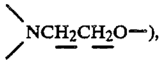), 4.57, 5.16 (2H, ABq, J=15Hz, 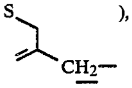), 5.28 (2H, bs, $C_6-H$, $C_7-H$), 6.81 (2H, bs, 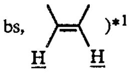)*1 |
| 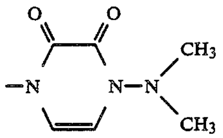 | 158-160 (decomp.) | 1780, 1680~1630 | 3.34 (6H, s, 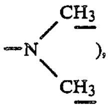), 3.72 (2H, bs, $C_2-H$), 5.12, 5.50 (2H, ABq, J=15Hz, 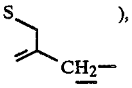), 5.49 (2H, s, $C_6-H$, $C_7-H$), 7.15 (2H, bs, 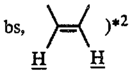)*2 |
| 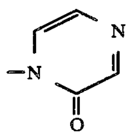 | 119-122 (decomp.) | 1780, 1675~1640 | 3.89 (2H, bs, $C_2-H$), 5.26, 5.62 (2H, ABq, J=15Hz, 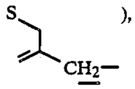), 5.52 (2H, s, $C_6-H$, $C_7-H$), 7.93, 8.69 (2H, ABq, J=5Hz, 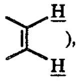), 8.88 (1H, s, 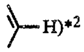)*2 |
| 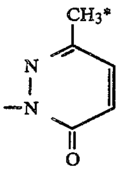 | 241-243 (decomp.) | 1800, 1660, 1600 | 2.58 (3H, s, $-CH_3$), 3.73 (2H, bs, $C_2-H$), 5.50 (2H, bs, $C_2-H$), 5.51, 5.93 (2H, ABq, J=15Hz, 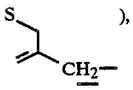), 7.52, 7.79 (2H, ABq, J=10Hz, 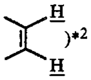)*2 |
| 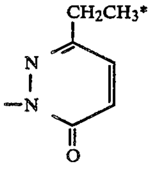 | 219-222 (decomp.) | 1800, 1660, 1600 | 1.36 (3H, t, J=7Hz, $-CH_2CH_3$), 2.90 (2H, q, J=7Hz, $-CH_2CH_3$), 3.69 (2H, bs, $C_2-H$), 5.47 (2H, bs, $C_6-H$, $C_7-H$), 5.48, 5.90 (2H, ABq, J=15Hz, 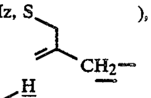), 7.48, 7.76 (2H, ABq, J=10Hz, 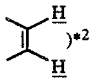)*2 |

TABLE 12-continued

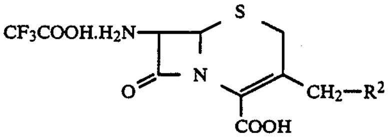

| Compound $R^2$ | m.p. (°C.) | IR (KBr) $cm^{-1}$: $\nu_{C=O}$ | NMR ((d6-DMSO + $CF_3COOD$)*1 ($CF_3COOD$)*2 (d6-DMSO + $D_2O$)*3) δ values: |
|---|---|---|---|
| 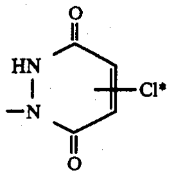 | >200 | 1795,<br>1640,<br>1600 | 3.70 (2H, bs, $C_2$—H), 5.34, 5.79 (2H, ABq, J=16Hz, 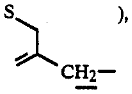), 5.47 (2H, s, $C_6$—H, $C_7$—H),<br>7.59 (1H, s, 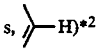)*2 |
| 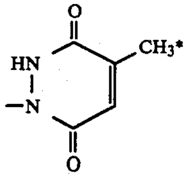<br>+<br>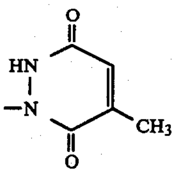 | >200 | 1795,<br>1640,<br>1600 | 2.42 (1.5H, s, —$CH_3$ × 0.5), 2.50 (1.5H, s, —$CH_3$ × 0.5), 3.73 (2H, bs, $C_2$—H), 5.52 (2H, s, $C_6$—H, $C_7$—H), 5.63 (2H, bs, 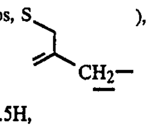),<br>7.38 (0.5H, s, 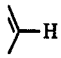 × 0.5), 7.60 (0.5H,<br>s, 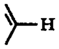 × 0.5)*2 |
| 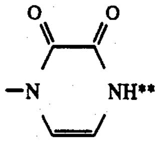 | 139-140<br>(decomp.) | 1780,<br>1710,<br>1690~1620 | 3.46 (2H, bs, $C_2$—H), 4.47, 5.07 (2H, ABq, J=15Hz, 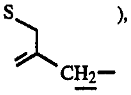), 5.04 (1H, d, J=5Hz,<br>$C_6$—H), 5.20 (1H, d, J=5Hz, $C_7$—H), 6.34,<br>6.59 (2H, ABq, J=6Hz, 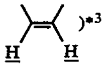)*3 |
| 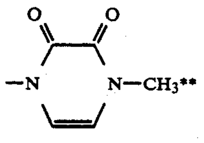 | 152-155<br>(decomp.) | 1780,<br>1690,<br>1660,<br>1620 | 3.35 (3H, s, NCH3), 3.48 (2H, bs, $C_2$—H),<br>4.50, 5.12 (2H, ABq, J=15Hz, 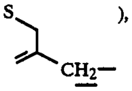),<br>4.87 (1H, d, J=5Hz, $C_6$—H), 5.03 (1H, d,<br>J=5Hz, $C_7$—H), 6.70 (2H, bs, 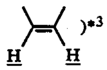)*3 |

(Note)
* = Free compound; Objective compounds were obtained by reacting in a mixed solvent of trifluoroacetic acid and anisole, then removing the solvent, dissolving the residue in water and adjusting the pH to 3.5 with 28% aqueous ammonia solution.
** = Free Compound; obtained by treating the trifluoroacetic acid salt with pyridine in methanol.

EXAMPLE 4

To a suspension of 5.0 g of 7-amino-3-{[1-(3-methyl-6-oxo-1,6-dihydropyridazinyl)]methyl}-Δ3-cephem-4-carboxylic acid in 15 ml of acetone were added 2.36 g of 1,8-diazabicyclo[5,4,0]-7-undecene and 4.51 g of pivaloyloxymethyl iodide at 10°-15° C., and the mixture was subjected to reaction for 30 minutes. After completion of the reaction, the reaction mixture was introduced into a mixed solvent of 50 ml of water and 50 ml of ethyl acetate, and the organic layer was separated, washed with water and then dried over anhydrous magnesium sulfate. Subsequently, 10 ml of an ethyl acetate solution containing 1.40 g of oxalic acid was added thereto, and the precipitated crystals were collected by filtration and washed with ethyl acetate to obtain 4.59 g (yield, 56.2%) of oxalic acid salt of pivaloyloxymethyl 7-amino-3-{[1-(3-methyl-6-oxo-1,6-dihydropyridazinyl)]methyl}-$\Delta^3$-cephem-4-carboxylate having a melting point of 145°-147° C. (decomp.).

IR(KBr)$cm^{-1}$: $\nu_{C=O}$ 1790, 1750, 1660.

NMR ($d_6$-DMSO) δ values: 1.21 (9H, s, $-CH_3x3$). 2.29 (3H, s,

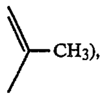), 3.52 (2H, bs, $C_2$—H), 4.94, 5.33 (2H, ABq, J=15 Hz,

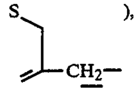), 5.14 (1H, d, J=5 Hz, $C_6$—H), 5.76–6.23 (3H, m, $C_7$—H, $-OCH_2O-$), 7.01, 7.53 (2H, ABq, J=10 Hz,

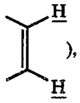), 7.44 (3H, bs, $-NH_3^{\oplus}$)

EXAMPLE 5

(1) To a solution of 2.69 g of 1-(5-methyl-2-oxo-1,3-dioxol-4-yl)methyl-2,3-dioxo-1,2,3,4-tetrahydropyrazine in 27 ml of N,N-dimethylformamide was added 1.52 g of potassium carbonate, and the resulting mixture was stirred at room temperature for 20 minutes. Subsequently, 4.67 g of tert.-butyl 7-phenylacetamido-3-bromomethyl-$\Delta^2$-cephem-4-carboxylate was added thereto with ice-cooling, and the mixture was subjected to reaction at room temperature for 2 hours. The reaction mixture was introduced into a mixed solvent of 200 ml of ethyl acetate and 150 ml of water, and the organic layer was separated, washed with 150 ml of water, and then dried over anhydrous magnesium sulfate. Subsequently, the solvent was removed by distillation under reduced pressure, and the resulting residue was dissolved in 100 ml of chloroform. To the solution was added 2.45 g (purity, 70%) of m-chloroperbenzoic acid, and the mixture was subjected to reaction at room temperature for 1 hour. The solvent was removed by distillation under reduced pressure, and to the residue were added 100 ml of ethyl acetate and 100 ml of water. The organic layer was separated, washed with 100 ml of water, and then dried over anhydrous magnesium sulfate. The solvent was removed by distillation under reduced pressure, and the resulting residue was purified by a column chromatography (Wako Silica Gel C-200, eluent; chloroform) to obtain 2.70 g (yield, 43.2% of tert.-butyl 7-phenylacetamido-3-{[1-[4-(5-methyl-2-oxo-1,3-dioxol-4-yl)methyl-2,3-dioxo-1,2,3,4-tetrahydropyrazinyl]]methyl}-$\Delta^3$-cephem-4-carboxylate-1-oxide having a melting point of 135°-136° C. (decomp.).

IR(KBr)$cm^{-1}$: $\nu_{C=O}$ 1820, 1790, 1720, 1685, 1650.

(2) In a mixed solvent of 12 ml of N,N-dimethylformamide and 6 ml of acetonitrile was dissolved 3.0 g of tert.-butyl 7-phenylacetamido-3-{[1-[4-(5-methyl-2-oxo-1,3-dioxol-4-yl)methyl-2,3-dioxo-1,2,3,4-tetrahydropyrazinyl]]methyl}-$\Delta^3$-cephem-4-carboxylate-1-oxide. To the solution were added 1.0 g of stannous chloride and 1.58 g of acetyl chloride in this order with ice-cooling, and the mixture was subjected to reaction at room temperature for 30 minutes. The solvent was removed by distillation under reduced pressure, and to the residue were added 50 ml of ethyl acetate and 50 ml of water, after which the resulting mixture was adjusted to pH 6.0 with sodium hydrogencarbonate. Subsequently, the organic layer was separated, washed with 50 ml of water, and then dried over anhydrous magnesium sulfate. The solvent was removed by distillation under reduced pressure, and the residue was purified by a column chromatography (Wako Silica Gel C-200, eluent; toluene:ethyl acetate=3:2 by volume) to obtain 2.12 g (yield, 72.4%) of tert.-butyl 7-phenylacetamido-3-{[1-[4-(5-methyl-2-oxo-1,3-dioxol-4-yl)methyl-2,3-dioxo-1,2,3,4-tertrahydropyrazinyl]]methyl}-$\Delta^3$-cephem-4-carboxylate having a melting point of 120°-122° C. (decomp.).

IR(KBr)$cm^{-1}$: $\nu_{C=O}$ 1820, 1775, 1715, 1685, 1645.

NMR ($CDCl_3$) δ values: 1.58 (9H, s, $-C(CH_3)_3$), 2.28 (3H, s, $-CH_3$) 3.17, 3.61 (2H, ABq, J=18 Hz, $C_2$—H), 3.77 (2H, s,

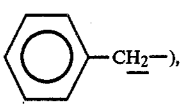), 4.53, 5.13 (2H, ABq, J=15 Hz,

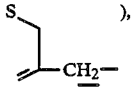), 4.71 (2H, s, $>NCH_2-$), 5.03 (1H, d, J=5 Hz, $C_6$—H), 5.93 (1H, dd, J=5 Hz, J=8 Hz, $C_7$—H), 6.53, 6.89 (2H, ABq, J=6 Hz,

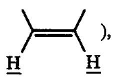), 7.32–7.51 (5H, m,

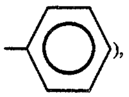), 7.57 (1H, d, J=8 Hz, —CONH—).

In a similar manner to that in above (1) and (2), the compounds shown in Table 13 were obtained.

TABLE 13

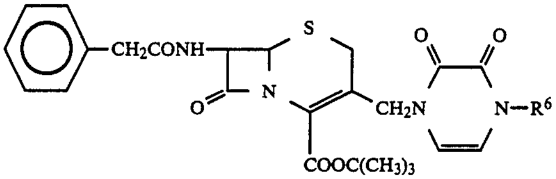

| Compound $R^6$ | m.p. (°C.) | IR (KBr) $cm^{-1}$: $\nu_{C=C}$ | NMR (d$_6$-DMSO . . . * / $CDCl_3$ . . . **) δ values |
|---|---|---|---|
| 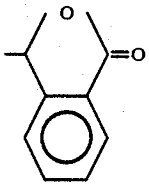 | 180–183 (decomp.) | 1780, 1710, 1700, 1680, 1645 | 1.52 (9H, s, $-C(CH_3)_3$), 3.57 (4H, bs, $C_2-H$, 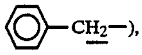), 4.30, 5.12 (2H, ABq, J=15Hz, 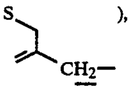), 5.12 (1H, d, J=5Hz, $C_6-H$), 5.75 (1H, dd, J=5Hz, J=8Hz, $C_7-H$), 6.07, 6.54 (2H, ABq, J=6Hz, 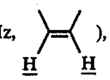), 7.12-7.45 (5H, m, 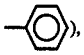), 7.57-8.14 (5H, m, 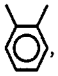, 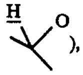), 9.14 (1H, d, J=8Hz, $-CONH-$) * |
| $-CH_2OCOC(CH_3)_3$ | 105-108 (decomp.) | 1780, 1740, 1730, 1660 | 1.21 (9H, s, $-C(CH_3)_3$), 1.56 (9H, s, $-C(CH_3)_3$), 3.22 3.61 (2H, ABq, J=18Hz, $C_2-H$), 3.71 (2H, s, 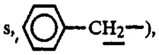), 4.58, 5.11 (2H, ABq, J=15Hz, 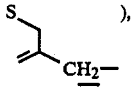), 5.03 (1H, d, J=5Hz, $C_6-H$), 5.81 (2H, s, 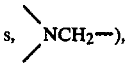), 5.93 (1H, dd, J=5Hz, J=9Hz, $C_7-H$), 6.55, 6.88 (2H, ABq, J=7Hz, 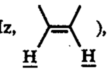), 7.14 (1H, d, J=9Hz, $-CONH-$), 7.43 (5H, s, 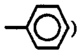) ** |
| $-CH_2COOCH($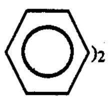$)_2$ | 124–129 (decomp.) | 1770, 1730, 1685, 1650 | 1.53 (9H, s, $-C(CH_3)_3$), 3.27 (2H, bs, $C_2-H$), 3.61 (2H, s, 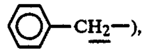), 4.54 (2H, s, 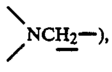), 4.91 (2H, bs, 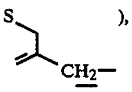), 5.18 (1H, d, J=5Hz, $C_6-H$), 5.86 (1H, dd, J=5Hz, J=8Hz, $C_7-H$), 6.12, 6.59 (2H, ABq, |

TABLE 13-continued

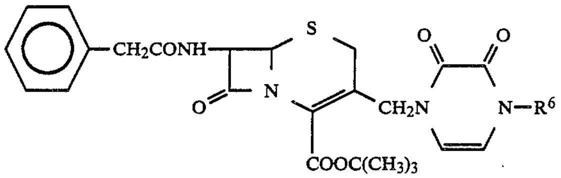

| Compound $R^6$ | m.p. (°C.) | IR (KBr) $cm^{-1}$: $\nu_{C=C}$ | NMR ( $d_6$-DMSO . . . * / $CDCl_3$ . . . ** ) δ values |
|---|---|---|---|
| | | | J=6Hz, 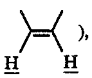 ), 6.88 (1H, s, —CH 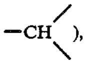 ), 6.96–7.47 (15H, m, — 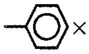 × 3), 7.95 (1H, d, J=8Hz, —CONH—) ** |

(3) In 30 ml of anhydrous methylene chloride was dissolved 2.0 g of tert.-butyl 7-phenylacetamido-3-{[1-[4-(5-methyl-2-oxo-1,3-dioxol-4-yl)methyl-2,3-dioxo-1,2,3,4-tetrahydropyrazinyl]]methyl}-$\Delta^3$-cephem-4-carboxylate. To this solution were added 1.59 g of N,N-dimethylaniline and 0.57 g of trimethylsilyl chloride in this order, and the resulting mixture was stirred at room temperature for 1 hour. The reaction mixture was cooled to −40° C., and 0.89 g of phosphorus pentachloride was added thereto, and the mixture was subjected to reaction at −30° to −20° C. for 2.5 hours. Subsequently, the reaction mixture was cooled to −40° C., and 5.2 g of anhydrous methanol was added thereto, after which the reaction was continued with ice-cooling for 1 hour. To the reaction mixture was added 20 ml of water and stirring was continued for a further 30 minutes. Subsequently, the reaction mixture was adjusted to pH 0.5 with 6N hydrochloric acid, and then the aqueous layer was separated. To this aqueous layer was added 50 ml of ethyl acetate, and the mixture was adjusted to pH 6.5 with sodium hydrogencarbonate. The organic layer was separated, washed with 50 ml of water, and then dried over anhydrous magnesium sulfate. The solvent was removed by distillation under reduced pressure, and to the residue was added 50 ml of diethyl ether. The crystals were collected by filtration to obtain 1.05 g (yield, 64.8%) of tert.-butyl 7-amino-3-{[1-[4-(5-methyl-2-oxo-1,3-dioxol-4-yl)methyl-2,3-dioxo-1,2,3,4-tetrahydropyrazinyl]]methyl}-$\Delta^3$-cephem-4-carboxylate having a melting point of 185°–188° C. (decomp.).

IR(KBr)$cm^{-1}$: $\nu_{C=O}$ 1820, 1765, 1705, 1690, 1635.

NMR ($CDCl_3$+$d_6$-DMSO) δ values: 1.52 (9H, s, —$C(CH_3)_3$), 2.24 (3H, s, —$CH_3$), 3.46 (2H, bs, $C_2$—H), 4.35, 5.08 (2H, ABq, J=15 Hz,

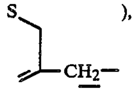 ), 4.76–5.09 (4H, m, >N$C\underline{H_2}$—, $C_6$—H, $C_7$—H), 6.74 (2H, s,

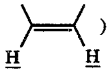 )

In a similar manner, the compounds shown in Table 14 were obtained.

TABLE 14

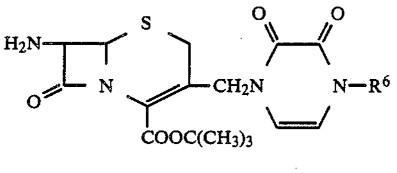

| Compound $R^6$ | m.p. (°C.) | IR (KBr) $cm^{-1}$: $\nu_{C=O}$ | NMR ( $d_6$-DMSO . . . * / $CDCl_3$ . . . ** ) δ values |
|---|---|---|---|
| 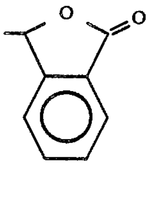 | 111–113 (decomp.) | 1780, 1710, 1690, 1650 | 1.50 (9H, s, —$C(CH_3)_3$), 3.48 (2H, bs, $C_2$—H), 4.28, 5.07 (2H, ABq, J=15Hz, 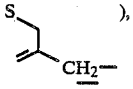 ), 4.82 (1H, d, J=5Hz, $C_6$—H), 5.03 (1H, d, J=5Hz, $C_7$—H), 6.08, |

TABLE 14-continued

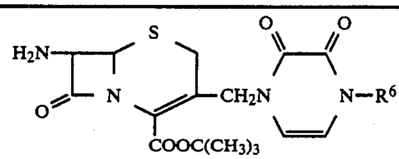

| Compound $R^6$ | m.p. (°C.) | IR (KBr) $cm^{-1}$: $\nu_{C=O}$ | NMR (d6-DMSO . . . * / $CDCl_3$ . . . **) δ values |
|---|---|---|---|
| | | | 6.55 (2H, ABq, J=6Hz, 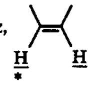 * ), 7.58-8.12 (5H, m, 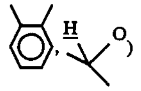 ) |
| $-CH_2OCOC(CH_3)_3$ (Hydrochloride)*** | 132-134 (decomp.) | 1775, 1740, 1715, 1695, 1640 | 1.17 (9H, s, $-C(CH_3)_3$), 1.53 (9H, s, $-C(CH_3)_3$), 3.67 (2H, bs, $C_2$—H), 4.41, 5.13 (2H, ABq, J=15Hz, 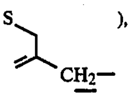 ), 5.30 (2H, s, $NCH_2$—), 5.75 (2H, bs, $C_6$—H, $C_7$—H), 6.80 (2H, bs, 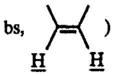 * ) |
| $-CH_2COOCH($ 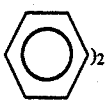 $)_2$ | 160-163 (decomp.) | 1780, 1760, 1715, 1690, 1650 | 1.54 (9H, s, $-C(CH_3)_3$), 1.74 (2H, bs, $-NH_2$), 3.05, 3.48 (2H, ABq, J=18Hz, $C_2$—H), 4.40, 4.99 (2H, ABq, J=15Hz, 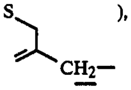 ), 4.55 (2H, s, $NCH_2$—), 4.65 (1H, d, J=5Hz, $C_6$—H), 4.84 (1H, d, J=5Hz, $C_7$—H), 6.09, 6.62 (2H, ABq, J=6Hz, 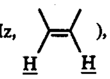 ), 6.85 (1H, s, —CH ** ), 7.17-7.31 (10H, m, 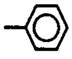 × 2) |

Note:
***Iminoether compound was poured into water, and the deposited hydrochloride was isolated.

EXAMPLE 6

(1) In 2.29 ml of N,N-dimethylacetamide and 4.58 ml of acetonitrile was dissolved 2.29 g of 2-(2-formamidothiazol-4-yl)-2-(syn)-methoxyiminoacetic acid, and to the resulting solution was added dropwise 1.62 g of phosphorus oxychloride, after which the mixture was subjected to reaction at −5° to 0° C. for 1 hour. Subsequently, 5.18 g of diphenylmethyl 7-amino-3-{[1-(4-ethyl-2,3-dioxo-1,2,3,4-tetrahydropyrazinyl)]methyl}-$\Delta^3$-cephem-4-carboxylate was added to the reaction mixture, and the mixture was subjected to reaction at −5° to 0° C. for 1 hour. After completion of the reaction, the reaction mixture was poured into a mixed solvent of 80 ml of water and 80 ml of ethyl acetate, and the resulting solution was adjusted to pH 6.5 with sodium hydrogencarbonate. Subsequently, the organic layer was separated, and dried over anhydrous magnesium sulfate. The solvent was removed by distillation under reduced pressure, and to the residue was added 60 ml of diethyl ether. Then, the crystals were collected by filtration to obtain 6.05 g (yield, 83.0%) of diphenylmethyl 7-[2-(2-formamidothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylate having a metling point of 165°-168° C.

IR (KBr) $cm^{-1}$: $\nu_{C=O}$ 1780, 1720, 1680, 1640.

NMR (d6-DMSO) δ values: 1.18 (3H, t, J=7 Hz, $>N-CH_2CH_3$), 3.59 (2H, bs, $C_2$—H), 3.72 (2H, q, J=7 Hz, $>N-CH_2CH_3$), 3.97 (3H, s, $-OCH_3$), 4.42, 5.04 (2H, ABq, J=15 Hz,

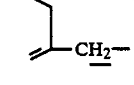 ), 5.30 (1H, d, J=5 Hz, $C_6$—H), 6.02 (1H, dd, J=5 Hz, J=8 Hz, $C_7$—H), 6.50, 6.62 (2H, ABq, J=6 Hz,

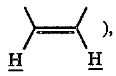
),
7.04 (1H, s, —CH<), 7.17-7.82 (11H, m,
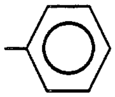
× 2,
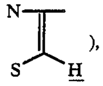
),
8.63 (1H, s, HCO—), 9.89 (1H, d, J=8 Hz, —CONH—), 12.68 (1H, bs, HCONH—)
In a similar manner, the compounds shown in Tables 15, 16 and 17 were obtained.
TABLE 15
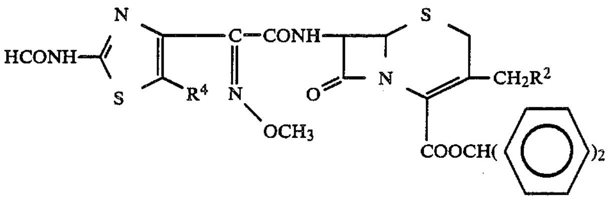
(syn-isomer)
| Compound $R^2$ | $R^4$ | m.p. (°C.) | IR (KBr) $cm^{-1}$: $\nu_{C=O}$ |
|---|---|---|---|
| 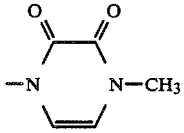 | H | 120-125 (decomp.) | 1780, 1720, 1680-1640 |
| 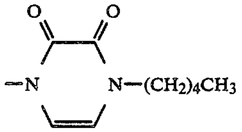 | H | 154-156 (decomp.) | 1785, 1720, 1685, 1645 |
| 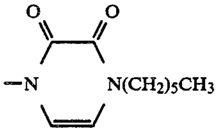 | H | 131-136 (decomp.) | 1783, 1725, 1680, 1645 |
| 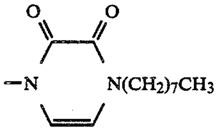 | H | 180-182 (decomp.) | 1780, 1720, 1680-1640 |
| 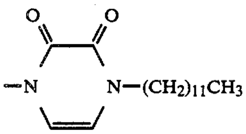 | H | 158-166 (decomp.) | 1780, 1725, 1675, 1640 |
| 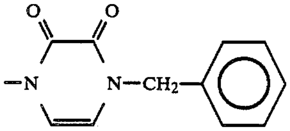 | H | 126-138 | 1785, 1725, 1685, 1650 |
| 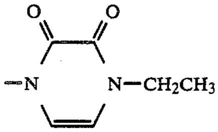 | Br | 142 (decomp.) | 1780, 1720, 1675, 1640 |

TABLE 15-continued
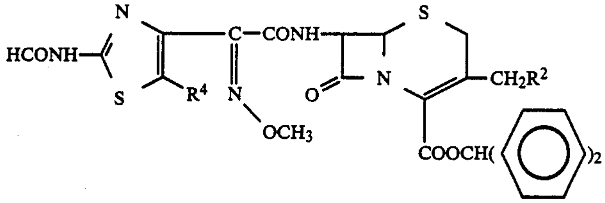
(syn-isomer)
| Compound | | | |
|---|---|---|---|
| $R^2$ | $R^4$ | m.p. (°C.) | IR (KBr) $cm^{-1}$: $\nu_{C=O}$ |
| 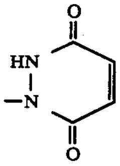 | H | 171-173 (decomp.) | 1780, 1720, 1690-1650 |
| 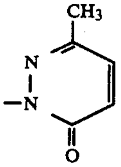 | H | 148-151 (decomp.) | 1780, 1730, 1690, 1660 |
| 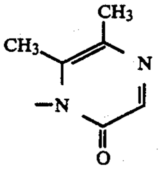 | H | 191-195 (decomp.) | 1775, 1720, 1670 |
TABLE 16
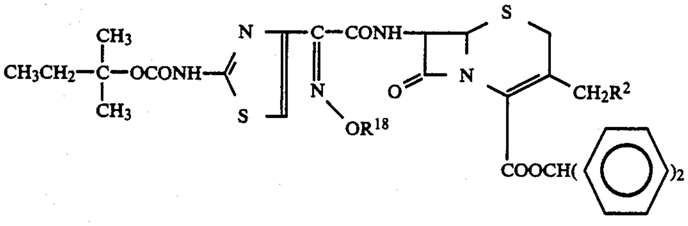
(syn-isomer)
| Compound | | | IR (KBr) |
|---|---|---|---|
| $R^2$ | $R^{18}$ | m.p. (°C.) | $cm^{-1}$: $\nu_{C=O}$ |
| 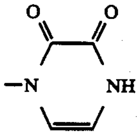 | $-CH_3$ | 176-179 (decomp.) | 1780, 1720, 1680, 1640 |
| 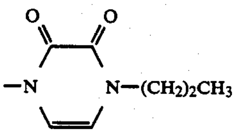 | $-CH_3$ | 152-155 (decomp.) | 1780, 1720, 1680, 1640 |
| 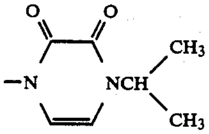 | $-CH_3$ | 158-160 (decomp.) | 1780, 1720, 1680, 1640 |

TABLE 16-continued
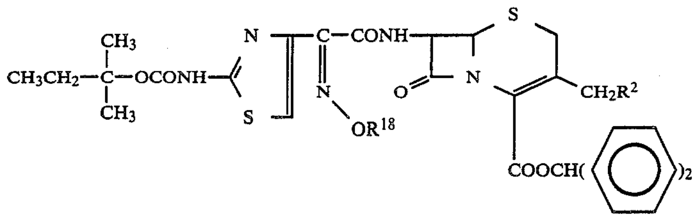
(syn-isomer)
| Compound | | | IR (KBr) |
|---|---|---|---|
| $R^2$ | $R^{18}$ | m.p. (°C.) | $cm^{-1}$: $\nu_{C=O}$ |
| 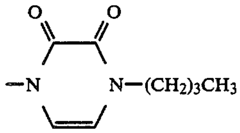 | $-CH_3$ | 166–167 (decomp.) | 1780, 1720, 1685, 1645 |
| 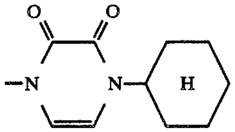 | $-CH_3$ | 162–165 (decomp.) | 1780, 1720, 1680, 1640 |
| 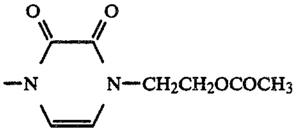 | $-CH_3$ | 145–147 (decomp.) | 1780, 1720, 1682, 1640 |
| 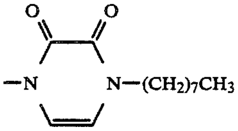 | $-CH_3$ | 138–144 (decomp.) | 1780, 1715, 1690, 1620 |
| 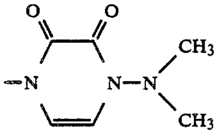 | $-CH_3$ | 88–90 | 1780, 1720, 1690–1620 |
| 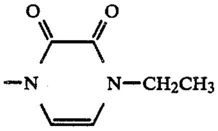 | $-CH_2CH_3$ | 131 (decomp.) | 1786, 1723, 1684, 1645 |
| 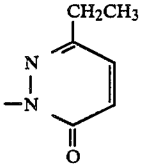 | $-CH_3$ | 118–120 (decomp.) | 1780, 1720, 1660 |
| 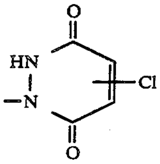 | $-CH_3$ | 190–192 (decomp.) | 1780, 1720, 1665 |

TABLE 16-continued
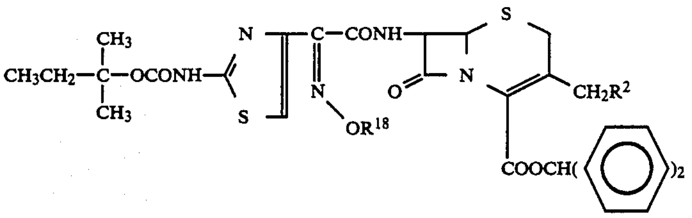
(syn-isomer)
| Compound R² | R¹⁸ | m.p. (°C.) | IR (KBr) cm⁻¹: $\nu_{C=O}$ |
|---|---|---|---|
| 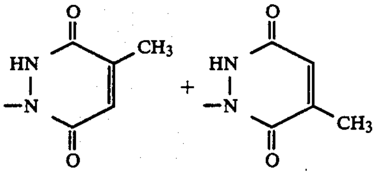 | $-CH_3$ | 183–185 (decomp.) | 1780, 1720, 1670 |
| 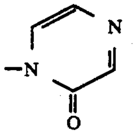 | $-CH_3$ | 128–131 (decomp.) | 1780, 1720, 1680, 1660 |
TABLE 17
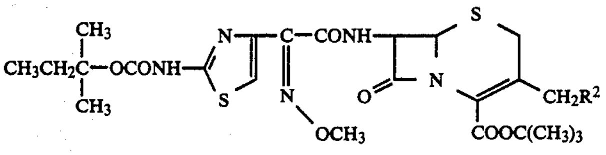
(syn-isomer)
| Compound $R^2$ | m.p. (°C.) | IR (KBr) $cm^{-1}$: $\nu_{C=O}$ |
|---|---|---|
| 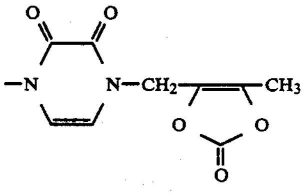 | 141–143 (decomp.) | 1815, 1775, 1710, 1680, 1640 |
| 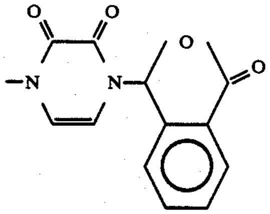 | 154–156 (decomp.) | 1775, 1710, 1700, 1680, 1650 |
| 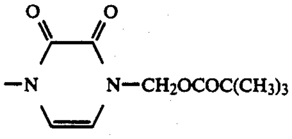 | 85–88 (decomp.) | 1785, 1730, 1715, 1660 |

TABLE 17-continued

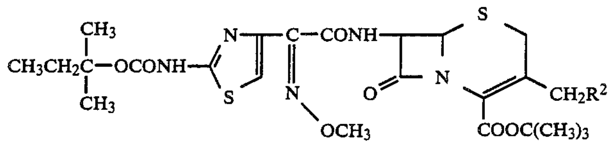

(syn-isomer)

| Compound $R^2$ | m.p. (°C.) | IR (KBr) $cm^{-1}$: $\nu_{C=O}$ |
|---|---|---|
| 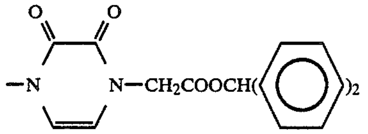 | 144–146 (decomp.) | 1775, 1745, 1715, 1690, 1650 |

(2) To a solution of 6.05 g of diphenylmethyl 7-[2-(2-formamidothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylate in 31 ml of methanol was added 0.5 ml of concentrated hydrochloric acid, and the mixture was subjected to reaction at 35° C. for 2 hours. After completion of the reaction, the solvent was removed by distillation under reduced pressure. To the residue were added 100 ml of ethyl acetate and 100 ml of water, and the resulting solution was adjusted to pH 6.0 with sodium hydrogencarbonate. Subsequently, the organic layer was separated and dried over anhydrous magnesium sulfate. The solvent was removed by distillation under reduced pressure, and to the residue was added 50 ml of diethyl ether. The crystals were collected by filtration to obtain 5.1 g (yield, 87.7%) of diphenylmethyl 7-[2-(2-aminothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylate having a melting point of 165°-167° C.

IR (KBr) $cm^{-1}$: $\nu_{C=O}$ 1780, 1720, 1680, 1640.

NMR ($d_6$-DMSO) δ values: 1.18 (3H, t, J=7 Hz, >N—$CH_2C\underline{H_3}$), 3.55 (2H, bs, $C_2$—H), 3.75 (2H, q, J=7 Hz, >N—$C\underline{H_2}CH_3$), 3.90 (3H, s, —$OCH_3$), 4.41, 5.02 (2H, ABq, J=15 Hz,

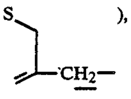), 5.26 (1H, d, J=5 Hz, $C_6$—H), 6.01 (1H, dd, J-5 Hz, J=8 Hz, $C_7$—H), 6.52, 6.65 (2H, ABq, J=6 Hz,

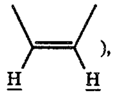), 6.88 (1H, s,

), 7.07 (1H, s, —CH<), 7.15–7.84 (10H, m,

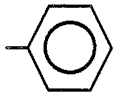 × 2), 9.81 (1H, d, J=8 Hz, —CONH—)

In a similar manner, the compounds shown in Table 18 were obtained.

TABLE 18

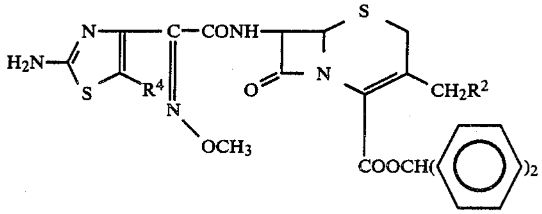

(syn-isomer)

| Compound $R^2$ | $R^4$ | m.p. (°C.) | IR (KBr) $cm^{-1}$: $\nu_{C=O}$ |
|---|---|---|---|
| 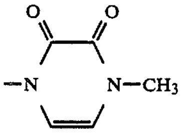 | H | 158–166 (decomp.) | 1780, 1720, 1680, 1640 |
| 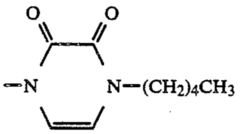 | H | 151–156 (decomp.) | 1780, 1720, 1680, 1640 |
| 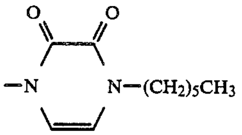 | H | 150–156 (decomp.) | 1780, 1720, 1680, 1640 |

TABLE 18-continued

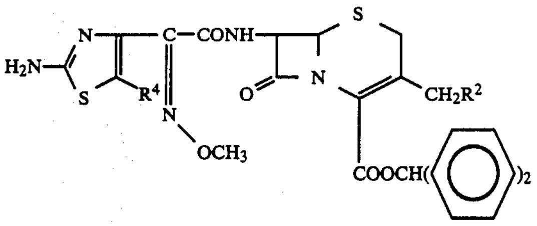

(syn-isomer)

| Compound R² | R⁴ | m.p. (°C.) | IR (KBr) $cm^{-1}$: $\nu_{C=O}$ |
|---|---|---|---|
| 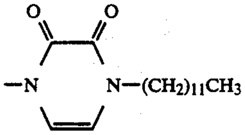 | H | 168-175 (decomp.) | 1775, 1723, 1685, 1640 |
| 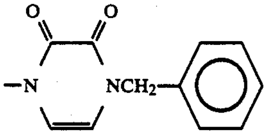 | H | 161-166 | 1780, 1720, 1680, 1640 |
| 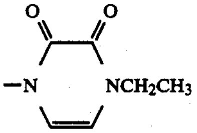 | Br | 146 (decomp.) | 1780, 1720, 1680, 1640 |
| 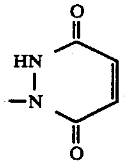 | H | 175-178 (decomp.) | 1780, 1720, 1685-1660 |
| 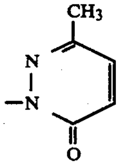 | H | 146-148 (decomp.) | 1780, 1720, 1660 |

(3) In a mixed solvent of 25.5 ml of trifluoroacetic acid and 7.86 g of anisole was dissolved 5.1 g of diphenylmethyl 7-[2-(2-aminothiazol-4yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylate, and the solution was subjected to reaction at room temperature for 2 hours. After completion of the reaction, the solvent was removed by distillation under reduced pressure. To the residue was added 40 ml of diethyl ether and the crystals were collected by filtration to obtain 4.3 g (yield, 91.1%) of trifluoroacetic acid salt of 7-[2-(2-aminothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylic acid having a melting point of 155°-157° C. (decomp.).

IR (KBr) $cm^{-1}$: $\nu_{C=O}$ 1775, 1710-1630.

NMR ($d_6$-DMSO) δ values: 1.21 (3H, t, J=7 Hz, $>N-CH_2C\underline{H}_3$), 3.52 (2H, bs, $C_2-H$), 3.73 (2H, q, J=7 Hz, $>N-C\underline{H}_2CH_3$), 3.96 (3H, s, $-OCH_3$), 4.44, 5.12 (2H, ABq, J=15 Hz,

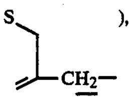 ), 5.21 (1H, d, J=5 Hz, $C_6-H$), 5.83 (1H, dd, J=5 Hz, J=8 Hz, $C_7-H$), 5.86 (3H, bs, $-NH_3^{\oplus}$), 6.71 (2H, bs,

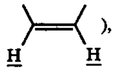 ), 6.95 (1H, s,

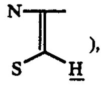 ), 9.90 (1H, d, J=8 Hz, —CONH—).

In a similar manner, the compounds shown in Tables 19 and 20 were obtained.

TABLE 19

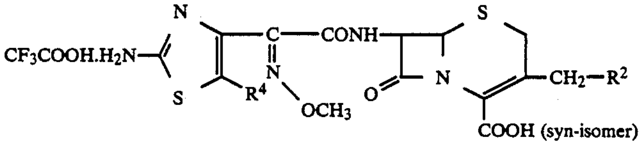

(syn-isomer)

| Compound R² | R⁴ | m.p. (°C.) | IR (KBr) $cm^{-1}$: $\nu_{C=O}$ | NMR ($d_6$-DMSO) δ values: |
|---|---|---|---|---|
| 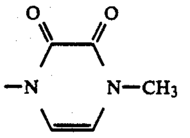 | H | 95-102 (decomp.) | 1773, 1670, 1660, 1640 | 3.34 (3H, s, $>N-CH_3$), 3.51 (2H, bs, $C_2-H$), 4.00 (3H, s, $-OCH_3$), 4.52, 4.90 (2H, ABq, J=15Hz, 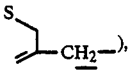 ), 5.25 (1H, d, |

TABLE 19-continued

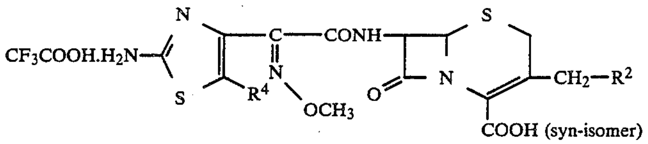

(syn-isomer)

| Compound R² | R⁴ | m.p. (°C.) | IR (KBr) $cm^{-1}$: $\nu_{C=O}$ | NMR ($d_6$-DMSO) δ values: |
|---|---|---|---|---|
| | | | | J=5Hz, $C_6$—H), 5.90 (1H, dd, J=5Hz, J=8Hz, $C_7$—H), 6.68 (2H, bs, 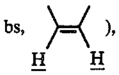), 6.99 (1H, s, 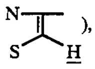), 9.85 (1H, d, J=8Hz, —CONH—) |
| 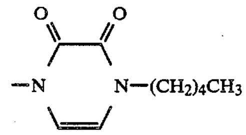 | H | 115-125 (decomp.) | 1770, 1670, 1660, 1635 | 0.86 (3H, t, J=7Hz, $>N-(CH_2)_4CH_3$), 1.05-1.85 (6H, m, $>N-CH_2(CH_2)_3CH_3$), 3.53 (2H, bs, $C_2$—H), 3.73 (2H, t, J=7Hz, $>N-CH_2(CH_2)_3CH_3$), 3.93 (3H, s, $-OCH_3$), 4.40, 5.05 (2H, ABq, J=15Hz, 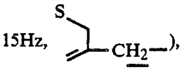), 5.20 (1H, d, J=5Hz, $C_6$—H), 5.86 (1H, dd, J=5Hz, J=8Hz, $C_7$—H), 6.68 (2H, bs, 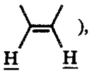), 6.95 (1H, s, 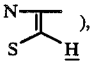), 9.85 (1H, d, J=8Hz, —CONH—) |
| 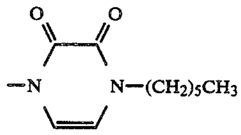 | H | 155-160 (decomp.) | 1770, 1670, 1655, 1630 | 0.87 (3H, t, J=7Hz, $>N-(CH_2)_5CH_3$), 1.04-1.85 (8H, m, $>NCH_2(CH_2)_4CH_3$), 3.53 (2H, bs, $C_2$—H), 3.77 (2H, t, J=7hz, $>NCH_2(CH_2)_4CH_3$), 3.97 (3H, s, $-OCH_3$), 4.47, 5.13 (2H, ABq, J=15Hz, 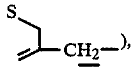), 5.23 (1H, d, J=5Hz, $C_6$—H), 5.82 (1H, dd, J=5Hz, J=8Hz, $C_7$—H), 6.44 (3H, bs, $-NH_3^{\oplus}$), 6.70 (2H, bs, 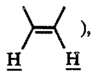), 6.95 (1H, s, 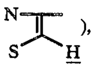), 9.85 (1H, d, J=8Hz, —CONH—) |

TABLE 19-continued

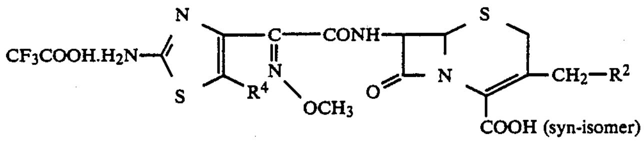

(syn-isomer)

| Compound | | | IR (KBr) | |
|---|---|---|---|---|
| $R^2$ | $R^4$ | m.p. (°C.) | $cm^{-1}$: $\nu_{C=O}$ | NMR ($d_6$-DMSO) δ values: |
| 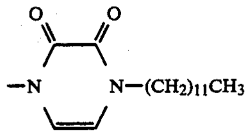 | H | 140-147 (decomp.) | 1770, 1675 1635 | 0.87 (3H, t, J=7Hz, $N-(CH_2)_{11}\underline{CH_3}$), 1.04-1.84 (20H, m, $NCH_2\underline{(CH_2)_{10}}CH_3$), 3.51 (2H, bs, $C_2$—H), 3.72 (2H, t, J=7Hz, $N\underline{CH_2}(CH_2)_{10}CH_3$), 3.92 (3H, s, $-OCH_3$), 4.45, 5.05 (2H, ABq, J=15Hz, 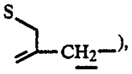), 5.20 (1H, d, J=5Hz, $C_6$—H), 5.80 (1H, dd, J=5Hz, J=8Hz, $C_7$—H), 6.15 (3H, bs, $-NH_3^{\oplus}$), 6.67 (2H, bs, 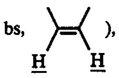), 6.88 (1H, s, 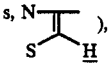), 9.75 (1H, d, J=8Hz, —CONH—) |
| 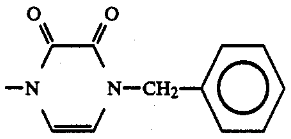 | H | 130-135 (decomp.) | 1770, 1670, 1635 | 3.52 (2H, bs, $C_2$—H), 3.91 (3H, s, $-OCH_3$), 4.41, 4.98 (2H, ABq, J=15Hz, 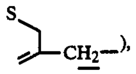), 4.95 (2H, s, $-\underline{CH_2}-$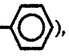), 5.19 (1H, d, J=5Hz, $C_6$—H), 5.82 (1H, dd, J=5Hz, J=8Hz, $C_7$—H), 6.15 (3H, bs, $-NH_3^{\oplus}$), 6.68 (2H, bs, 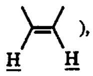), 6.90 (1H, s, 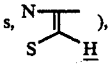), 7.35 (5H, bs, 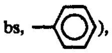), 9.75 (1H, d, J=8Hz, —CONH—) |
| 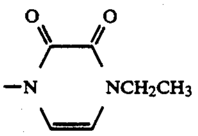 | Br | 147 (decomp.) | 1775, 1680, 1640 | 1.21 (3H, t, J=7Hz, $NCH_2\underline{CH_3}$), 3.50 (2H, bs, $C_2$—H), 3.81 (2H, q, J=7Hz, $N\underline{CH_2}CH_3$), 3.91 (3H, s, $-OCH_3$), 4.42, 5.10 (2H, ABq, J=15Hz, 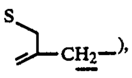), 5.19 (1H, d, J=5Hz, $C_6$—H), 5.95 (1H, dd, J=5Hz, J=8Hz, $C_7$—H), 6.67 (2H, bs, 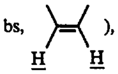), 9.64 (1H, d, J=8Hz, —CONH—) |

TABLE 19-continued

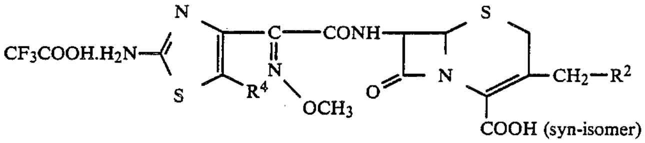
(syn-isomer)

| Compound | | | IR (KBr) | |
|---|---|---|---|---|
| $R^2$ | $R^4$ | m.p. (°C.) | $cm^{-1}$: $\nu_{C=O}$ | NMR ($d_6$-DMSO) δ values: |
| 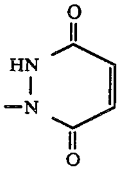 | H | 195-198 (decomp.) | 1775, 1710, 1690～1630 | 3.34 (2H, bs, $C_2$—H), 3.89 (3H, s, —$OCH_3$), 4.99 (2H, bs, 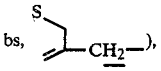), 5.12 (1H, d, J=5Hz, $C_6$—H), 5.75 (1H, dd, J=5Hz, J=8Hz, $C_7$—H), 6.84 (1H, s, 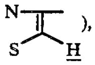), 6.89, 7.10 (2H, ABq, J=10Hz, 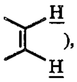), 9.70 (1H, d, J=8Hz, —CONH—) |
| 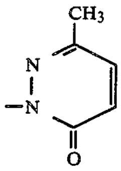 | H | 188-189 (decomp.) | 1770, 1710, 1680～1630 | 2.31 (3H, s, 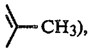—$CH_3$), 3.44 (2H, bs, $C_2$—H), 3.96 (3H, s, —$OCH_3$), 4.98, 5.40 (2H, ABq, J=15Hz, 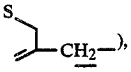), 5.23 (1H, d, J=5Hz, $C_6$—H), 5.88 (1H, dd, J=5Hz, J=8Hz, $C_7$—H), 6.17 (3H, bs, —$NH_3^{\oplus}$), 6.95 (1H, s, 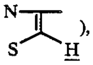), 7.00, 7.50 (2H, ABq, J=10Hz, 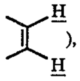), 9.87 (1H, d, J=8Hz, —CONH—) |
| 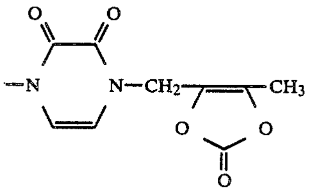 | H | 151-154 (decomp.) | 1820, 1775, 1685, 1640 | 2.22 (3H, s, —$CH_3$), 3.46 (2H, bs, $C_2$—H), 3.90 (3H, s, —$OCH_3$), 4.42, 5.05 (2H, ABq, J=15Hz, 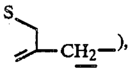), 4.78 (2H, s, $NCH_2$—), 5.18 (1H, d, J=5Hz, $C_6$—H), 5.80 (1H, dd, J=5Hz, J=8Hz, $C_7$—H), 6.64 (2H, s, 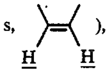), 6.84 (1H, s, 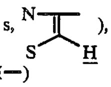), 9.78 (1H, d, J=8Hz, —CONH—) |
| 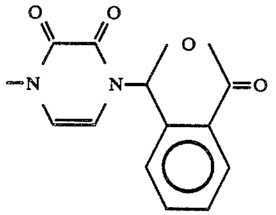 | H | 175-180 (decomp.) | 1770, 1700～1630 | 3.59 (2H, bs, $C_2$—H), 3.99 (3H, s, —$OCH_3$), 4.48, 5.19 (2H, ABq, J=15Hz, 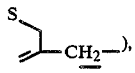), 5.27 (1H, d, J=5Hz, $C_6$—H), 5.94 (1H, dd, |

TABLE 19-continued

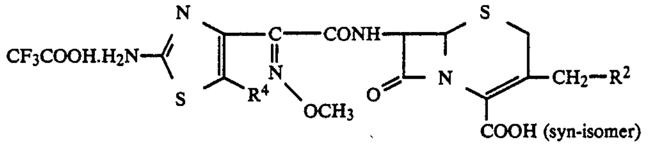

| Compound R² | R⁴ | m.p. (°C.) | IR (KBr) $cm^{-1}$: $\nu_{C=O}$ | NMR ($d_6$-DMSO) δ values: |
|---|---|---|---|---|
| | | | | J=5Hz, J=8Hz, $C_7$—H), 6.15, 6.68 (2H, ABq. J=6Hz, 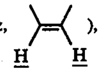 ), 6.99, (1H, s, 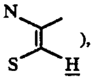 ), 7.66-8.19 (5H, m, 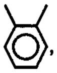, 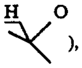 ), 9.92 (1H, d, J=8Hz, —CONH—) |
| 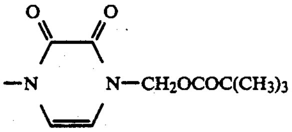 | H | 108-110 (decomp.) | 1780, 1730, 1690, 1650 | 1.18 (9H, s, —$C(CH_3)_3$), 3.54 (2H, bs, $C_2$—H), 3.98 (3H, s, —$OCH_3$), 4.49, 5.17 (2H, ABq, J=15Hz, 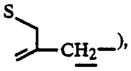 ), 5.29 (1H, d, J=5Hz, $C_6$—H), 5.77 (2H, s, $NCH_2$—), 5.90 (1H, dd, J=5Hz, J=8Hz, $C_7$—H), 6.79 (2H, bs, 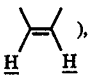 ), 7.02 (1H, s, 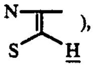 ), 9.99 (1H, d, J=8Hz, —CONH—) |
| 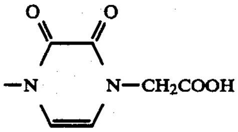 | H | 161-166 (decomp.) | 1770, 1680, 1640 | 3.51 (2H, bs, $C_2$—H), 3.96 (3H, s, —$OCH_3$), 4.52, 5.15 (2H, ABq, J=15Hz, 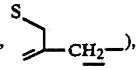 ), 4.54 (2H, s, $NCH_2$—), 5.27 (1H, d, J=5Hz, $C_6$—H), 5.88 (1H, dd, J=5Hz, J=8Hz, $C_7$—H), 6.75 (2H, s, 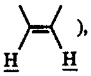 ), 6.98 (1H, s, 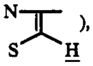 ), 9.92 (1H, d, J=8Hz, —CONH—) |

TABLE 20

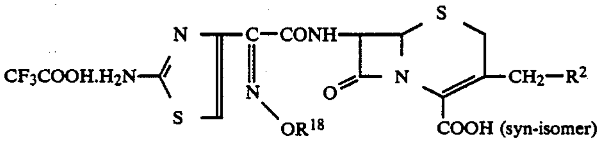

| Compound R² | $R^{18}$ | m.p. (°C.) | IR (KBr) $cm^{-1}$: $\nu_{C=O}$ | NMR ($d_6$-DMSO) δ values: |
|---|---|---|---|---|
| 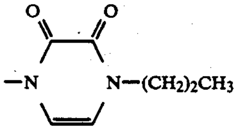 | —$CH_3$ | 165-167 (decomp.) | 1770, 1710~1630 | 0.90 (3H, t, J=7Hz, N—$CH_2CH_2CH_3$), 1.32-2.01 (2H, m, $NCH_2CH_2CH_3$), 3.53 (2H, bs, |

TABLE 20-continued

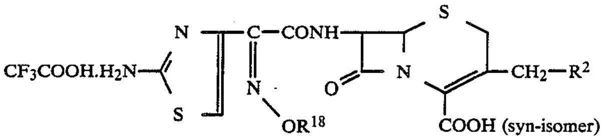

| Compound $R^2$ | $R^{18}$ | m.p. (°C.) | IR (KBr) $cm^{-1}$: $\nu_{C=O}$ | NMR ($d_6$-DMSO) δ values: |
|---|---|---|---|---|
| | | | | $C_2$—H), 3.73 (2H, t, J=7Hz, N—$CH_2CH_2CH_3$), 3.96 (3H, s, —$OCH_3$), 4.48, 5.14 (2H, ABq, J=15Hz, 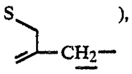 ), 5.14 (1H, d, J=5Hz, $C_6$—H), 5.91 (1H, dd, J=5Hz, J=8Hz, $C_7$—H), 6.24 (3H, bs, —$NH_3^{\oplus}$), 6.69 (2H, bs, 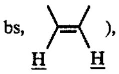 ), 6.92 (1H, s, 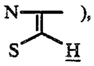 ), 9.82 (1H, d, J=8Hz, —CONH—) |
| 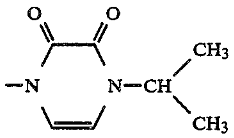 | —$CH_3$ | 160-162 (decomp.) | 1770, 1710~1630 | 1.25 (6H, d, J=7Hz, N—$CH(CH_3)_2$), 3.48 (2H, bs, $C_2$—H), 3.93 (3H, s, —$OCH_3$), 4.44, 5.08 (2H, ABq, J=15Hz, 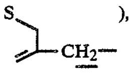 ), 4.64-5.12 (1H, m, N—$CH(CH_3)_2$), 5.21 (1H, d, J=5Hz, $C_6$—H), 5.86 (1H, dd, J=5Hz, J=8Hz, $C_7$—H), 6.36 (3H, bs, —$NH_3^{\oplus}$), 6.72 (2H, bs, 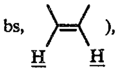 ), 6.91 (1H, s, 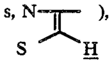 ), 9.79 (1H, d, J=8Hz, —CONH—) |
| 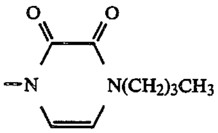 | —$CH_3$ | 155-157 (decomp.) | 1775, 1710, 1680~1630 | 0.89 (3H, t, J=7Hz, $N(CH_2)_3CH_3$), 1.03-1.93 (4H, m, N—$CH_2(CH_2)_2CH_3$), 3.49 (2H, bs, $C_2$—H), 3.74 (2H, t, J=7Hz, $NCH_2(CH_2)_2CH_3$), 3.92 (3H, s, —$OCH_3$), 4.41, 5.11 (2H, ABq, J=15Hz, 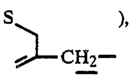 ), |

TABLE 20-continued

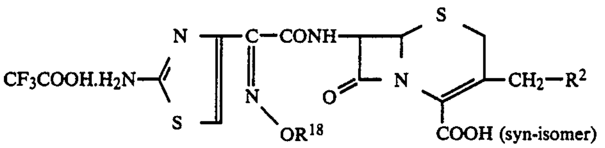

| Compound $R^2$ | $R^{18}$ | m.p. (°C.) | IR (KBr) $cm^{-1}$: $\nu_{C=O}$ | NMR ($d_6$-DMSO) δ values: |
|---|---|---|---|---|
| | | | | 5.21 (1H, d, J=5Hz, $C_6$—H), 5.81 (1H, dd, J=5Hz, J=8Hz, $C_7$—H), 6.65 (2H, bs, 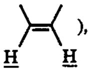), 6.87 (1H, s, 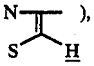), 7.26 (3H, bs, $-NH_3^{\oplus}$), 9.81 (1H, d, J=8Hz, —CONH—) |
| 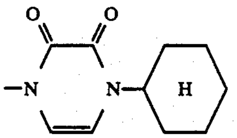 | $-CH_3$ | 175-177 (decomp.) | 1770, 1710~1630 | 0.86-2.06 (10H, m, 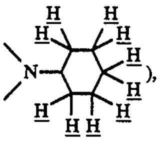), 3.45 (2H, bs, $C_2$—H), 3.87 (3H, s, $-OCH_3$), 4.20-4.71 (1H, m, 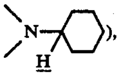), 4.36, 5.11 (2H, ABq, J=15Hz, 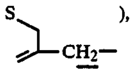), 5.14 (3H, bs, $-NH_3^{\oplus}$), 5.23 (1H, d, J=5Hz, $C_6$—H), 5.76 (1H, dd, J=5Hz, J=8Hz, $C_7$—H), 6.62 (2H, bs, 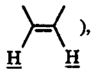), 6.80 (1H, s, 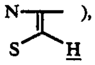), 9.66 (1H, d, J=8Hz, —CONH—) |
| 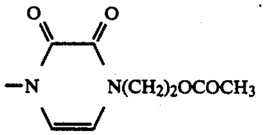 | $-CH_3$ | 105-107 (decomp.) | 1770, 1720, 1710~1630 | 1.97 (3H, s, $-OCOCH_3$), 3.44 (2H, bs, $C_2$—H), 3.80-4.42 (4H, m, $>N\underline{CH_2}\underline{CH_2}O-$), 3.91 (3H, s, $-OCH_3$), 4.41, 5.04 (2H, ABq, J=15Hz, 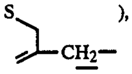), 5.15 (1H, d, J=5Hz, $C_6$—H), 5.79 (1H, dd, J=5Hz, J=8Hz, $C_7$—H), 6.59 (2H, bs, 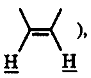), 6.88 (1H, s, 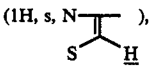), 7.38 (3H, bs, $-NH_3^{\oplus}$), 9.75 (1H, d, J=8Hz, —CONH—) |
| 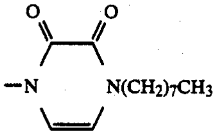 | $-CH_3$ | 131-135 (decomp.) | 1775, 1670, 1660, 1640 | 0.88 (3H, t, J=7Hz, $>N(CH_2)_7\underline{CH_3}$), 1.05-1.85 (12H, m, $>NCH_2\underline{(CH_2)_6}CH_3$), 3.53 (2H, bs, $C_2$—H), 3.73 (2H, t, J=7Hz, |

TABLE 20-continued

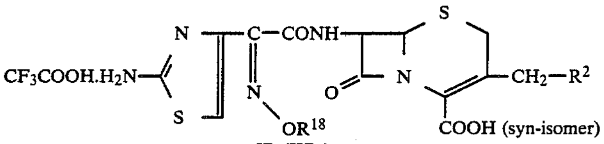

(syn-isomer)

| Compound R² | R¹⁸ | m.p. (°C.) | IR (KBr) $cm^{-1}$: $\nu_{C=O}$ | NMR ($d_6$-DMSO) δ values: |
|---|---|---|---|---|
| | | | | $NCH_2(CH_2)_6CH_3$), 3.96 (3H, s, $-OCH_3$), 4.48, 5.13 (2H, ABq, J=15Hz, 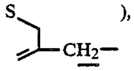 ), 5.25 (1H, d, J=5Hz, $C_6$—H), 5.88 (1H, dd, J=5Hz, J=8Hz, $C_7$—H), 6.72 (2H, bs, 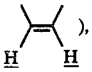 ), 6.98 (1H, s, 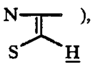 ), 7.21 (3H, bs, $-NH_3^{\oplus}$), 9.93 (1H, d, J=8Hz, —CONH—) |
| 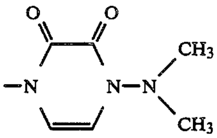 | $-CH_3$ | 179-181 (decomp.) | 1770, 1710, 1680～1620 | 2.86 (6H, s, 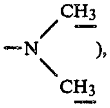 ), 3.51 (2H, bs, $C_2$—H), 3.39 (3H, s, $-OCH_3$), 4.42, 5.07 (2H, ABq, J=15Hz, 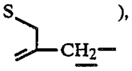 ), 5.22 (1H, d, J=5Hz, $C_6$—H), 5.96 (1H, dd, J=5Hz, J=8Hz, $C_7$—H), 6.57, 6.72 (2H, ABq, J=6Hz, 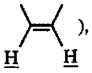 ), 6.90 (1H, s, 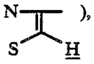 ), 7.44 (3H, bs, $-NH_3^{\oplus}$), 9.80 (1H, d, J=8Hz, —CONH—) |
| 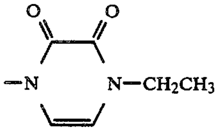 | $-CH_2CH_3$ | 169-174 (decomp.) | 1775, 1645 | 1.20 (3H, t, J=7Hz, $NCH_2CH_3$), 1.29 (3H, t, J=7Hz, $-OCH_2CH_3$), 3.52 (2H, bs, $C_2$—H), 3.47 (2H, q, J=7Hz, $N-CH_2CH_3$), 4.26 (2H, q, J=7Hz, $-OCH_2CH_3$), 4.45, 5.13 (2H, ABq, J=15Hz, 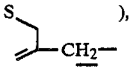 ), 5.26 (1H, d, J=5Hz, $C_6$—H), 5.90 (1H, dd, J=5Hz, J=8Hz, $C_7$—H), 6.70 (2H, bs, 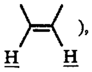 ), 6.95 (1H, s, 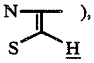 ), 9.86 (1H, d, J=8Hz, —CONH—) |

TABLE 20-continued

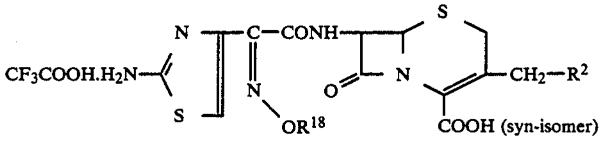

| Compound | | | IR (KBr) | |
|---|---|---|---|---|
| $R^2$ | $R^{18}$ | m.p. (°C.) | $cm^{-1}$: $\nu_{C=O}$ | NMR ($d_6$-DMSO) δ values: |
| 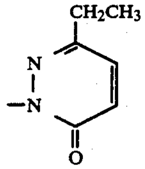 | $-CH_3$ | 153-156 (decomp.) | 1780, 1720, 1690~1630 | 1.17 (3H, t, J=7Hz, $\underline{CH_3}CH_2-$), 2.64 (2H, q, J=7Hz, $CH_3\underline{CH_2}-$), 3.46 (2H, bs, $C_2-H$), 3.96 (3H, s, $-OCH_3$), 4.96, 5.40 (2H, ABq, J=15Hz, 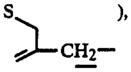), 5.23 (1H, d, J=5Hz, $C_6-H$), 5.88 (1H, dd, J=5Hz, J=8Hz, $C_7-H$), 6.95, 7.19 (2H, ABq, J=10Hz, 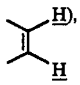), 6.97 (1H, s, 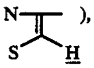), 7.59 (3H, bs, $-NH_3^{\oplus}$), 9.90 (1H, d, J=8Hz, $-CONH-$) |
| 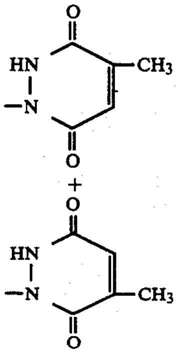 | $-CH_3$ | >200 | 1770, 1710, 1665 | 2.05 (1.5H, s, $-CH_3\times0.5$), 2.07 (1.5H, s, $-CH_3\times0.5$), 3.34 (2H, bs, $C_2-H$), 3.87 (3H, s, $-OCH_3$), 4.97 (2H, bs, 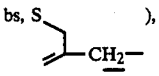), 5.09 (1H, d, J=5Hz, $C_6-H$), 5.73 (1H, dd, J=5Hz, J=8Hz, $C_7-H$), 6.77 (0.5H, s, 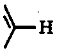 × 0.5), 6.80 (1H, s, 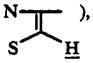), 6.94 (0.5H, s, 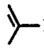×0.5), 7.75 (3H, bs, $-NH_3^{\oplus}$), 9.67 (1H, d, J=8Hz, $-CONH-$) |
| 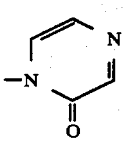 | $-CH_3$ | 144-147 (decomp.) | 1770, 1680~1640 | 3.43 (2H, bs, $C_2-H$), 3.87 (3H, s, $-OCH_3$), 4.51, 5.65 (2H, ABq, J=15Hz, 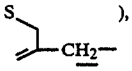), 5.14 (1H, d, J=5Hz, $C_6-H$), 5.78 (1H, dd, J=5Hz, J=8Hz, $C_7-H$), 6.80 (1H, s, 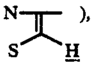), 7.31, 7.57 (2H, ABq, J=5Hz, 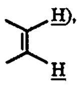), 7.98 (1H, s, 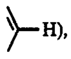), 9.66 (1H, d, J=8Hz, $-CONH-$) |

TABLE 20-continued

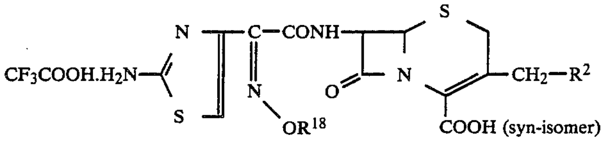

(syn-isomer)

| Compound R² | $R^{18}$ | m.p. (°C.) | IR (KBr) $cm^{-1}$: $\nu_{C=O}$ | NMR ($d_6$-DMSO) δ values: |
|---|---|---|---|---|
| 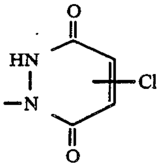 | $-CH_3$ | >200 | 1775, 1710, 1665~1630 | 3.40 (2H, bs, $C_2$—H), 3.90 (3H, s, $-OCH_3$), 4.87, 5.24 (2H, ABq, J=15Hz, 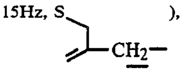), 5.06 (1H, d, J=5Hz, $C_6$—H), 5.78 (1H, dd, J=5Hz, J=8Hz, $C_7$—H), 6.84 (1H, s, 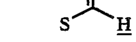), 7.44 (1H, s, 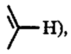H), 9.69 (1H, d, J=8Hz, —CONH—) |
| 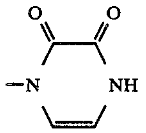 | $-CH_3$ | 168–170 (decomp.) | 1770, 1710~1630 | 3.50 (2H, bs, $C_2$—H), 3.95 (3H, s, $-OCH_3$), 4.47, 5.15 (2H, ABq, J=15Hz, 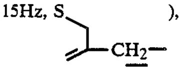), 5.24 (1H, d, J=5Hz, $C_6$—H), 5.85 (1H, dd, J=5Hz, J=8Hz, $C_7$—H), 6.46, 6.62 (2H, ABq, J=6Hz, 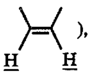), 6.94 (1H, s, 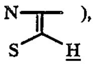), 7.03 (3H, bs, $-NH_3^{\oplus}$), 9.85 (1H, d, J=8Hz, —CONH—) |

(4) In 30 ml of water was dissolved 6.35 g of trifluoroacetic acid salt of 7-[2-(2-aminothiazol-4-yl)-2-(syn)-methoxyiminoacetamido]-3-{[1-(2,3-dioxo-1,2,3,4-tetrahydropyrazinyl)]methyl}-$\Delta^3$-cephem-4-carboxylic acid, and the resulting solution was adjusted to pH 7.4 with sodium hydrogencarbonate. Subsequently, this solution was purified by passing through an Amberlite XAD-2 column to obtain 4.7 g (yield, 86.6%) of sodium 7-[2-(2-aminothiazol-4-yl)-2-(syn)-methoxyiminoacetamido]-3-{[1-(2,3-dioxo-1,2,3,4-tetrahydropyrazinyl)]methyl}-$\Delta^3$-cephem-4-carboxylate having a melting point of 200° C. or more.

IR (KBr) $cm^{-1}$: $\nu_{C=O}$ 1763, 1670, 1650–1620.

In a similar manner, the following compounds were obtained:

Sodium 7-[2-(2-aminothiazol-4-yl)-2-(syn)-methoxyiminoacetamido]-3-{[1-(4-methyl-2,3-dioxo-1,2,3,4-tetrahydropyrazinyl)]methyl}-$\Delta^3$-cephem-4-carboxylate.

m.p.: 190°–195° C. (decomp.).

IR (KBr) $cm^{-1}$: $\nu_{C=O}$ 1760, 1670, 1650, 1630.

Sodium 7-[2-(2-aminothiazol-4-yl)-2-(syn)-methoxyiminoacetamido]-3-{[1-(3,6-dioxo-1,2,3,6-tetrahydropyridazinyl)]methyl}-$\Delta^3$-cephem-4-carboxylate Sodium 7-[2-(2-aminothiazol-4-yl)-2-(syn)-methoxyiminoacetamido]-3-{[1-(3-methyl-6-oxo-1,6-dihydropyridazinyl)]methyl}-$\Delta^3$-cephem-4-carboxylate.

EXAMPLE 7

(1) To a solution of 3 g of 2-(2-tritylaminothiazol-4-yl)-2-(syn)-tert.-butoxycarbonylmethoxyiminoacetic acid in 15 ml of N,N-dimethylacetamide was added dropwise 0.93 g of phosphorus oxychloride at −10° C., and the mixture was subjected to reaction at −5° to 0° C. for 1 hour. This solution was added dropwise to a solution of 19.4 ml of anhydrous methylene chloride containing 1.94 g of 7-amino-3-{[1-(4-ethyl-2,3-dioxo-1,2,3,4-tetrahydropyrazinyl)]-methyl}-$\Delta^3$-cephem-4-carboxylic acid and 2.25 g of bis(trimethylsilyl)acetamide at −5° to 0° C. After completion of th dropwise addition, the mixture was subjected to reaction at the same temperature for 30 minutes and then at 0° to 10° C. for 30 minutes. After completion of the reaction, methylene chloride was removed by distillation under reduced pressure, and to the residue was added a mixed solvent of 100 ml of saturated aqueous sodium chloride solution and 100 of acetonitrile. Subsequently, the organic layer was separated and washed twice with 50-ml portions of saturated aqueous sodium chloride solution, and then the solvent was removed by distillation under reduced pressure. The resulting residue was dissolved in 50 ml of methanol, after which 1 g of diphenyldiazomethane was added to the solution at 5° to 10° C., and the mixture was subjected to reaction at the same temperature for 30 minutes. After completion of the reaction, the solvent was removed by distillation under reduced pressure. The residue was purified by a column chromatography (Wako Silica Gel C-200, eluent; benzene:ethyl acetate=3:1) to obtain 1.6 g (yield, 27.8%) of diphenylmethyl 7-[2-(2-tritylaminothiazol-4-yl)-2-(syn)-tert.-butoxycarbonylmethoxyiminoacetamido]-3-{[1-(4-ethyl-2,3-dioxo-1,2,3,4-tetrahydropyrazinyl)]methyl}-

$\Delta^3$-cephem-4-carboxylate having a melting point of 98°-100° C. (decomp.).

IR (KBr) $cm^{-1}$: $\nu_{C=O}$ 1780, 1720, 1680, 1630.

NMR ($d_6$-DMSO) δ values: 1.17 (3H, t, J=7 Hz, >$NCH_2CH_3$), 1.44 (9H, s, —$C(CH_3)_3$), 3.62 (2H, bs, $C_2$—H), 3.74 (2H, q, J=7 Hz, >N—$CH_2CH_3$), 4.55 (2H, s,

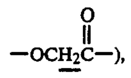

4.51, 5.16 (2H, ABq, J=15 Hz,

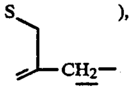

5.27 (1H, d, J=5 Hz, $C_6$—H), 5.87 (1H, dd, J=5 Hz, $C_7$—H), 6.55 (2H, bs,

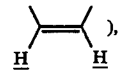

6.80 (1H, s, —C<), 6.97 (1H, s,

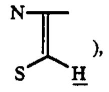

7.05-7.67 (25H, m, (25H, m, 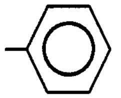 × 5), 8.86 (1H, bs,

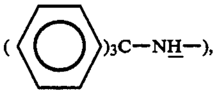

9.54 (1H, d, J=8 Hz, —CONH—)

In a similar manner, the compounds shown in Tables 21 and 22 were obtained.

TABLE 21

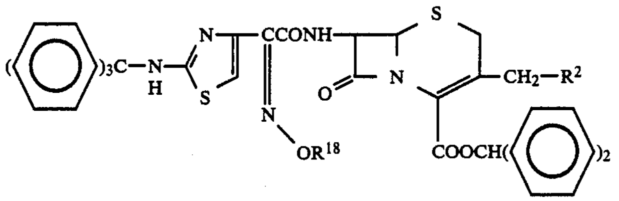

(syn-isomer)

| Compound | | | |
|---|---|---|---|
| $R^2$ | $R^{18}$ | m.p. (°C.) | IR (KBr) $cm^{-1}$: $\nu_{C=O}$ |
| 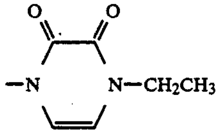 | 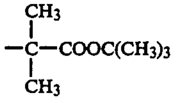 | 118-120 (decomp.) | 1780, 1720, 1690-1640 |
| 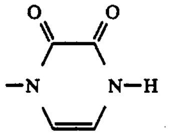 | $-CH_2COOC(CH_3)_3$ | 155-156 (decomp.) | 1780, 1720, 1680, 1640 |
| 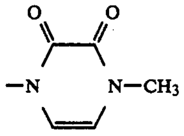 | $-CH_2COOC(CH_3)_3$ | 125-127 (decomp.) | 1785, 1725, 1690, 1645 |
| 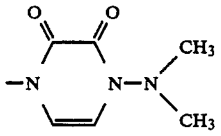 | $-CH_2COOC(CH_3)_3$ | 151-154 (decomp.) | 1780, 1725, 1685, 1640 |

TABLE 21-continued

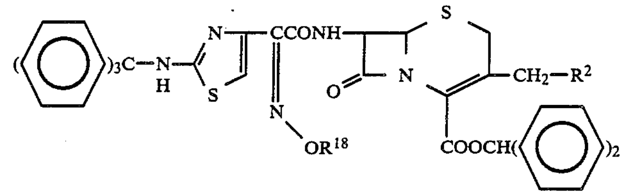

(syn-isomer)

| Compound R² | R¹⁸ | m.p. (°C.) | IR (KBr) cm⁻¹: $\nu_{C=O}$ |
|---|---|---|---|
| 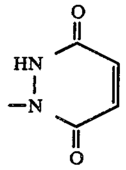 | $-CH_2COOC(CH_3)_3$ | 126-130 (decomp.) | 1780, 1725, 1690-1660 |
| 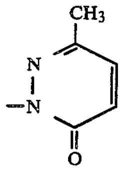 | $-CH_2COOC(CH_3)_3$ | 118-120 (decomp.) | 1780, 1720, 1660 |

TABLE 22

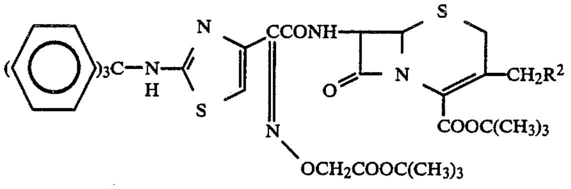

| Compound $R^2$ | m.p. (°C.) | IR (KBr) cm⁻¹: $\nu_{C=O}$ |
|---|---|---|
| 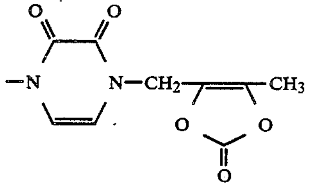 | 133-135 (decomp.) | 1820, 1780, 1720, 1690, 1650 |
| 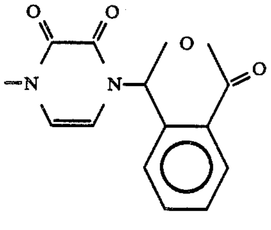 | 164-167 (decomp.) | 1785, 1730, 1710, 1690, 1660 |
| 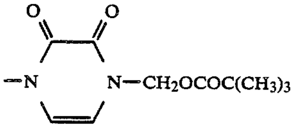 | 135-138 (decomp.) | 1785, 1740, 1730, 1710, 1680, 1660 |

TABLE 22-continued

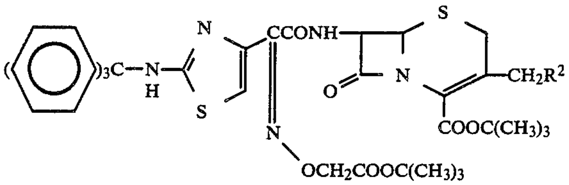

| Compound $R^2$ | m.p. (°C.) | IR (KBr) cm⁻¹: $\nu_{C=O}$ |
|---|---|---|
| 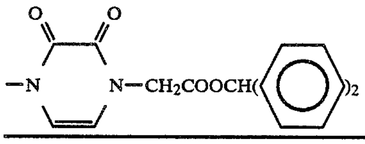 | 152-154 (decomp.) | 1785, 1750, 1720, 1690, 1655 |

(2) In a mixed solvent of 8 ml of trifluoroacetic acid and 3 ml of anisole was dissolved 1.6 g of diphenylmethyl 7-[2-(2-tritylaminothiazol-4-yl)-2-(syn)-tert.-butoxycarbonylmethoxyiminoacetamido]-3-{[1-(4-ethyl-2,3-dioxo-1,2,3,4-tetrahydropyrazinyl)]methyl}-$\Delta^3$-cephem-4-carboxylate, and the solution was subjected to reaction at room temperature for 1 hour. After completion of the reaction, the solvent was removed by distillation under reduced pressure. To the residue was added 10 ml of diethyl ether and the crystals were collected by filtration. Then, the crystals obtained were dissolved in 20 ml of 50% by weight aqueous formic acid solution, and the solution was subjected to reaction at 45° to 55° C. for 1 hour. After completion of the reaction, the precipitated crystals were separated by filtration, and the solvent was removed by distillation under reduced pressure. To the residue was added 10 ml of ethyl acetate and the crystals were collected by filtration. Subsequently, the crystals were sufficiently washed with 10 ml of ethyl acetate and dried to obtain 0.7 g (yield, 80.7%) of 7-[2-(2-aminothiazol-4-yl)-2-(syn)-carboxymethoxyiminoacetamido]-3-{[1-(4-ethyl-2,3-dioxo-1,2,3,4-tetrahydropyrazinyl)]methyl}-$\Delta^3$-cephem-4-carboxylic acid having a melting point of 139°-140° C. (decomp.).

IR (KBr) $cm^{-1}$: $\nu_{C=O}$ 1775, 1695, 1680, 1635.

NMR ($d_6$-DMSO) δ values: 1.22 (3H, t, J=7 Hz, $>NCH_2C\underline{H_3}$), 3.53 (2H, bs, $C_2$—H), 3.74 (2H, q, J=7 Hz, $>NC\underline{H_2}CH_3$), 4.70 (2H, s, $—OCH_2CO—$), 4.45, 5.10 (2H, ABq, J=15 Hz,

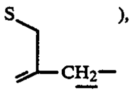), 5.23 (1H, d, J=5 Hz, $C_6$—H), 5.90 (1H, dd, J=5 Hz, J=8 Hz, $C_7$—H), 6.69 (2H, bs,

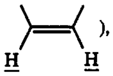), 6.94 (1H, s,

), 9.70 (1H, d, J=8 Hz, —CONH—)

In a similar manner, the compounds shown in Table 23 were obtained.

TABLE 23

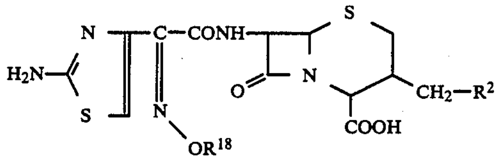

(syn-isomer)

| Compound $R^2$ | $R^{18}$ | m.p. (°C.) | IR(KBr) $cm^{-1}$: $\nu_{C=O}$ | NMR ($d_6$-DMSO) δ values: |
|---|---|---|---|---|
| 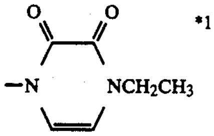 *1 | 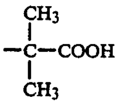 | 165-166 (decomp.) | 1775, 1705, 1690~1620 | 1.22 (3H, t, J=7Hz, $>NCH_2C\underline{H_3}$),<br>1.53 (6H, s, 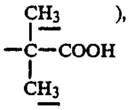),<br>3.54 (2H, bs, $C_2$—H), 3.75 (2H, q, J=7Hz, $>NC\underline{H_2}CH_3$), 4.49, 5.16 (2H, ABq, J=15Hz, 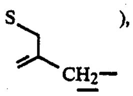),<br>5.27 (1H, d, J=5Hz, $C_6$—H), 6.01 (1H, dd, J=5Hz, J=8Hz, $C_7$—H),<br>6.72 (2H, bs, 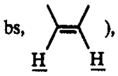), 6.96 (1H, s, 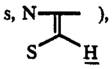), 9.64 (1H, d, J=8Hz, —CONH—), |
| 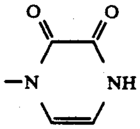 | $—CH_2COOH$ | 182-183 (decomp.) | 1770, 1690, 1670, 1640 | 3.44 (2H, bs, $C_2$—H), 4.42, 5.00 (2H, ABq, J=15Hz, 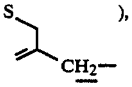),<br>4.60 (2H, bs, $—OC\underline{H_2}COOH$),<br>5.19 (1H, d, J=5Hz, $C_6$—H),<br>5.84 (1H, dd, J=5Hz, J=8Hz, $C_7$—H), 6.52 (2H, ABq, J=6Hz, |

TABLE 23-continued

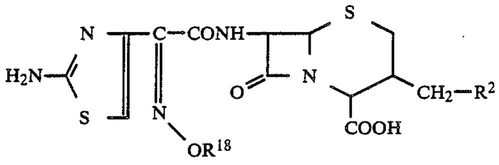

(syn-isomer)

| Compound $R^2$ | Compound $R^{18}$ | m.p. (°C.) | IR(KBr) $cm^{-1}$: $\nu_{C=O}$ | NMR ($d_6$-DMSO) δ values: |
|---|---|---|---|---|
| | | | | 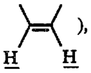 ), 6.82 (1H, s, 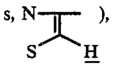 ),<br>9.56 (1H, d, J=8Hz, —CONH—) |
| 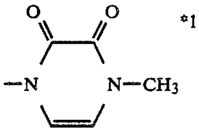 *1 | $-CH_2COOH$ | 88-91 (decomp.) | 1770, 1680, 1660, 1630 | 3.34 (3H, s, $>NCH_3$), 3.41 (2H, bs, $C_2$—H), 4.45, 5.02 (2H, ABq, J=15Hz, 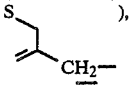 ), 4.67 (2H, bs, $-OCH_2COOH$), 5.16 (1H, d, J=5Hz, $C_6$—H), 5.84 (1H, dd, J=5Hz, J=8Hz, $C_7$—H), 6.60 (2H, bs, 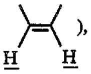 ), 6,97 (1H, s, 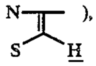 ),<br>9.75 (1H, d, J=8Hz, —CONH—) |
| 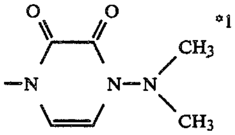 *1 | $-CH_2COOH$ | 155-158 (decomp.) | 1770, 1710, 1670, 1630 | 2.85 (6H, s, 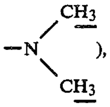 ), 3.49 (2H, bs, $C_2$—H), 4.43, 4.98 (2H, ABq, J=15Hz, 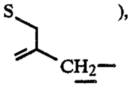 ), 4.65 (2H, s, $-OCH_2CO-$), 5.15 (1H, d, J=5Hz, $C_6$—H), 5.79 (1H, dd, J=5Hz, J=8Hz, $C_7$—H), 6.61 (1H, bs, 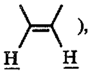 ), 6.91 (1H, s, 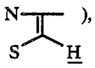 ),<br>9.65 (1H, d, J=8Hz, —CONH—), |
| 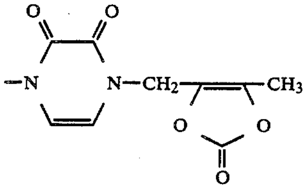 | $-CH_2COOH$ | 151-154 (decomp.) | 1820, 1770, 1680, 1640 | 2.22 (3H, s, $-CH_3$), 3.50 (2H, bs, $C_2$—H), 4.70 (2H, s, $>NCH_2-$), 4.85 (4H, bs, $-OCH_2CO-$, 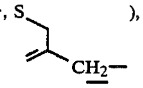 ), 5.27 (1H, d, J=5Hz, $C_6$—H), 5.94 (1H, dd, J=5Hz, J=8Hz), $C_7$—H), 6.75 (2H, s, 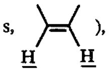 ), 6.97 (1H, s, 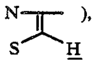 ), 9.81 (1H, d, J=8Hz, —CONH—) |

TABLE 23-continued

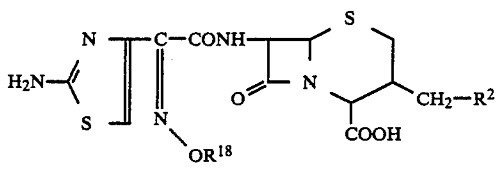

(syn-isomer)

| Compound | | | IR(KBr) | |
|---|---|---|---|---|
| $R^2$ | $R^{18}$ | m.p. (°C.) | $cm^{-1}$: $\nu_{C=O}$ | NMR ($d_6$-DMSO) δ values: |
| 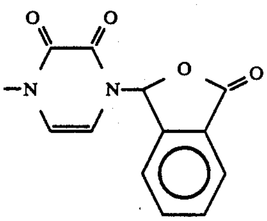 | $-CH_2COOH$ | 137-140 (decomp.) | 1785, 1720, 1690, 1640 | 3.75 (2H, bs, $C_2$—H), 4.47, 5.13 (2H, ABq, J=15Hz, 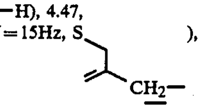 ), 4.74 (2H, s, $-OCH_2CO-$), 5.13 (1H, d, J=5Hz, $C_6$—H), 5.97 (1H, dd, J=5Hz, J=8Hz, $C_7$—H), 6.12, 6.66 (2H, ABq, J=6Hz, 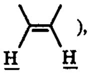 ), 7.05 (1H, s, 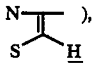 ), 7.61-8.25 (5H, m, 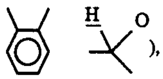 ), 8.84 (1H, d, J=8Hz, —CONH—) |
| 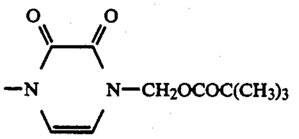 | $-CH_2COOH$ | 178-183 (decomp.) | 1790, 1730, 1690, 1650 | 1.17 (9H, s, $-C(CH_3)_3$), 3.72 (2H, bs, $C_2$—H), 4.46, 5.20 (2H, ABq, J=15Hz, 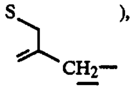 ), 4.70 (2H, s, $-OCH_2CO-$), 5.03 (1H, d, J=5Hz, $C_6$—H), 5.73 (2H, s, 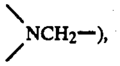), 6.06 (1H, dd, J=5Hz, J=8Hz, $C_7$—H), 6.73 (2H, bs, 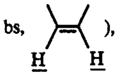 ), 7.05 (1H, s, 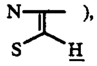 ), 8.87 (1H, d, J=8Hz, —CONH—) |
| 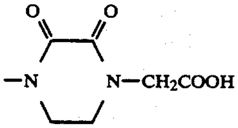 | $-CH_2COOH$ | 135-142 (decomp.) | 1780, 1720, 1680, 1635 | 3.73 (2H, bs, $C_2$—H), 4.48, 5.28 (2H, ABq, J=15Hz, 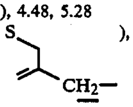 ), 4.54 (2H, s, 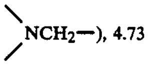), 4.73 (2H, s, $-OCH_2CO-$), 5.10 (1H, d, J=5Hz, $C_6$—H), 6.07 (1H, dd, J=5Hz, J=8Hz, $C_7$—H), 6.74 (2H, bs, 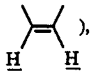 ), 7.05 (1H, s, 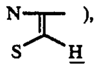 ), 8.89 (1H, d, J=8Hz, —CONH—) |

TABLE 23-continued

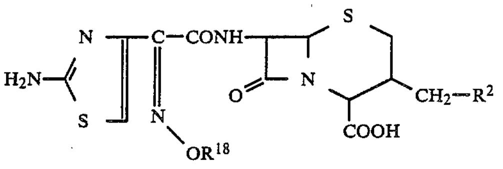

(syn-isomer)

| Compound R² | R¹⁸ | m.p. (°C.) | IR(KBr) $cm^{-1}$: $\nu_{C=O}$ | NMR ($d_6$-DMSO) δ values: |
|---|---|---|---|---|
| 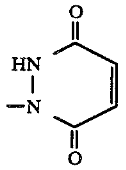 *2 | $-CH_2COOH$ | 190-193 (decomp.) | 1770, 1710, 1660, 1630 | 3.34 (2H, bs, $C_2$—H), 4.63 (2H, s, $-OCH_2CO-$), 4.98 (2H, bs, 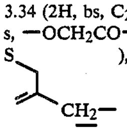 ), 5.10 (1H, d, J=5Hz, $C_6$—H), 5.77 (1H, dd, J=5Hz, J=8Hz, $C_7$—H), 6.83 (1H, s, 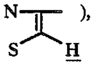 ), 6.85, 7.11 (2H, ABq, J=10Hz, 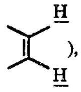 ), 9.51 (1H, d, J=8Hz, —CONH—) |
| 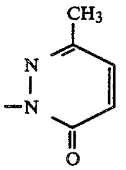 *2 | $-CH_2COOH$ | 194-197 (decomp.) | 1770, 1710, 1690~1630 | 2.28 (3H, s, 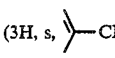), 3.43 (2H, bs, $C_2$—H), 4.73 (2H, s, $-OCH_2CO-$), 5.14 (1H, d, J=5Hz, $C_6$—H), 5.23 (2H, bs, 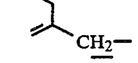 ), 5.88 (1H, dd, J=5Hz, J=8Hz, $C_7$—H), 6.96, 7.46 (2H, ABq, J=10Hz, 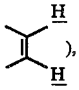 ), 7.01 (1H, s, 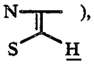 ), 7.80 (3H, bs, $-NH_3^{\oplus}$), 9.76 (1H, d, J=8Hz, —CONH—) |

Note:
*1 Trifluoroacetic acid salt (For the purpose of purifying the product obtained by the above-mentioned procedure, it was converted to a diphenylmethyl ester in a conventional manner, followed by de-esterification with trifluoroacetic acid to obtain a trifluoroacetic acid salt.)
*2 Formate

EXAMPLE 8

(1) To a solution of 1.68 g of diketene in 8.40 ml of anhydrous methylene chloride was added dropwise a solution of 2.08 g of bromine in 6.25 ml of anhydrous methylene chloride with stirring at −30° C., and the mixture was subjected to reaction at −30° to −20° C. for 30 minutes. The thus obtained reaction mixture was addded dropwise at −30° C. or less to a solution of 50 ml of anhydrous methylene chloride containing 5.20 g of diphenylmethyl 7-amino-3-{[1-(4-ethyl-2,3-dioxo-1,2,3,4-tetrahydropyrazinyl)]methyl}-$\Delta^3$-cephem-4-carboxylate and 4.08 g of bis(trimethylsilyl)acetamide.

After completion of the dropwise addition, the mixture was subjected to reaction at −30° to −20° C. for 30 minutes and then at 0° to 10° C. for 1 hour. After completion of the reaction, the solvent was removed by distillation under reduced pressure, and the residue thus obtained was dissolved in 50 ml of ethyl acetate and 40 ml of water. Then the organic layer was separated, washed with 40 ml of water and 40 ml of a saturated aqueous sodium chloride solution in this order, and dried over anhydrous magnesium sulfate. The solvent was removed by distillation under reduced pressure. To the residue was added 50 ml of diisopropyl ether, and the thus obtained crystals were collected by filtration to obtain 5.85 g (yield, 85.6%) of diphenylmethyl 7-(4-bromo-3-oxobutyramido)-3-{[1-(4-ethyl-2,3-dioxo-1,2,3,4-tetrahydropyrazinyl)]methyl}-$\Delta^3$-cephem-4-carboxylate having a melting point of 138°-142° C. (decomp.).

IR (KBr) $cm^{-1}$: $\nu_{C=O}$ 1778, 1720, 1680, 1640.

NMR ($d_6$-DMSO) δ values: 1.22 (3H, t, J=7 Hz, $>NCH_2C\underline{H_3}$), 3.40 (2H, bs, $C_2$—H), 3.85 (2H, q, J=7 Hz, $>NC\underline{H_2}CH_3$), 3.87 (2H, bs, $BrCH_2COC\underline{H_2}-$), 4.18 (2H, bs, $BrC\underline{H_2}CO-$), 4.47, 4.96 (2H, ABq, J=15 Hz,

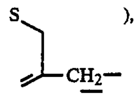

), 5.04 (1H, d, J=5 Hz, $C_6$—H), 5.90 (1H, dd, J=5 Hz, J=8 Hz, $C_7$—H), 6.15, 6.50 (2H, ABq, J=6 Hz,

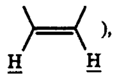

), 6.98 (1H, s, —CH>), 7.40 (10H, bs,

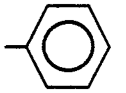

× 2), 8.55 (1H, d, J=8 Hz, —CONH—).

In a similar manner, the following compound was obtained:

4.09 g (yield, 62.6%) of diphenylmethyl 7-(4-bromo-3-oxobutyramido)-3-{[1-(3,6-dioxo-1,2,3,6-tetrahydropyridazinyl)]methyl}-$\Delta^3$-cephem-4-carboxylate having a melting point of 124°-126° C. (decomp.).

IR (KBr) $cm^{-1}$: $\nu_{C=O}$ 1780, 1725, 1660.

NMR ($d_6$-DMSO) δ values: 3.49 (4H, bs, $C_2$—H, $$-\overset{O}{\overset{\|}{C}}CH_2\overset{O}{\overset{\|}{C}}-),$$

4.52 (2H, s, $$BrCH_2\overset{O}{\overset{\|}{C}}-),$$

5.06 (1H, bs,

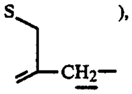

), 5.26 (1H, d, J=5 Hz, $C_6$—H), 5.90 (1H, dd, J=5 Hz, J=8 Hz, $C_7$—H), 7.01, 7.25 (2H, ABq, J=10 Hz,

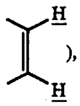

), 7.09 (1H, s, —CH<), 7.24-7.91 (10H, m,

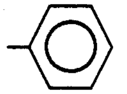

× 2), 9.34 (1H, d, J=10 Hz, —CONH—).

(2) To a solution of 5.50 g of diphenylmethyl 7-(4-bromo-3-oxobutyramido)-3-{[1-(4-ethyl-2,3-dioxo-1,2,3,4-tetrahydropyrazinyl)]methyl}-$\Delta^3$-cephem-4-carboxylate in 30 ml of acetic acid was added dropwise a solution of 5 ml of water containing 0.74 g of sodium nitrite with ice-cooling over a period of 1 hour, and the resulting mixture was subjected to reaction at room temperature for 2 hours. After completion of the reaction, the reaction mixture was poured into 500 ml of water to precipitate crystals. The crystals were collected by filtration, washed sufficiently with water, and dried. Then, the crystals were dissolved in 10 ml of chloroform and then purified by a column chromatography (Wako Silica Gel C-200, eluent; benzene:ethyl acetate=2:1 by volume), to obtain 3.15 g (yield, 54.9%) of diphenylmethyl 7-(4-bromo-2-hydroxyimino-3-oxobutyramido)-3-{[1-(4-ethyl-2,3-dioxo-1,2,3,4-tetrahydropyrazinyl)]methyl}-$\Delta^3$-cephem-4-carboxylate having a melting point of 127°-132° C. (decomp.)

IR (KBr) $cm^{-1}$: $\nu_{C=O}$ 1778, 1720, 1680, 1635.

NMR ($CDCl_3$) δ values: 1.26 (3H, t, J=7 Hz, >$NCH_2\underline{CH_3}$), 3.47 (2H, bs, $C_2$—H), 3.81 (2H, q, J−7 Hz, >$N\underline{CH_2}CH_3$), 4.52 (2H, s, $Br\underline{CH_2}CO$—), 4.53, 4.78 (2H, ABq, J=15 Hz,

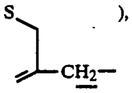

), 5.11 (1H, d, J=5 Hz, $C_6$—H), 5.80-6.15 (1H, m, $C_7$—H), 6.13, 6.52 (2H, ABq, J=6 Hz,

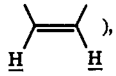

), 7.02 (1H, s, —CH<), 7.41 (10H, bs,

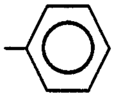

× 2), 9.20 (1H, d, J=8 Hz, —CONH—)

In a similar manner, the following compound was obtained:

4.71 g (yield, 75.1%) of diphenylmethyl 7-(4-bromo-2-hydroxyimino-3-oxobutyramido(-3-{[1-(3,6-dioxo-1,2,3,6-tetrahydropyridazinyl)]methyl}-$\Delta^3$-cephem-4-carboxylate having a melting point of 138°-141° C. (decomp.)

IR (KBr) $cm^{-1}$: $\nu_{C=O}$ 1780, 1720, 1660.

NMR ($d_6$-DMSO) δ values: 3.46 (2H, bs, $C_2$—H), 4.62 (2H, s, $BrCH_2CO$—) 4.96 (2H, bs,

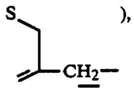

), 5.18 (1H, d, J=5 Hz, $C_6$—H), 5.93 (1H, dd, J=5 Hz, J=8 Hz, $C_7$—H), 6.89, 7.13 (2H, ABq, J=10 Hz,

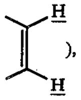

6.96 (1H, s, —CH<), 7.13–7.72 (10H, m,

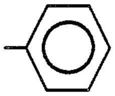 × 2), 9.45 (1H, d, J=8 Hz, —CONH—), 13.36 (1H, s, =N—OH)

(3) In 12 ml of N,N-dimethylacetamide were dissolved 3.00 g of the diphenylmethyl 7-(4-bromo-2-hydroxyimino-3-oxobutyramido)-3-{[1-(4-ethyl-2,3-dioxo-1,2,3,4-tetrahydropyrazinyl)]methyl}-$\Delta^3$-cephem-4-carboxylate obtained in above (2) and 0.42 g of thiourea, and the resulting solution was subjected to reaction at room temperature for 3 hours. After completion of the reaction, the reaction mixture was poured into a mixed solvent of 120 ml of water and 240 ml of ethyl acetate. Subsequently, the mixture was adjusted to pH 7.0 with sodium hydrogencarbonate, after which the organic layer was separated, and washed with 50 ml of water and 50 ml of a saturated aqueous sodium chloride solution in this order. After the organic layer was dried over anhydrous magnesium sulfate, the solvent was removed by distillation under reduced pressure. To the residue was added 20 ml of diethyl ether and the crystals were collected by filtration to obtain 2.10 g (yield, 72.3%) of diphenylmethyl 7-[2-(2-aminothiazol-4-yl)-2-(syn)-hydroxyiminoacetamido]-3-{[1-(4-ethyl-2,3-dioxo-1,2,3,4-tetrahydropyrazinyl)]methyl}-$\Delta^3$-cephem-4-carboxylate having a melting point of 137°–140° C. (decomp.).

IR (KBr) $cm^{-1}$: $\nu_{C=O}$ 1778, 1720, 1680, 1640.

NMR ($d_6$-DMSO) δ values: 1.19 (3H, t, J=7 Hz, >$NCH_2C\underline{H_3}$), 3.48 (2H, bs, $C_2$—H), 3.68 (2H, q, J=7 Hz, >$NC\underline{H_2}CH_3$), 4.46, 5.04 (2H, ABq, J=15 Hz,

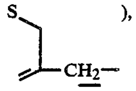

5.28 (1H, d, J=5 Hz, $C_6$—H), 5.97 (1H, dd, J=5 Hz, J=8 Hz, $C_7$—H), 6.57, 6.75 (2H, ABq, J=6 Hz,

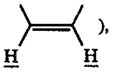

6.79 (1H, s,

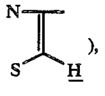

7.07 (1H, s, —CH<), 7.53 (10H, bs,

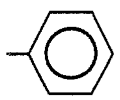 × 2), 9.70 (1H, d, J=8 Hz, —CONH—).

In a mixed solvent of 10.0 ml of trifluoroacetic acid and 2.0 ml of anisole was dissolved 2.00 g of the diphenylmethyl 7-[2-(2-aminothiazol-4-yl)-2-(syn)-hydroxyiminoacetamido]-3-{[1-(4-ethyl-2,3-dioxo-1,2,3,4-tetrahydropyrazinyl)]methyl}-$\Delta^3$-cephem-4-carboxylate obtained in above (3), and the resulting solution was subjected to reaction at room temperature for 2 hours. After completion of the reaction, the solvent was removed by distillation under reduced pressure, and to the residue was added 15 ml of diethyl ether, after which the crystals were collected by filtration. Subsequently, the crystals were sufficiently washed with 10 ml of diethyl ether and then dried to obtain 1.62 g (yield, 87.6%) of trifluoroacetic acid salt of 7-[2-(2-aminothiazol-4-yl)-2-(syn)-hydroxyiminoacetamido]-3-{[1-(4-ethyl-2,3-dioxo-1,2,3,4-tetrahydropyrazinyl)]methyl}-$\Delta^3$-cephem-4-carboxylic acid having a melting point of 112°–118° C. (decomp.).

IR (KBr) $cm^{-1}$: $\nu_{C=O}$ 1780, 1680, 1620.

NMR ($d_6$-DMSO) δ values: 1.19 (3H, t, J=7 Hz, >$N—CH_2C\underline{H_3}$), 3.47 (2H, bs, $C_2$—H), 3.72 (2H, q, J=7 Hz, >$NC\underline{H_2}CH_3$), 4.45–6.70 (4H, m,

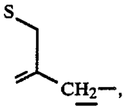

$C_6$—H, $C_7$—H), 6.59–6.83 (3H, m,

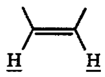 , 

EXAMPLE 9

(1) To a solution of 7.1 g of diphenylmethyl 7-(4-bromo-2-hydroxyimino-3-oxobutyramido)-3-{[1-(4-ethyl-2,3-dioxo-1,2,3,4-tetrahydropyrazinyl)]methyl}-$\Delta^3$-cephem-4-carboxylate in 70 ml of anhydrous methylene chloride was slowly added a solution of diazomethane in diethyl ether at −5° to 0° C., and the resulting solution was subjected to reaction at the same temperature for 30 minutes. After confirming the disappearance of diazomethane, the solvent was removed by distillation under reduced pressure. Then, the obtained residue was purified by a column chromatography (Wako Silica Gel C-200, eluent; benzene:ethyl acetate=3:1 by volume) to obtain 2.32 g (yield, 32.0%) of diphenylmethyl 7-[4-bromo-2-(syn)-methoxyimino-3-oxobutyramido]-3-{[1-(4-ethyl-2,3-dioxo-1,2,3,4-tetrahydropyrazinyl)]methyl}-$\Delta^3$-cephem-4-carboxylate having a melting point of 135°–140° C. (decomp.).

IR (KBr) $cm^{-1}$: $\nu_{C=O}$ 1778, 1720, 1682, 1638.

NMR ($CDCl_3$) δ values: 1.25 (3H, t, J=7 Hz, $>NCH_2C\underline{H_3}$), 3.48 (2H, bs, $C_2$—H), 3.84 (2H, q, J=7 Hz, $>NC\underline{H_2}CH_3$), 4.00 (3H, s, $—OCH_3$), 4.10 (2H, s, $BrC\underline{H_2}CO—$), 4.48, 4.67 (2H, ABq, J=15 Hz,

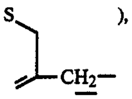
), 5.10 (1H, d, J=5 Hz, $C_6$—H), 6.05 (1H, dd, J=5 Hz, J=8 Hz, $C_7$—H), 6.38, 6.73 (2H, ABq, J=6 Hz,

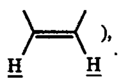
), 6.98 (1H, s, —CH<), 7.32 (10H, bs,

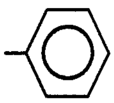
× 2), 9.18 (1H, d, J=8 Hz, —CONH—).

In a similar manner, the following compound was obtained:

1.70 g (yield, 24.5%) of diphenylmethyl 7-[4-bromo-2-(syn)-methoxyimino-3-oxobutyramido]-3-{[1-(3,6-dioxo-1,2,3,6-tetrahydropyridazinyl)]methyl}-$\Delta^3$-cephem-4-carboxylate having a melting point of 145°-148° C. (dec.).

IR (KBr) $cm^{-1}$: $\nu_{C=O}$ 1780, 1730, 1660.

NMR ($d_6$-DMSO) δ values: 3.49 (2H, bs, $C_2$—H), 4.03 (3H, s, $—OCH_3$), 4.60 (2H, s, $BrCH_2CO—$), 5.02 (2H, bs,

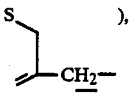
), 5.30 (1H, d, J=5 Hz, $C_6$—H), 6.02 (1H, dd, J=5 Hz, J=8 Hz, $C_7$—H), 6.92, 7.16 (2H, ABq, J=10 Hz,

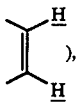
), 6.99 (1H, s, —CH<), 7.17-7.78 (10H, m,

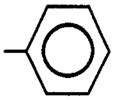
× 2), 10.16 (1H, d, J=8 Hz, —CONH—)

(2) In 14 ml of N,N-dimethylacetamide were dissolved 2.3 g of diphenylmethyl 7-[4-bromo-2-(syn)-methoxyimino-3-oxobutyramido]-3-{[1-(4-ethyl-2,3-dioxo-1,2,3,4-tetrahydropyrazinyl)]methyl}-$\Delta^3$-cephem-4-carboxylate and 0.32 g of thiourea, and the resulting solution was subjected to reaction at room temperature for 3 hours. After completion of the reaction, the reaction mixture was poured into a mixed solvent of 50 ml of water and 150 ml of ethyl acetate. Then, sodium hydrogencarbonate was added thereto adjust the mixture to pH 6.7, and then the organic layer was separated. The aqueous layer was further extracted twice with 100-ml portions of ethyl acetate. The combined organic layer was washed with water and dried over anhydrous magnesium sulfate, and the solvent was removed by distillation under reduced pressure. To the residue was added 20 ml of diethyl ether, and the crystals were collected by filtration to obtain 1.92 g (yield, 86.3%) of diphenylmethyl 7-[2-(2-aminothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylate having a melting point of 165°-167° C.

IR (KBr) $cm^{-1}$: $\nu_{C=O}$ 1780, 1720, 1680, 1640.

In a similar manner, the following compound was obtained:

Diphenylmethyl 7-[2-(2-aminothiazol-4-yl-2-(syn)-methoxyiminoacetamido]-3-{[1-(3,6-dioxo-1,2,3,6-tetrahydropyridazinyl)]methyl}-$\Delta^3$-cephem-4-carboxylate, m.p., 175°-178° C. (decomp.).

IR (KBr) $cm^{-1}$: $\nu_{C=O}$ 1780, 1720, 1685-1660.

The same ring-closure reaction as above was conducted and then the reaction mentioned in Example 6-(3) or Example 7-(2) was conducted, to obtain the compounds shown in Tables 24, 25 and 26.

TABLE 24
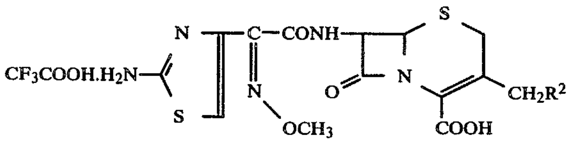
(syn-isomer)
| $R^2$ | $R^2$ | $R^2$ | $R^2$ | $R^2$ |
|---|---|---|---|---|
| 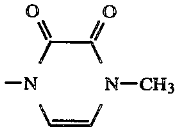 | 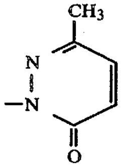 | 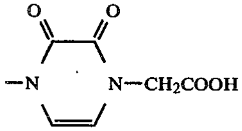 | 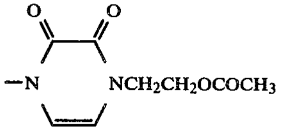 | 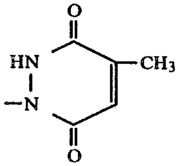 + 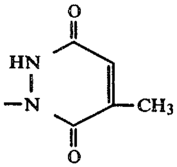 |
| 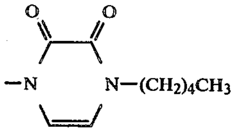 | 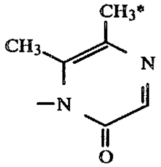 | 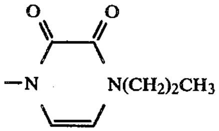 | 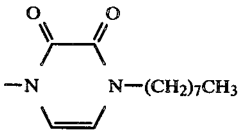 | 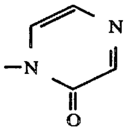 |
| 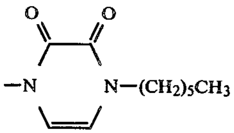 | 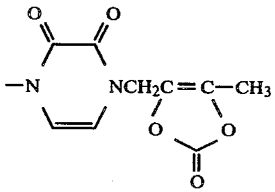 | 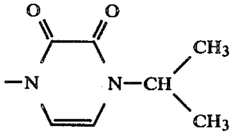 | 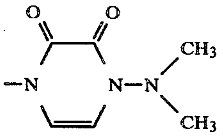 | 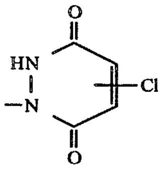 |
| 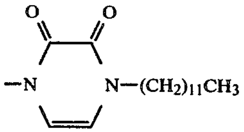 | 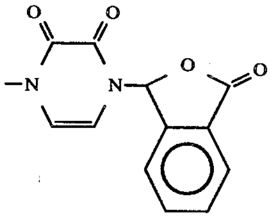 | 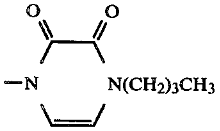 | 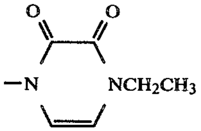 | 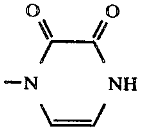 |

TABLE 24-continued
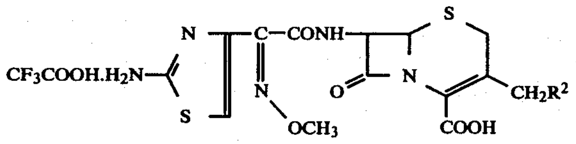
(syn-isomer)
| $R^2$ | $R^2$ | $R^2$ | $R^2$ | $R^2$ |
|---|---|---|---|---|
| 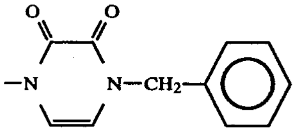 | 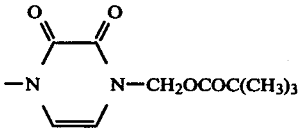 | 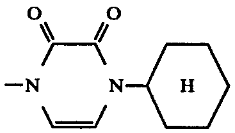 | 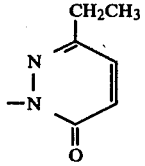 | 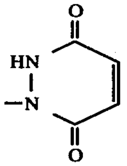 |
Note:
*Hydrochloride TABLE 25
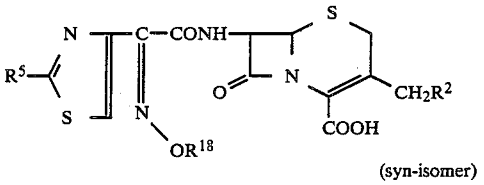
(syn-isomer)
| $R^2$ | $R^5$ | $R^{18}$ |
|---|---|---|
| 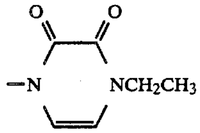 | $NH_2-$ | $-CH_2COOH$ |
| 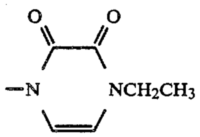 | $CF_3COOH.NH_2-$ | 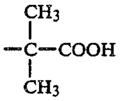 |
| 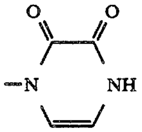 | $NH_2-$ | $-CH_2COOH$ |
| 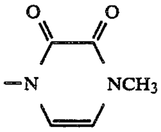 | $CF_3COOH.NH_2-$ | $-CH_2COOH$ |
| 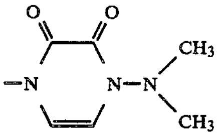 | $CF_3COOH.NH_2-$ | $-CH_2COOH$ |
| 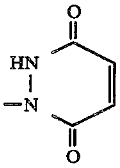 | $HCOOH.NH_2-$ | $-CH_2COOH$ |
| 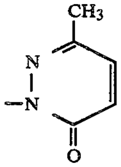 | $HCOOH.NH_2-$ | $-CH_2COOH$ |
| 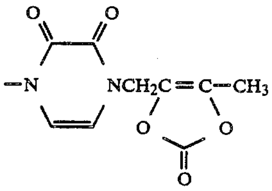 | $NH_2-$ | $-CH_2COOH$ |

TABLE 25-continued
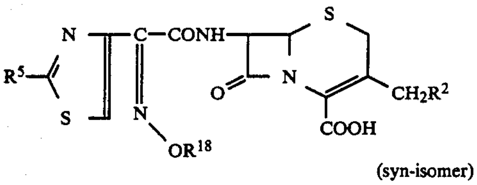
(syn-isomer)
| $R^2$ | $R^5$ | $R^{18}$ |
|---|---|---|
| 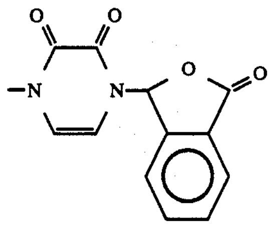 | $NH_2$— | $-CH_2COOH$ |
| 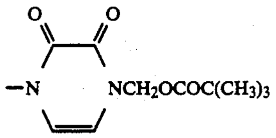 | $NH_2$— | $-CH_2COOH$ |
| 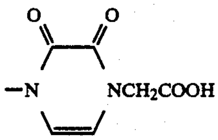 | $NH_2$— | $-CH_2COOH$ |
| 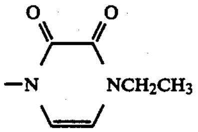 | HCOOH.$NH_2$— | 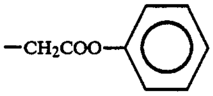 |
| 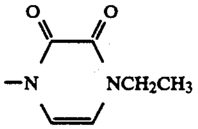 | HCOOH.$NH_2$— | 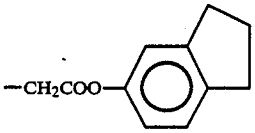 |
| 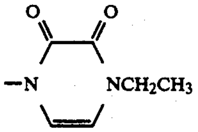 | HCOOH.$NH_2$— | $-CH_2COOCH_2CH_3$ |
TABLE 26
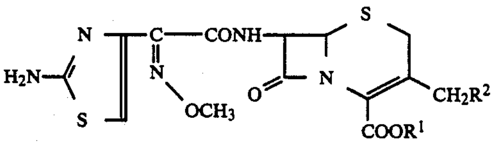
(syn-isomer)
| $R^1$ | $R^2$ |
|---|---|
| 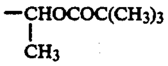 | 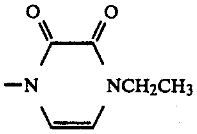 |
TABLE 26-continued
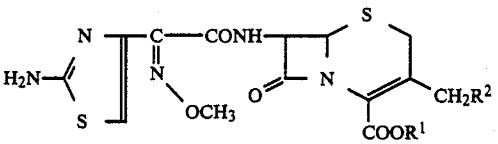
(syn-isomer)
| $R^1$ | $R^2$ |
|---|---|
| 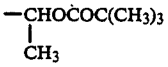 | 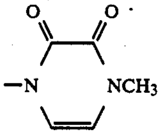 |

TABLE 26-continued

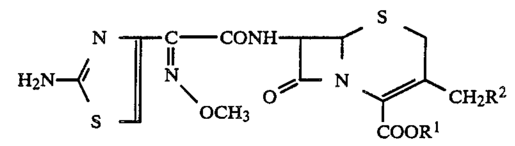

(syn-isomer)

| $R^1$ | $R^2$ |
|---|---|
| $-\underset{\mid}{C}HOCOC(CH_3)_3$ $CH_3$ | 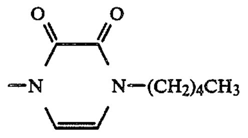 |
| $-\underset{\mid}{C}HOCOC(CH_3)_3$ $CH_3$ | 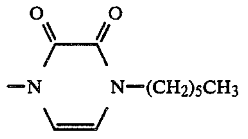 |
| $-\underset{\mid}{C}HOCOC(CH_3)_3$ $CH_3$ | 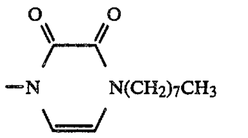 |
| $-\underset{\mid}{C}HOCOC(CH_3)_3$ $CH_3$ | 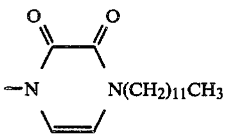 |
| $-CH_2OCOC(CH_3)_3$ | 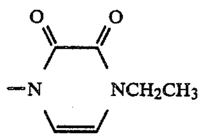 |
| $-\underset{\mid}{C}HOCOOC(CH_3)_3$ $CH_3$ | 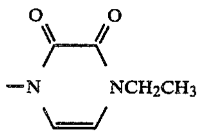 |
| 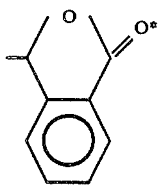 | 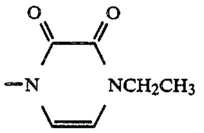 |
| $-(CH_2)_3CH_3$ | 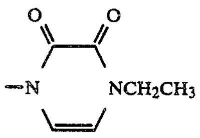 |
| 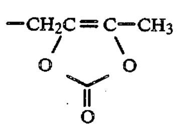 | 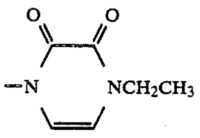 |

TABLE 26-continued

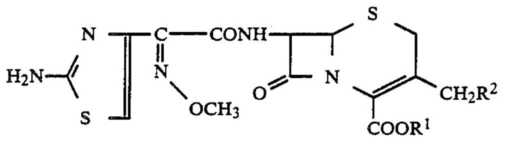

(syn-isomer)

| $R^1$ | $R^2$ |
|---|---|
| $-CH_2OCOC(CH_3)_3$ | 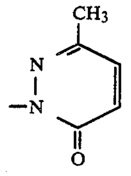 |
| $-CH_2OCOC(CH_3)_3$ | 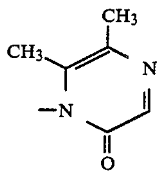 |
| $-CH_2OCOC(CH_3)_3$ | 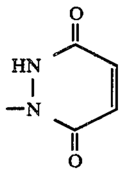 |
| $-CH_2OCOC(CH_3)_3$ | 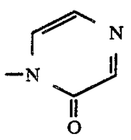 |
| $-\underset{\mid}{C}HOCOC(CH_3)_3$ $CH_3$ | 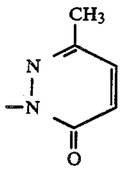 |
| $-CH_2OCOC(CH_3)_3$ | 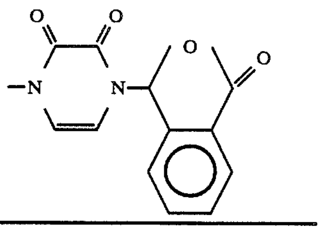 |

Note:
*Hydrochloride

Physical properties (m.p., IR and NMR spectra) of the above compounds were the same as those obtained in Examples 6, 7, 11 and 12.

EXAMPLE 10

(1) To a suspension of 2.2 g of 2-(2-formamidothiazol-4-yl)glyoxylic acid in 11 ml of N,N-dimethylacetamide was added dropwise 1.8 g of phosphorus oxychloride at −20° C., and the resulting mixture was subjected to reaction at the same temperature for 2 hours. Then, to this reaction mixture was added a solution of 26 ml of methylene chloride containing 5.2 of diphenylmethyl 7-amino-3-{[1-(4-ethyl-2,3-dioxo-1,2,3,4-tetrahydropyrazinyl)]methyl}-$\Delta^3$-cephem-4-carboxylate at $-30°$ to $-20°$ C. After completion of the dropwise addition, the mixture was subjected to reaction at same temperature for one hour. After completion of the reaction, 70 ml of water and 50 ml of methylene chloride were added to the reaction mixture. Then, sodium hydrogencarbonate was added thereto to adjust the mixture to pH 6.5, and the insolubles were removed by filtration. The organic layer was thereafter separated, washed with 100 ml of water and 10 ml of a saturated aqueous sodium chloride solution in this order, and dried over anhydrous magnesium sulfate. Subsequently, the solvent was removed by distillation under reduced pressure. The residue was purified by a column chromatography (Wako Silica Gel C-200, eluent; chloroform:methanol=20:1 by volume) to obtain 1.4 g (yield, 20.0%) of diphenylmethyl 7-[2-(2-formamidothiazol-4-yl)glyoxylamido]-3-{[1-(4-ethyl-2,3-dioxo-1,2,3,4-tetrahydropyrazinyl)]methyl}-$\Delta^3$-cephem-4-carboxylate having a melting point of 140°-145° C. (decomp.).

IR (KBr) $cm^{-1}$: $\nu_{C=O}$ 1780, 1720, 1680, 1670, 1640.

NMR ($d_6$-DMSO) $\delta$ values: 1.20 (3H, t, J=7 Hz, $>NCH_2C\underline{H_3}$), 3.50 (2H, bs, $C_2$—H), 3.69 (2H, q, J=7 Hz, $>NC\underline{H_2}CH_3$), 4.40, 5.00 (2H, ABq, J=15 Hz,

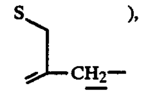), 5.30 (1H, d, J=5 Hz, $C_6$—H), 6.00 (1H, dd, J=5 Hz, J=9 Hz, $C_7$—H), 6.50, 6.62 (2H, ABq, J=5 Hz,

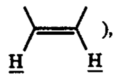), 7.04 (1H, s, —CH<), 7.30 (10H, bs,

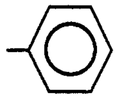 × 2), 8.64 (1H, s,

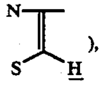), 8.81 (1H, s, $\underline{H}$CONH—), 10.20 (1H, d, J=9 Hz, —CONH—), 12.90 (1H, bs, HCON$\underline{H}$—).

In a similar manner, the following compound was obtained: 0.09 g (yield, 19.2%) of diphenylmethyl 7-[2-(2-formamidothiazol-4-yl)glyoxylamido]-3-{[1-(3,6-dioxo-1,2,3,6-tetrahydropyridazinyl)]methyl}-$\Delta^3$-cephem-4-carboxylate, m.p.: 153°-154° C. (decomp.).

IR (KBr) $cm^{-1}$: $\nu_{C=O}$ 1780, 1725, 1690, 1665.

NMR ($CDCl_3+d_6$-DMSO) $\delta$ values: 3.42 (2H, bs, $C_2$—H), 4.96-5.40 (3H, m,

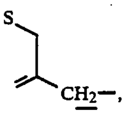, $C_6$—H), 5.95 (1H, dd, J=5 Hz, J=8 Hz, $C_7$—H), 6.72-7.78 (13H, m,

, 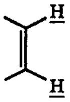, 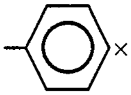 × 2), 8.66 (1H, s,

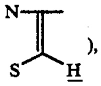), 8.73 (1H, s, HCO—), 9.86 (1H, d, J=8 Hz, —CONH—)

(2) To a solution of 7.0 g of diphenylmethyl 7-[2-(2-formamidothiazol-4-yl)glyoxylamido]-3-{[1-(4-ethyl-2,3-dioxo-1,2,3,4-tetrahydropyrazinyl)]methyl}-$\Delta^3$-cephem-4-carboxylate in 35 ml of N,N-dimethylacetamide was added 1.7 g of methoxyamine hydrochloride with ice-cooling, and the resulting mixture was subjected to reaction at 15°-20° C. for 3 hours. After completion of the reaction, the reaction mixture was poured into a mixed solvent of 250 ml of water and 250 ml of ethyl acetate, and the organic layer was separated, washed with 250 ml of water and 250 ml of a saturated aqueous sodium chloride solution in this order, and dried over anhydrous magnesium sulfate. Then, the solvent was removed by distillation under reduced pressure. To the residue was added 50 ml of diethyl ether, and the resulting crystals were collected by filtration to obtain 6.1 g (yield, 83.7%) of diphenylmethyl 7-[2-(2-formamidothiazol-4-yl)-2-(syn)-methoxyiminoacetamido]-3-{[1-(4-ethyl-2,3-dioxo-1,2,3,4-tetrahydropyrazinyl]methyl}-$\Delta^3$-cephem-4-carboxylate having a melting point of 165°-168° C.

IR (KBr) $cm^{-1}$: $\nu_{C=O}$ 1780, 1720, 1680, 1640.

In a similar manner, the following compound was obtained:

Diphenylmethyl 7-[2-(2-formamidothiazol-4-yl)-2-(syn)-methoxyiminoacetamido]-3-{[1-(3,6-dioxo-1,2,3,6-tetrahydropyridazinyl)]methyl}-$\Delta^3$-cephem-4-carboxylate, m.p. 171°-173° C. (decomp.).

The same oximination reaction as above was conducted, and then, the reaction mentioned in Example 6-(2), (3) and/or Example 7-(2) was conducted, to obtain the following compound and the compounds shown in Tables 27, 28 and 29:

Trifluoroacetic acid salt of 7-[2-(2-amino-5-bromothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylic acid, m.p.: 147° C. (decomp.).
IR (KBr) $cm^{-1}$: $\nu_{C=O}$ 1775, 1680, 1640.
TABLE 27
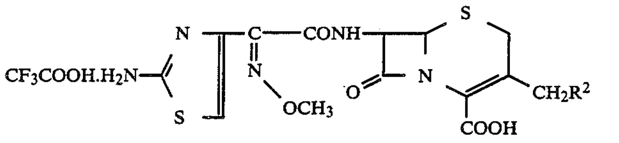
(syn-isomer)
| $R^2$ | $R^2$ | $R^2$ |
|---|---|---|
| 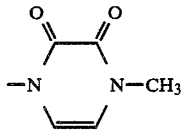 | 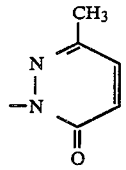 | 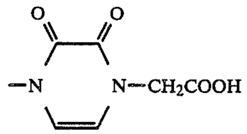 |
| 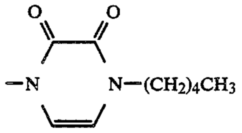 | 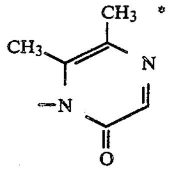 * | 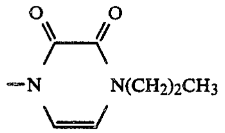 |
| 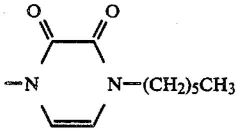 | 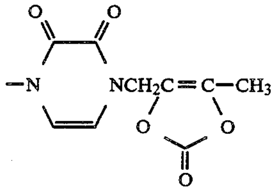 | 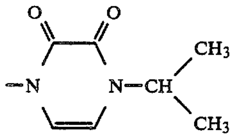 |
| 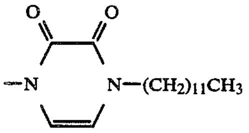 | 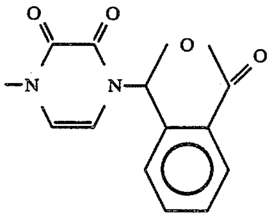 | 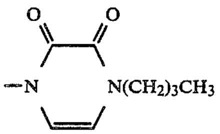 |
| 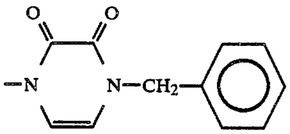 | 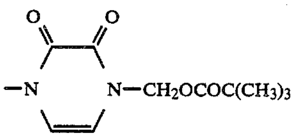 | 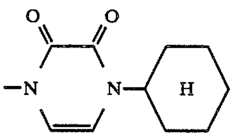 |
| $R^2$ | $R^2$ |
|---|---|
| 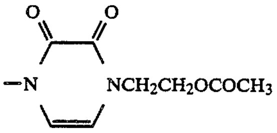 | 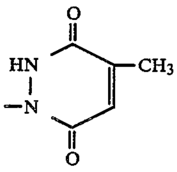 + 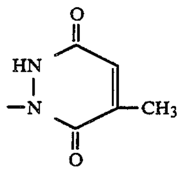 |
| 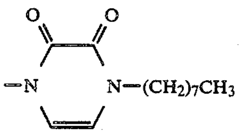 | 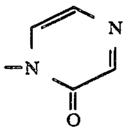 |

TABLE 27-continued
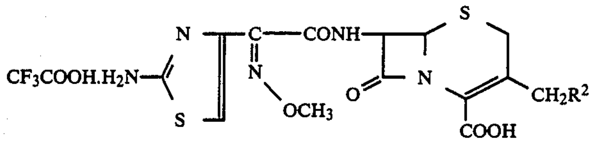
(syn-isomer)
| | |
|---|---|
| 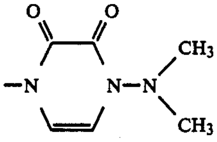 | 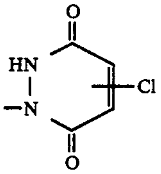 |
| 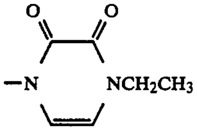 | 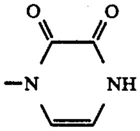 |
| 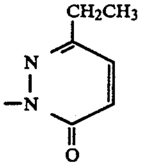 | 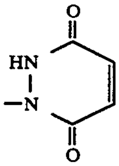 |
Note:
*Hydrochloride
TABLE 28
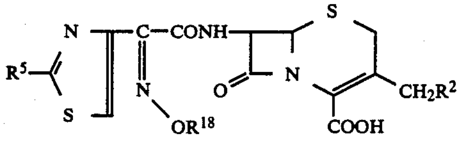
(syn-isomer)
| $R^2$ | $R^5$ | $R^{18}$ |
|---|---|---|
| 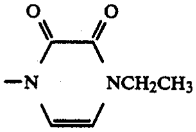 | $NH_2-$ | $-CH_2COOH$ |
| 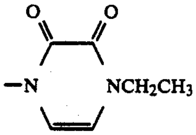 | $CF_3COOH.NH_2-$ | 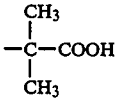 |
| 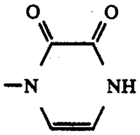 | $NH_2-$ | $-CH_2COOH$ |
| 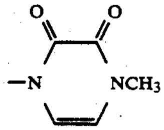 | $CF_3COOH.NH_2-$ | $-CH_2COOH$ |

TABLE 28-continued
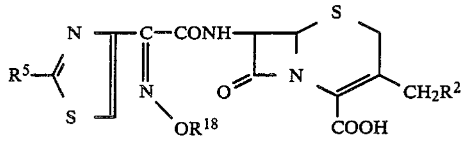
(syn-isomer)
| $R^2$ | $R^5$ | $R^{18}$ |
|---|---|---|
| 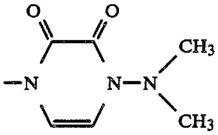 | $CF_3COOH.NH_2$— | —$CH_2COOH$ |
| 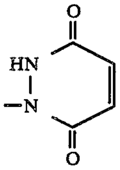 | $HCOOH.NH_2$— | —$CH_2COOH$ |
| 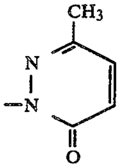 | $HCOOH.NH_2$— | —$CH_2COOH$ |
| 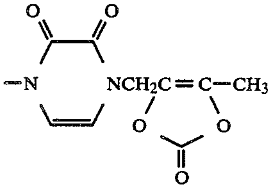 | $NH_2$— | —$CH_2COOH$ |
| 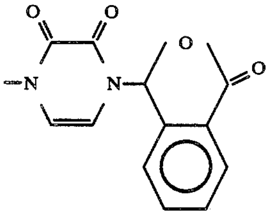 | $NH_2$— | —$CH_2COOH$ |
| 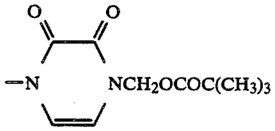 | $NH_2$— | —$CH_2COOH$ |
| 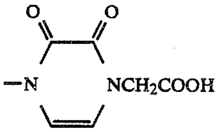 | $NH_2$— | —$CH_2COOH$ |
| 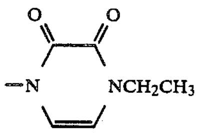 | $HCOOH.NH_2$— | 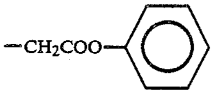 |

TABLE 28-continued
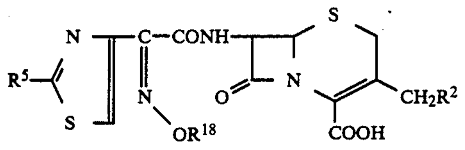
(syn-isomer)
| $R^2$ | $R^5$ | $R^{18}$ |
|---|---|---|
| 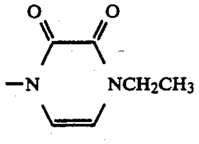 | HCOOH.$NH_2$— | 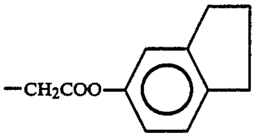 |
| 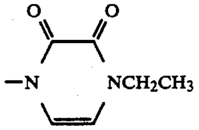 | HCOOH.$NH_2$— | —$CH_2COOCH_2CH_3$ |
TABLE 29
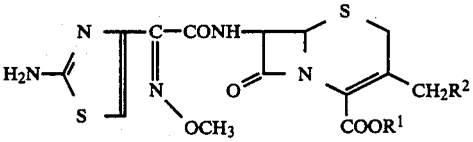
(syn-isomer)
| $R^1$ | $R^2$ |
|---|---|
| —CHOCOC($CH_3$)$_3$ with CH$_3$ | 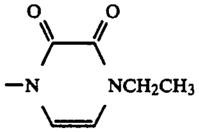 |
| —CHOCOC($CH_3$)$_3$ with CH$_3$ | 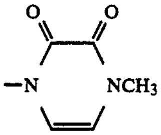 |
| —CHOCOC($CH_3$)$_3$ with CH$_3$ | 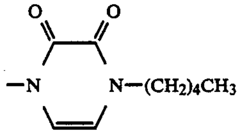 |
| —CHOCOC($CH_3$)$_3$ with CH$_3$ | 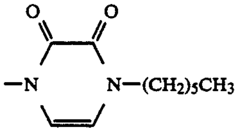 |
| —CHOCOC($CH_3$)$_3$ with CH$_3$ | 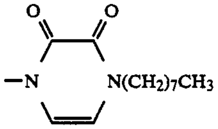 |
TABLE 29-continued
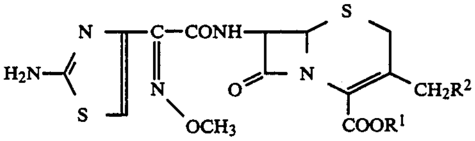
(syn-isomer)
| $R^1$ | $R^2$ |
|---|---|
| —CHOCOC($CH_3$)$_3$ with CH$_3$ | 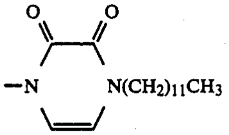 |
| —$CH_2OCOC(CH_3)_3$ | 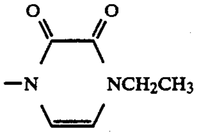 |
| —CHOCOOC($CH_3$)$_3$ with CH$_3$ | 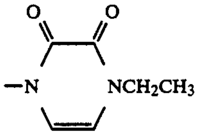 |
| 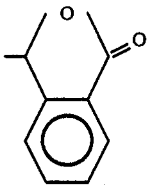 | 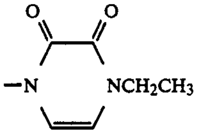 |
| —$(CH_2)_3CH_3$ | 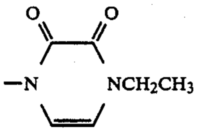 |

TABLE 29-continued

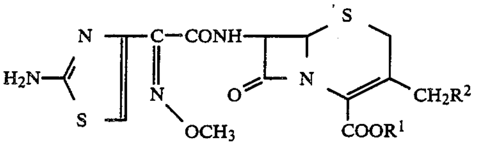

(syn-isomer)

| $R^1$ | $R^2$ |
|---|---|
| 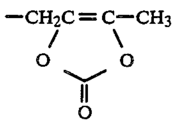 | 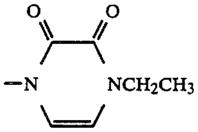 |
| $-CH_2OCOC(CH_3)_3$ | 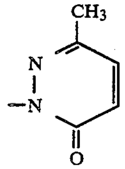 |
| $-CH_2OCOC(CH_3)_3$ | 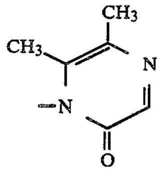 |
| $-CH_2OCOC(CH_3)_3$ | 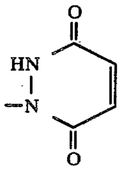 |
| $-CH_2OCOC(CH_3)_3$ | 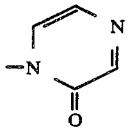 |
| 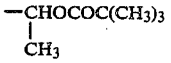 | 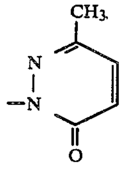 |
| $-CH_2OCOC(CH_3)_3$ | 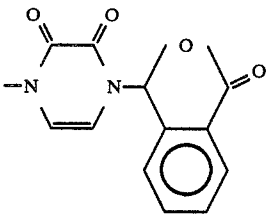 |

Physical properties (m.p., IR and NMR spectra) of the above compounds were the same as those obtained in Examples 6, 7, 11 and 12.

EXAMPLE 11

(1) In a mixed solvent of 37 ml of trifluoroacetic acid and 10.8 g of anisole was dissolved 7.29 g of diphenylmethyl 7-[2-(2-formamidothiazol-4-yl)-2-(syn)methoxyiminoacetamido]-3-{[1-(4-ethyl-2,3-dioxo-1,2,3,4-tetrahydropyrazinyl)methyl}-$\Delta^3$-cephem-4-carboxylate, and the resulting solution was subjected to reaction at room temperature for 2 hours. After completion of the reaction, the solvent was removed by distillation under reduced pressure. To the resulting residue was added 50 ml of diethyl ether, and the crystals were collected by filtration, washed sufficiently with 50 ml of diethyl ether and dried to obtain 5.2 g (yield, 92.4%) of 7-[2-(2-formamidothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylic acid having a melting point of 155°-158° C. (decomp.).

IR (KBr) $cm^{-1}$: $\nu_{C=O}$ 1775, 1710, 1675, 1640.

NMR ($d_6$-DMSO) $\delta$ values: 1.20 (3H, t, J=7 Hz, $>NCH_2C\underline{H_3}$), 3.49 (2H, bs, $C_2$—H), 3.73 (2H, q, J=7 Hz, $>NC\underline{H_2}CH_3$), 3.91 (3H, s, $-OCH_3$), 4.42, 4.95 (2H, ABq, J=15 Hz,

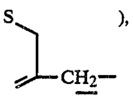

), 5.21 (1H, d, J=5 Hz, $C_6$—H), 5.89 (1H, dd, J=5 Hz, J=8 Hz, $C_7$—H), 6.65 (2H, bs,

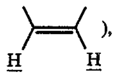

), 7.46 (1H, s,

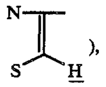

), 8.59 (1H, s, $\underline{H}CONH-$), 9.77 (1H, d, J=8 Hz, —CONH—), 12.58 (1H, bs, $HCON\underline{H}-$).

In a similar manner, the compounds shown in Table 30 were obtained.

TABLE 30

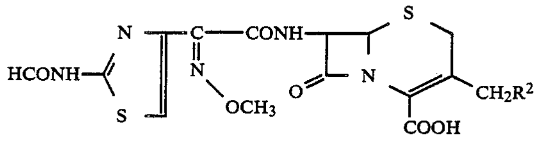

(syn-isomer)

| Compound $R^2$ | m.p. (°C.) | IR (KBr) $cm^{-1}$: $\nu_{C=O}$ |
|---|---|---|
| 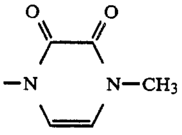 | 195-198 (decomp). | 1775, 1720, 1680-1640 |

TABLE 30-continued

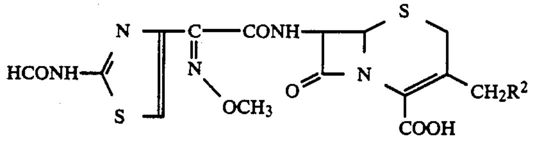

(syn-isomer)

| Compound $R^2$ | m.p. (°C.) | IR (KBr) $cm^{-1}$: $\nu_{C=O}$ |
|---|---|---|
| 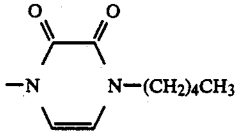 | 122-125 (decomp.) | 1775, 1680, 1640 |
| 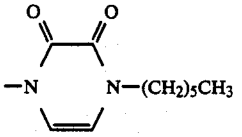 | 165-170 (decomp.) | 1775, 1680, 1640 |
| 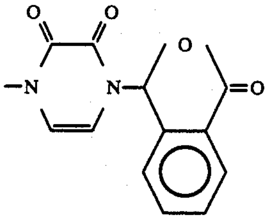 | 195-198 (decomp.) | 1775, 1685, 1650 |
| 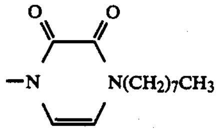 | 155-158 (decomp.) | 1780, 1720, 1680-1640 |
| 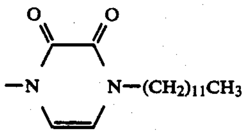 | 144-147 (decomp.) | 1778, 1685, 1660, 1645 |
| 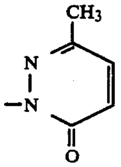 | 186-188 (decomp.) | 1775, 1710, 1690, 1650 |

TABLE 30-continued

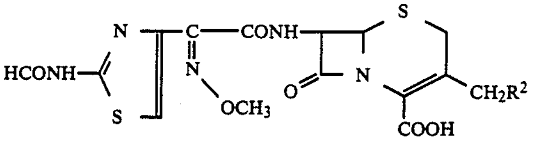

(syn-isomer)

| Compound $R^2$ | m.p. (°C.) | IR (KBr) $cm^{-1}$: $\nu_{C=O}$ |
|---|---|---|
| 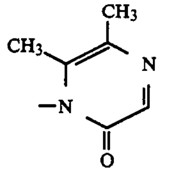 | 218-221 (decomp.) | 1775, 1670, 1650 |

(2) To a solution of 5.63 g of 7-[2-(2-formamidothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylic acid in 25 ml of N,N-dimethylacetamide were added 1.52 g of 1,8-diazabicyclo[5,4,0]-7-undecene and 3.84 g of 1-pivaloyloxyethyl iodide with ice-cooling, and the resulting mixture was subjected to reaction for 30 minutes. After completion of the reaction, the reaction mixture was poured into a mixed solvent of 100 ml of water and 100 ml of ethyl acetate. Subsequently, the organic layer was separated, washed with water, and then dried over anhydrous magnesium sulfate. The solvent was removed by distillation under reduced pressure. To the residue was added 50 ml of diethyl ether, and the crystals were collected by filtration to obtain 5.5 g (yield, 79.6%) of 1-pivaloyloxyethyl 7-[2-(2-formamidothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylate having a melting point of 140°-142° C.

IR (KBr) $cm^{-1}$: $\nu_{C=O}$ 1780, 1740, 1680, 1640.

In a similar manner, the compounds shown in Table 31 were obtained. In this case, the compounds shown in Table 31 can also be obtained by the same method as in Example 6-(1), except that the corresponding esters were substituted for the diphenylmethyl esters.

TABLE 31

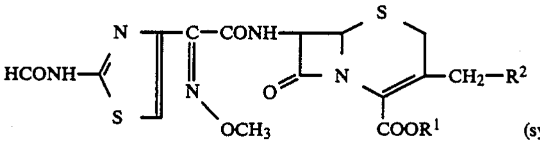

(syn-isomer)

| Compound $R^1$ | $R^2$ | m.p. (°C.) | IR (KBr) $cm^{-1}$: $\nu_{C=O}$ |
|---|---|---|---|
| $-CHOCOC(CH_3)_3$<br>\|<br>$CH_3$ | 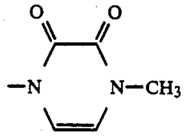 | 182-188 (decomp.) | 1780, 1740, 1680-1640 |

TABLE 31-continued
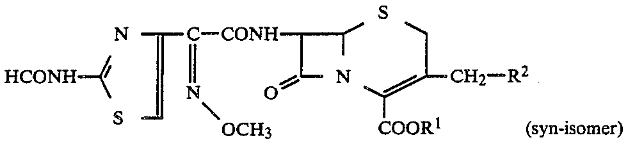
(syn-isomer)
| R[1] | R[2] | m.p. (°C.) | IR (KBr) $cm^{-1}$: $\nu_{C=O}$ |
|---|---|---|---|
| $-CHOCOC(CH_3)_3$<br>$CH_3$ | 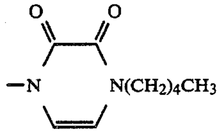 | 120–122 (decomp.) | 1783, 1740, 1680, 1640 |
| $-CHOCOC(CH_3)_3$<br>$CH_3$ | 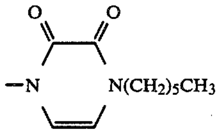 | 108–115 | 1782, 1740, 1680, 1640 |
| $-CHOCOC(CH_3)_3$<br>$CH_3$ | 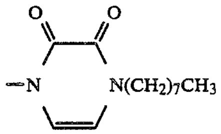 | 166–168 (decomp.) | 1780, 1740, 1680–1640 |
| $-CHOCOC(CH_3)_3$<br>$CH_3$ | 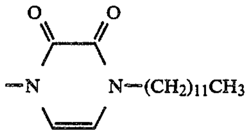 | 117–122 | 1785, 1745, 1685, 1645 |
| $-CH_2OCOC(CH_3)_3$ | 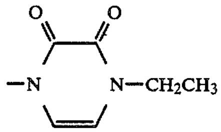 | 158–160 | 1780, 1742, 1680, 1640 |
| $-CHCOOCH_2CH_3$<br>$CH_3$ | 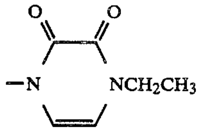 | 150–152 | 1780, 1760, 1680, 1640 |
| 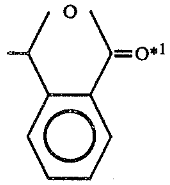 | 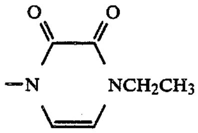 | 160–162 | 1780, 1680–1630 |
| $-(CH_2)_3CH_3$ | 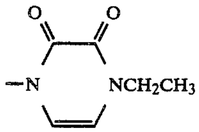 | 136–141 (decomp.) | 1780, 1720, 1680, 1640 |
| 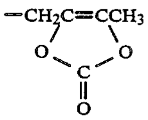 | 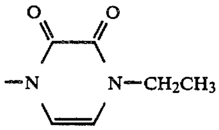 | 165–168 (decomp.) | 1810, 1775, 1720, 1670, 1640 |

TABLE 31-continued

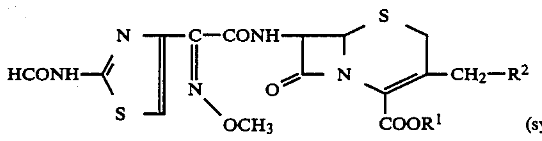

(syn-isomer)

| Compound | | | |
|---|---|---|---|
| $R^1$ | $R^2$ | m.p. (°C.) | IR (KBr) $cm^{-1}$: $\nu_{C=O}$ |
| $-CH_2OCOC(CH_3)_3$ | 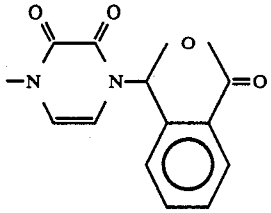 | 193-195 (decomp.) | 1775, 1745, 1685, 1650 |
| $-CH_2OCOC(CH_3)_3$ | 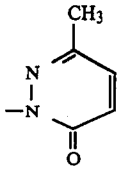 | 138-140 (decomp.) | 1780, 1750, 1690, 1660 |
| $-CH_2OCOC(CH_3)_3$ | 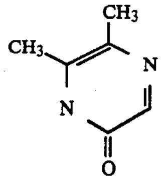 | 158-164 (decomp.) | 1780, 1740, 1680-1640 |

Note:
*[1]Diastereomer (3) To a solution of the 5.5 g of 1-pivaloyloxyethyl 7-[2-(2-formamidothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylate obtained in above (2) in 27.5 ml of methanol was added 1.13 ml of concentrated hydrochloric acid, and the resulting mixture was subjected to reaction at 35° C. for 2 hours. After completion of the reaction, the solvent was removed by distillation under reduced pressure. To the residue were added 50 ml of ethyl acetate and 50 ml of water, and the mixture was adjusted to pH 6.0 with sodium hydrogencarbonate. Subsequently, the organic layer was separated and dried over anhydrous magnesium sulfate, after which the solvent was removed by distillation under reduced pressure. To the residue was added 45 ml of diethyl ether, and the crystals were collected by filtration to obtain 4.65 g (yield, 88.1%) of 1-pivaloyloxyethyl 7-[2-(2-aminothiazol-4-yl)-2-(syn)-methoxyiminoacetamido]-3-{[1-(4-ethyl-2,3-dioxo-1,2,3,4-tetrahydropyrazinyl)]methyl}-$\Delta^3$-cephem-4-carboxylate having a melting point of 148°-150° C.

IR (KBr) $cm^{-1}$: $\nu_{C=O}$ 1780, 1740, 1680, 1640.

NMR ($d_6$-DMSO) δ values: 0.90-1.39 (12H, m, $-C(CH_3)_3$, $>NCH_2CH_3$), 1.52 (3H, d, J=5 Hz,

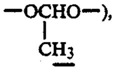

3.52 (2H, bs, $C_2$—H), 3.76 (2H, q, J=7 Hz, $>NCH_2CH_3$), 3.88 (3H, s, $-OCH_3$), 4.38, 5.04 (2H, ABq, J=15 Hz,

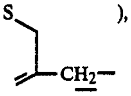

5.21 (1H, d, J=5 Hz, $C_6$—H), 5.87 (1H, dd, J=5 Hz, J=8 Hz, $C_7$—H), 6.61 (2H, bs,

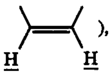

6.78 (1H, s,

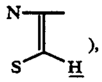

7.04 (1H, q, J=5 Hz,

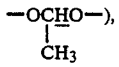

7.22 (2H, bs, —$NH_2$), 9.67 (1H, d, J=8 Hz, —CONH—).

In a similar manner, the compounds shown in Table 32 were obtained.

TABLE 32

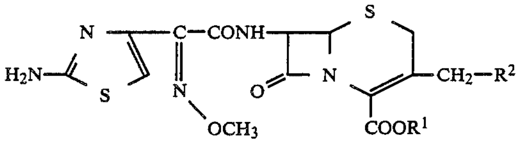
(syn-isomer)

| Compound R¹ | Compound R² | m.p. (°C.) | IR (KBr) $cm^{-1}$: $\nu_{C=O}$ | NMR ($d_6$-DMSO) δ values: |
|---|---|---|---|---|
| —CHOCOC($CH_3$)$_3$ \| $CH_3$ | 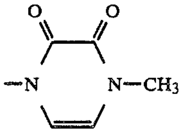 | 198-201 (decomp.) | 1780, 1740, 1680~1640 | 1.19 (9H, s, —C($CH_3$)$_3$), 1.54 (3H, d, J=5Hz, —OCHO—, \| <u>CH₃</u>), 3.30 (3H, s, N—$CH_3$), 3.54 (2H, bs, $C_2$—H), 3.88 (3H, s, —$OCH_3$), 4.40, 5.06 (2H, ABq, J=15Hz, 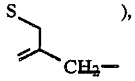), 5.24 (1H, d, 5Hz, $C_6$—H), 5.91 (1H, dd, J=5Hz, J=8Hz, $C_7$—H), 6.46, 6.60 (2H, ABq, J=6Hz, 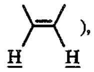), 6.80 (1H, s, 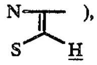), 7.07 (1H, q, J=5Hz, —C<u>H</u>—, \| $CH_3$), 7.26 (2H, bs, —$NH_2$), 9.74 (1H, d, J=8Hz, —CONH—) |
| —CHOCOC($CH_3$)$_3$ \| $CH_3$ | 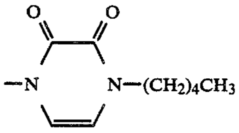 | 139-141 (decomp.) | 1783, 1740, 1680, 1640 | 0.87 (3H, t, J=7Hz, N($CH_2$)$_4$<u>CH₃</u>), 1.18 (9H, s, —C($CH_3$)$_3$), 1.53 (3H, d, J=5Hz, —CHO—, \| <u>CH₃</u>), 1.04-1.85 (6H, m, NCH$_2$<u>(CH₂)₃</u>CH$_3$), 3.59 (2H, bs, $C_2$—H), 3.72 (2H, t, J=7Hz, N<u>CH₂</u>(CH$_2$)$_3$CH$_3$), 3.91 (3H, s, —$OCH_3$), 4.45, 5.08 (2H, ABq, J=15Hz, 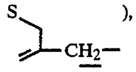), 5.28 (1H, d, J=5Hz, $C_6$—H), 5.92 (1H, dd, J=5Hz, J=8Hz, $C_7$—H), 6.65 (2H, bs, 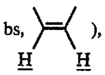), 6.85 (1H, s, 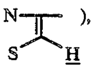), 7.00 (1H, q, J=5Hz, —OC<u>H</u>O—, \| $CH_3$), 9.82 (1H, d, J=8Hz, —CONH— |

TABLE 32-continued

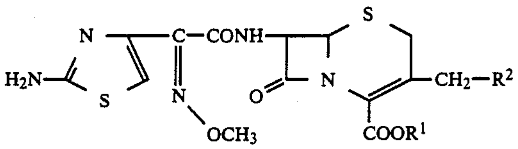

(syn-isomer)

| Compound | | | | |
|---|---|---|---|---|
| $R^1$ | $R^2$ | m.p. (°C.) | IR (KBr) $cm^{-1}$: $\nu_{C=O}$ | NMR ($d_6$-DMSO) δ values: |
| $-CHOCOC(CH_3)_3$ <br> $CH_3$ | 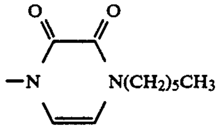 | 145-150 (decomp.) | 1780, 1740, 1685, 1645 | 0.87 (3H, t, J=7Hz, $N(CH_2)_5CH_3$), 1.18 (9H, s, $-C(CH_3)_3$), 1.03-1.79 (8H, m, $NCH_2(CH_2)_4CH_3$), 1.53 (3H, d, J=5Hz, $-OCHO-$ $CH_3$), 3.60 (2H, bs, $C_2-H$), 3.72 (2H, t, J=7Hz, $NCH_2(CH_2)_4CH_3$), 3.90 (3H, s, $-OCH_3$), 4.41, 5.09 (2H, ABq, J=15Hz, 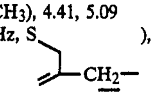), 5.25 (1H, d, J=5Hz, $C_6-H$), 5.90 (1H, dd, J=5Hz, J=8Hz, $C_7-H$), 6.63 (2H, bs, 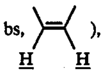), 6.82 (1H, s, 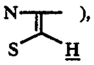), 6.98 (1H, q, J=5Hz, $-OCHO-$ $CH_3$), 9.75 (1H, d, J=8Hz, $-CONH-$) |
| $-CHOCOC(CH_3)_3$ <br> $CH_3$ | 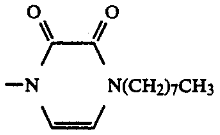 | 170-172 (decomp.) | 1780, 1740, 1680, 1640 | 0.88 (3H, t, J=8Hz, $N(CH_2)_7CH_3$), 1.02-1.43 (21H, m, $-C(CH_3)_3$, $NCH_2(CH_2)_6CH_3$), 1.56 (3H, d, J=5Hz, $-OCHO-$ $CH_3$), 3.38-3.83 (4H, m, $NCH_2(CH_2)_6CH_3$, $C_2-H$), 3.90 (3H, s, $-OCH_3$), 4.43, 5.11 (2H, ABq, J=15Hz, 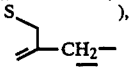), 5.28 (1H, d, J=5Hz, $C_6-H$), 5.94 (1H, dd, J=5Hz, J=8Hz, $C_7-H$), 6.65 (2H, bs, 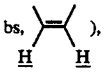), 6.83 (1H, s, 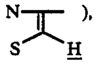), 7.02 (1H, q, J=5Hz, $-OCHO-$ $CH_3$), 7.15 (2H, bs, $-NH_2$), |

TABLE 32-continued

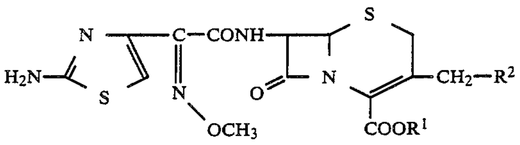

(syn-isomer)

| Compound R¹ | R² | m.p. (°C.) | IR (KBr) $cm^{-1}$: $\nu_{C=O}$ | NMR ($d_6$-DMSO) δ values: |
|---|---|---|---|---|
| | | | | 9.70 (1H, d, J=8Hz, —CONH—) |
| $-CHOCOC(CH_3)_3$<br>$CH_3$ | 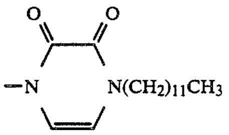 | 153–158<br>(decomp.) | 1780,<br>1745,<br>1675,<br>1640 | 0.86 (3H, t, J=7Hz, 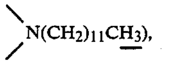), 1.18 (9H, s, $-C(CH_3)_3$), 1.02–1.87 (20H, m, 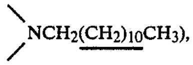), 1.52 (3H, d, J=5Hz, 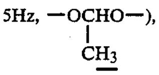), 3.53 (2H, bs, $C_2$—H), 3.70 (2H, t, J=7Hz, 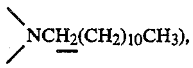), 3.87 (3H, s, $-OCH_3$), 4.38, 5.03 (2H, ABq, J=15Hz, 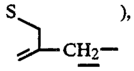), 5.20 (1H, d, J=5Hz, $C_6$—H), 5.85 (1H, dd, J=5Hz, J=8Hz, $C_7$—H), 6.58 (2H, bs, 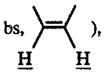), 6.75 (1H, s, 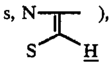), 7.01 (1H, q, J=5Hz, 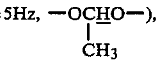), 9.65 (1H, d, J=8Hz, —CONH—) |
| $-CH_2OCOC(CH_3)_3$ | 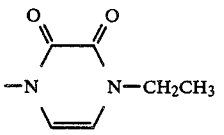 | 145–147 | 1780,<br>1740,<br>1675,<br>1640 | 1.01–1.35 (12H, m, $-C(CH_3)_3$, 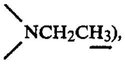), 3.47 (2H, bs, $C_2$—H), 3.70 (2H, q, J=7Hz, 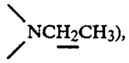), 3.78 (3H, s, $-OCH_3$), 4.30, 5.01 (2H, ABq, J=15Hz, 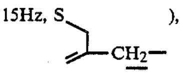), 5.14 (1H, d, J=5Hz, $C_6$—H), 5.67–6.06 (3H, m, $-OCH_2O-$, $C_7$—H), 6.55 (2H, bs, 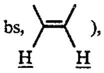), 6.70 (1H, s, 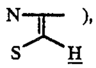), 7.12 (2H, bs, $-NH_2$), 9.52 (1H, d, J=8Hz, —CONH—) |

TABLE 32-continued

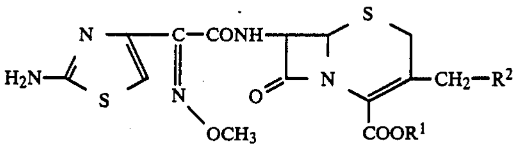

(syn-isomer)

| Compound | | | IR (KBr) $cm^{-1}$: | |
|---|---|---|---|---|
| $R^1$ | $R^2$ | m.p. (°C.) | $\nu_{C=O}$ | NMR ($d_6$-DMSO) δ values: |
| $-CHOCOOCH_2CH_3$<br>$CH_3$ | 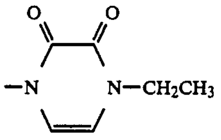 | 155-157 | 1780,<br>1760,<br>1680,<br>1640 | 1.23 (6H, t, J=7Hz, $>NCH_2CH_3$,<br>$-OCH_2CH_3$), 1.55 (3H, d, H=5Hz,<br>$-OCHO-$), 3.53 (2H, bs, $C_2-H$),<br>$CH_3$<br>3.76 (2H, q, J=7Hz, $>NCH_2CH_3$),<br>3.86 (3H, s, $-OCH_3$), 4.19 (2H,<br>q, J=7Hz, $-OCH_2CH_3$), 4.40,<br>5.05 (2H, ABq, J=15Hz, 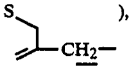 ),<br>5.21 (1H, d, J=5Hz, $C_6-H$), 5.86<br>(1H, dd, J=5Hz, J=8Hz, $C_7-H$),<br>6.52, 6.65 (2H, ABq, J=6Hz,<br>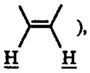 ), 6.74 (1H, s, 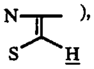 ),<br>6.87 (1H, q, J=5Hz, $-OCHO$),<br>$CH_3$<br>7.02 (2H, bs, $-NH_2$), 9.65 (1H,<br>d, J=8Hz, $-CONH-$) |
| *1<br>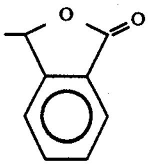 | *2<br>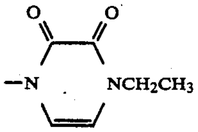 | >200 | 1780,<br>1680,<br>1640 | 1.21 (3H, t, J=7Hz, $>NCH_2CH_3$),<br>3.67 (2H, bs, $C_2-H$), 3.81 (2H,<br>t, J=7Hz, $>NCH_2CH_3$), 3.99 (3H, s,<br>$-OCH_3$), 4.17-5.13 (5H, m, 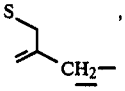 ,<br>$-NH_3^{\oplus}$), 5.22 (1H, d, J=5Hz, $C_6-H$),<br>5.83 (1H, dd, J=5Hz, J=8Hz,<br>$C_7-H$), 6.95, 6.77 (2H, ABq,<br>J=7Hz, 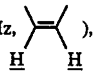 ), 6.95 (0.5H, s,<br>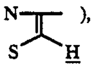 ), 7.00 (0.5H, s, 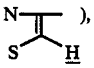 ),<br>7.58-8.15 (5H, m, 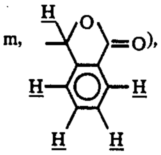 ),<br>9.87 (1H, d, J=8Hz, $-CONH-$) |

TABLE 32-continued

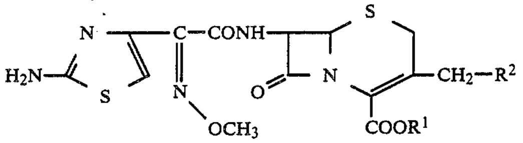

(syn-isomer)

| Compound R¹ | R² | m.p. (°C.) | IR (KBr) $cm^{-1}$: $\nu_{C=O}$ | NMR ($d_6$-DMSO) δ values: |
|---|---|---|---|---|
| $-(CH_2)_3CH_3$ | 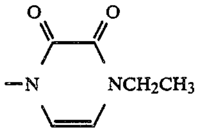 | 139-144 (decomp.) | 1780, 1720, 1680, 1640 | 0.63-1.85 (10H, m, $-COOCH_2CH_2CH_2CH_3$, $NCH_2CH_3$), 3.55 (2H, bs, $C_2-H$), 3.76 (2H, q, J=7Hz, $NCH_2CH_3$), 3.89 (3H, s, $-OCH_3$), 4.30 (2H, t, J=7Hz, $-COOCH_2CH_2CH_2CH_3$), 4.39, 5.12 (2H, ABq, J=15Hz, S $CH_2-$ ), 5.25 (1H, d, J=5Hz, $C_6-H$), 5.92 (1H, dd, J=5Hz, J=8Hz, $C_7-H$), 6.68 (2H, bs, H H ), 6.82 (1H, s, N S H ), 7.28 (2H, bs, $-NH_2$), 9.79 (1H, d, J=8Hz, $-CONH-$) |
| 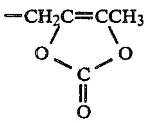 | 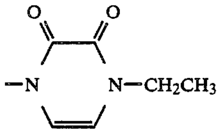 | 173-175 (decomp.) | 1820, 1780, 1730, 1680, 1640 | 1.19 (3H, t, J=7Hz, $NCH_2CH_3$), 2.20 (3H, s, $-C=C-CH_3$), 3.53 (2H, bs, $C_2-H$), 3.73 (2H, q, J=7Hz, $NCH_2CH_3$), 3.84 (3H, s, $-OCH_3$), 4.34, 5.06 (2H, ABq, J=15Hz, S $CH_2-$ ), 5.09-5.30 (3H, m, $C_6-H$, $-OCH_2C=$), 5.87 (1H, dd, J=5Hz, J=8Hz, $C_7-H$), 6.59 (2H, bs, H H ), 6.74 (1H, s, N S H ), 7.17 (2H, bs, $-NH_2$), 9.62 (1H, d, J=8Hz, $-CONH-$) |
| $-CH_2OCOC(CH_3)_3$ | 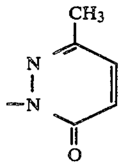 | 141-142 (decomp.) | 1775, 1740, 1650 | 1.24 (9H, s, $-C(CH_3)_3$), 2.31 (3H, s, $-CH_3$), 3.40 (2H, bs, $C_2-H$), 3.99 (3H, s, $-OCH_3$), 5.01, 5.33 (2H, ABq, J=15Hz, S $CH_2-$ ), 5.09 (1H, d, J=5Hz, $C_6-H$), 5.61-6.14 (3H, m, $-OCH_2O-$, $C_7-H$), 6.71 (2H, bs, $-NH_2$), |

TABLE 32-continued

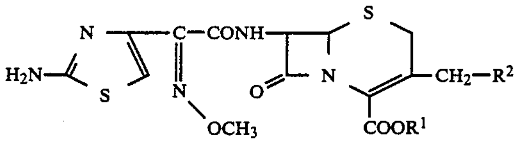

(syn-isomer)

| Compound | | | IR (KBr) $cm^{-1}$: | |
|---|---|---|---|---|
| $R^1$ | $R^2$ | m.p. (°C.) | $\nu_{C=O}$ | NMR ($d_6$-DMSO) δ values: |
| | | | | 6.77 (1H, s, 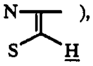), 6.86, 7.24 (2H, ABq, J=10Hz, 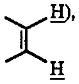), 9.34 (1H, d, J=8Hz, $-CONH-$) |
| $-CH_2OCOC(CH_3)_3$ | 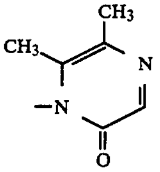 | 156-159 (decomp.) | 1775, 1740, 1670~1640 | 1.19 (9H, s, $-C(CH_3)_3$), 2.27 (6H, s, 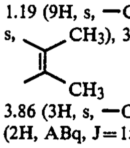), 3.35 (2H, bs, $C_2-H$), 3.86 (3H, s, $-OCH_3$), 5.02, 5.40 (2H, ABq, J=15Hz, 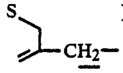), 5.20 (1H, d, J=5Hz, $C_6-H$), 5.70-6.14 (3H, m, $C_7-H$, $-OCH_2O-$), 6.81 (1H, s, 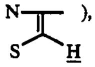), 7.26 (2H, m, $-NH_2$), 7.98 (1H, s, 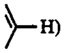) |
| *3 $-CH_2OCOC(CH_3)_3$ | 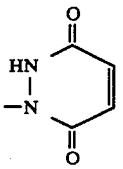 | 151-153 (decomp.) | 1780, 1745, 1660 | 1.17 (9H, s, $-C(CH_3)_3$), 3.43 (4H, bs, $C_2-H$, $-NH_2$), 3.85 (3H, s, $-OCH_3$), 4.75, 5.01 (2H, ABq, J=15Hz, 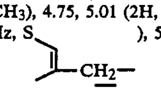), 5.16 (1H, d, J=5Hz, $C_6-H$), 5.60-6.08 (3H, m, $C_7-H$, $-OCH_2O-$), 6.77 (1H, s, 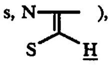), 6.89, 7.12 (2H, ABq, J=10Hz, 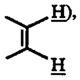), 9.62 (1H, d, J=8Hz, $-CONH-$) |
| *3 $-CH_2OCOC(CH_3)_3$ | 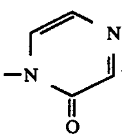 | 134-137 (decomp.) | 1780, 1750, 1680~1650 | 1.24 (9H, s, $-C(CH_3)_3$), 3.53 (2H, bs, $C_2-H$), 4.06 (3H, s, $-OCH_3$), 4.70, 5.35 (2H, ABq, J=15Hz, 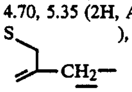), 5.25 (1H, d, J=5Hz, $C_6-H$), 5.98-6.48 (5H, m, $-OCH_2O-$, $C_7-H$, $-NH_2$), 6.88 (1H, s, 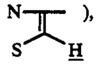), 7.54, 7.70 (2H, ABq, J=5Hz, 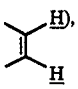), 8.33 (1H, s 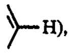), 8.59 (1H, d, J=8Hz, $-CONH-$) (measured in $CDCl_3$) |

TABLE 32-continued

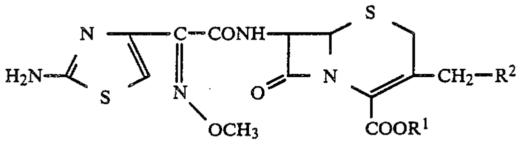

(syn-isomer)

| Compound R¹ | Compound R² | m.p. (°C.) | IR (KBr) $cm^{-1}$: $\nu_{C=O}$ | NMR ($d_6$-DMSO) δ values: |
|---|---|---|---|---|
| *3<br>$-CHOCO(CH_3)_3$<br>$CH_3$ | 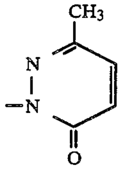 | 143-145 (decomp.) | 1780, 1740, 1655, | 1.18 (9H, s, $-C(CH_3)_3$), 1.53 (3H, d, J=6Hz, —OCHO—, $CH_3$), 2.28 (3H, s, 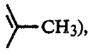$-CH_3$), 3.47 (4H, bs, $C_2$—H, $-NH_2$), 3.89 (3H, s, $-OCH_3$), 4.91, 5.29 (2H, ABq, J=15Hz, 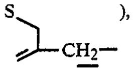), 5.22 (1H, d, J=5Hz, $C_6$—H), 5.88 (1H, dd, J=5Hz, J=8Hz, $C_7$—H), 6.92 (1H, s, 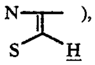), 6.93, 7.41 (2H, ABq, J=10Hz, 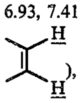), 6.96 (1H, q, J=6Hz, —OCHO—, $CH_3$) 9.74 (1H, d, J=8Hz, —CONH—) |
| $-CH_2OCOC(CH_3)_3$ | 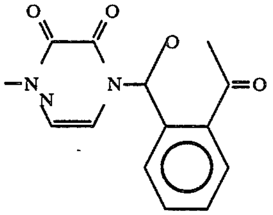 | 154-160 (decomp.) | 1775, 1750, 1700, 1650 | 1.21 (9H, s, $-C(CH_3)_3$, 3.65 (2H, bs, $C_2$—H), 3.93 (3H, s, $-OCH_3$), 4.44, 5.14 (2H, ABq, J=15Hz, 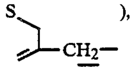), 5.28 (1H, d, J=5Hz, $C_6$—H), 5.78-6.76 (5H, m, $C_7$—H, $-OCH_2O-$, 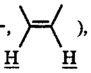), 6.89 (1H, s, 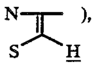), 7.36 (2H, bs, $NH_2$—), 7.72-8.27 (5H, m, 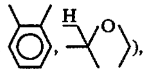), 9.81 (1H, d, J=8Hz, —CONH—) |

Note:
*1 Diastereomer
*2 Hydrochloride (The salt was prepared in a conventional manner.)
*3 The Objective compound was produced by reacting trifluoroacetic acid salt with a halide in the presence of 1,8-diazabicyclo[5,4,0]-7-undecene at −5-0° C.

(4) To a solution of 1.05 g of the 7-[2-(2-formamidothiazol-4-yl)-2-(syn)-methoxyiminoacetamido]-3-{[1-(2,3-dimethyl-6-oxo-1,6-dihydropyrazinyl)]methyl}-$\Delta^3$-cephem-4-carboxylic acid obtained in above (1) in 10 ml of methanol was added 0.38 ml of concentrated hydrochloric acid, and the resulting mixture was subjected to reaction at 35° C. for 2 hours. After completion of the reaction, the solvent was removed by distillation under reduced pressure. To the residue was added 10 ml of diethyl ether, and the crystals were collected by filtration to obtain 0.43 g (yield, 84.8%) of hydrochloride of 7-[2-(2-aminothiazol-4-yl)-2-(syn)-methoxyiminoacetamido]-3-{[1-(2,3-dimethyl-6-oxo-1,6-dihydropyrazinyl)]methyl}-$\Delta^3$-cephem-4-carboxylic acid having a melting point of 250° C. or more.

IR (KBr) $cm^{-1}$: $\nu_{C=O}$ 1765, 1660, 1620.

NMR ($d_6$-DMSO) δ values: 2.20 (6H, bs, $-CH_3\times 2$), 3.18 (2H, bs, $C_2$—H), 3.90 (3H, s, $-OCH_3$), 4.94, 5.24 (2H, ABq, J=15 Hz,

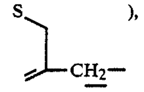), 5.10 (1H, d, J=5 Hz, $C_6$—H), 5.78 (1H, dd, J=5 Hz, J=8 Hz, $C_7$—H), 6.89 (1H, s,

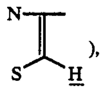

7.82 (1H, s,

9.79 (1H, dd, J=8 Hz, —CONH—).

EXAMPLE 12

(1) In a similar manner to that in Example 7-(1), the compounds shown in Table 33 were obtained from the starting materials shown below.

TABLE 33

| Objective Compound $R^1$ | m.p. (°C.) | IR (KBr) $cm^{-1}$: $\nu_{C=O}$ |
|---|---|---|
| 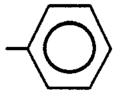 | 127–130 (decomp.) | 1780, 1720, 1685, 1645 |
| 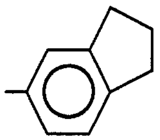 | 127–130 (decomp.) | 1780, 1720, 1685, 1635 |
| $-CH_2CH_3$ | 150–152 (decomp.) | 1780, 1720, 1680, 1645 |

(2) The compounds shown in Table 34 were obtained by reacting the above-mentioned compounds in a similar manner as in Example 7-(2).

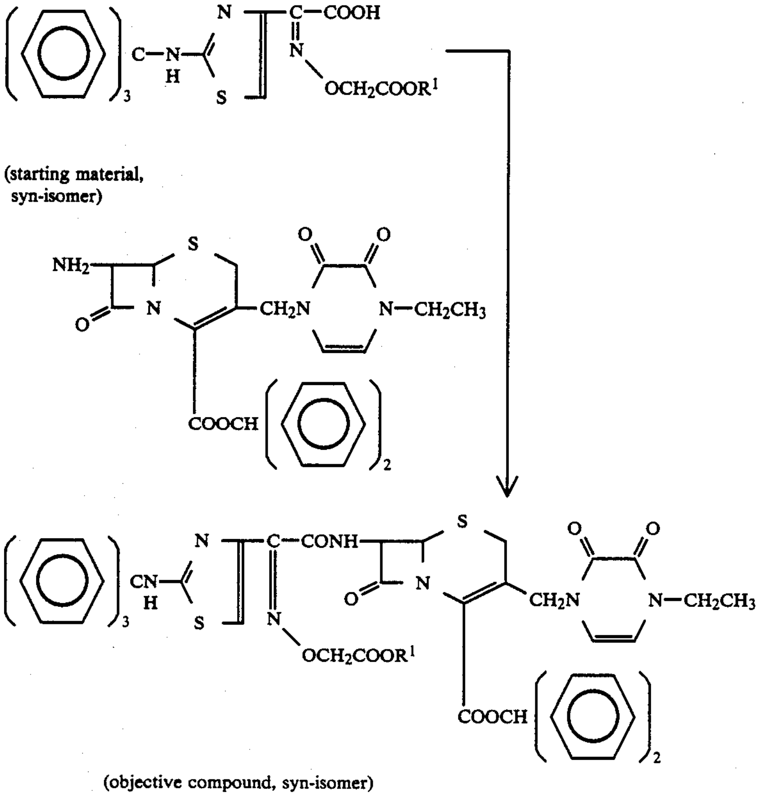

(objective compound, syn-isomer)

TABLE 34

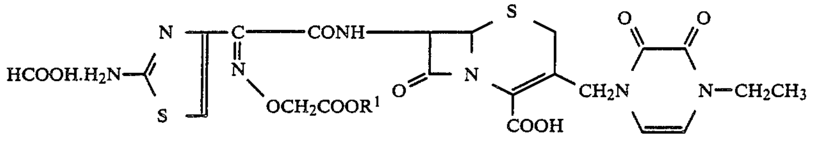

(syn-isomer)

| Compound $R^1$ | m.p. (°C.) | IR (KBr) $cm^{-1}$: $\nu_{C=O}$ | NMR ($d_6$-DMSO) δ values: |
|---|---|---|---|
| 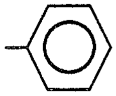 | 123-125 (decomp.) | 1770, 1680, 1670, 1630 | 1.25 (3H, t, J=7Hz, $NCH_2CH_3$), 3.50 (2H, bs, $C_2$—H), 3.76 (2H, q, J=7Hz, $NCH_2CH_3$), 5.03 (2H, s, —$OCH_2CO$—), 4.50-5.00 (2H, m, 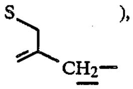 ), 5.20 (1H, d, J=5Hz, $C_6$—H), 5.90 (1H, dd, J=5Hz, J=9Hz, $C_7$—H), 6.70 (2H, s, 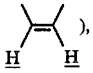 ), 6.98 (1H, s, 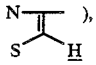 ), 7.30 (5H, bs, 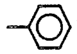 ), 8.27 (1H, s, HCOOH), 9.80 (1H, d, J=9Hz, —CONH—) |
| 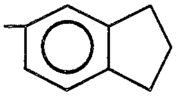 | 125-128 (decomp.) | 1770, 1680, 1670, 1635 | 1.25 (3H, t, J=7Hz, $NCH_2CH_3$), 2.00 (2H, m, 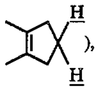 ), 2.80 (4H, m, 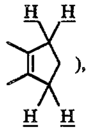 ), 3.50 (2H, bs, $C_2$—H), 3.75 (2H, q, J=7Hz, $NCH_2CH_3$), 5.00 (2H, s, —$OCH_2CO$—), 4.50-5.00 (2H, m, 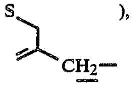 ), 5.25 (1H, d, J=5Hz, $C_6$—H), 5.95 (1H, dd, J=5Hz, J=9Hz, $C_7$—H), 6.70 (2H, s, 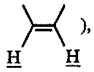 ), 6.96 (1H, s, 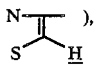 ), 7.30 (3H, m, 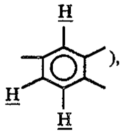 ), 8.27 (1H, s, HCOOH), 9.80 (1H, d, J=9Hz, —CONH—) |
| —$CH_2CH_3$ | 122-123 (decomp.) | 1770, 1720, 1670, 1640 | 1.22 (6H, t, J=7Hz, $NCH_2CH_3$, —$OCH_2CH_3$), 3.51 (2H, bs, $C_2$—H) 3.76 (2H, q, J=7Hz, $NCH_2CH_3$), 4.18 (2H, q, J=7Hz, —$OCH_2CH_3$), 4.77 (2H, s, —$OCH_2CO$—), 4.50-5.00 (2H, m, 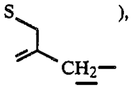 ), 5.24 (1H, d, J=5Hz, $C_6$—H), 5.91 (1H, dd, J=5Hz, |

TABLE 34-continued

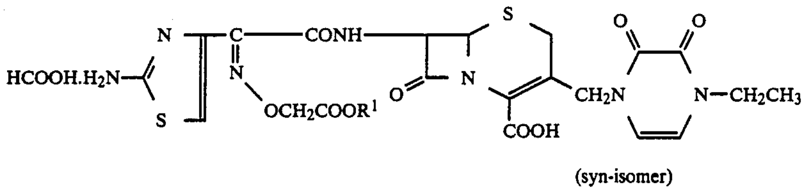

(syn-isomer)

| Compound R[1] | m.p. (°C.) | IR (KBr) $cm^{-1}$: $\nu_{C=O}$ | NMR ($d_6$-DMSO) δ values: |
|---|---|---|---|
| | | | J=9Hz, $C_7$—H), 6.69 (2H, s, 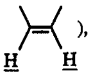 ), 6.96 (1H, s, 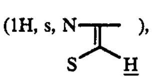 ), 8.27 (1H, s, HCOOH), 9.84 (1H, d, J=9Hz, —CONH—) |

EXAMPLE 13

(1) To a solution of 2.72 g of 2-(2-tert.-amyloxycarboxamidothiazol-4-yl)acetic acid in 40 ml of anhydrous methylene chloride was added 1.06 g of N-methylmorpholine, and the mixture was cooled to −35° C. Subsequently, 1.12 g of ethyl chlorocarbonate was added thereto, and the mixture was subjected to reaction at −35° to −25° C. for 1.5 hours, after which 5.18 g of diphenylmethyl 7-amino-3-{[1-(4-ethyl-2,3-dioxo-1,2,3,4-tetrahydropyrazinyl)]methyl}-$\Delta^3$-cephem-4-carboxylate was added thereto, and the mixture was subjected to reaction at −30° to −20° C. for 1 hour and then at −10° to 10° C. for 1 hour. After completion of the reaction, the solvent was removed by distillation under reduced pressure. The residue was dissolved in 40 ml of ethyl acetate and 30 ml of water. The organic layer was separated, and 30 ml of water was added again thereto. The mixture was adjusted to pH 7.0 with sodium hydrogencarbonate with ice-cooling. The organic layer was separated, washed with 30 ml of water and 30 ml of a saturated aqueous sodium chloride solution in this order, and dried over anhydrous magnesium sulfate. The solvent was removed by distillation under reduced pressure. To the residue was added 35 ml of diethyl ether, and the crystals were collected by filtration to obtain 3.62 g (yield, 90.5%) of diphenylmethyl 7-[2-(2-tert.-amyloxycarboxamidothiazol-4-yl)acetamido]-3-{[1-(4-ethyl-2,3-dioxo-1,2,3,4-tetrahydropyrazinyl]methyl}-$\Delta^3$-cephem-4-carboxylate having a melting point of 152°-154° C. (decomp.).

IR (KBr) $cm^{-1}$: $\nu_{C=O}$ 1780, 1720, 1685, 1640.

In a similar manner, the following compound was obtained: 6.15 g (yield, 82.7%) of diphenylmethyl 7-[2-(2-tert.-amyloxycarboxamidothiazol-4-yl)acetamido]-3-{[1-(3,6-dioxo-1,2,3,6-tetrahydropyridazinyl)]methyl}-$\Delta^3$-cephem-4-carboxylate, m.p.: 136°-139° C. (decomp.).

IR (KBr) $cm^{-1}$: $\nu_{C=O}$ 1780, 1720, 1665.

(2) The compounds shown in Table 35 were obtained by subjecting the compounds obtained in above (1) to reaction in the same manner as in Example 6-(3).

TABLE 35

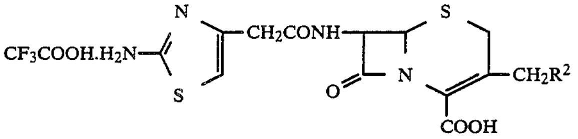

| Compound $R^2$ | m.p. (°C.) | IR (KBr) $cm^{-1}$: $\nu_{C=O}$ | NMR ($d_6$-DMSO) δ values |
|---|---|---|---|
| 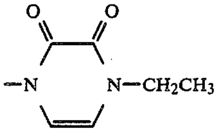 | 109-115 (decomp.) | 1775, 1690, 1630 | 1.20 (3H, t, J=7Hz, 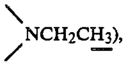), 3.50 (2H, bs, $C_2$—H), 3.61-3.81 (4H, m, 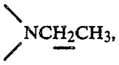, 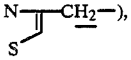), 4.47, 5.17 (2H, ABq, J=15Hz, 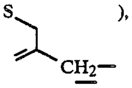), 5.21 (1H, d, J=5Hz, $C_6$—H), 5.60-6.02 (3H, m, $C_7$—H), 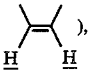), 6.81 (1H, s, 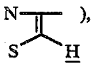), 9.24 (1H, d, J=8Hz, —CONH—) |
| 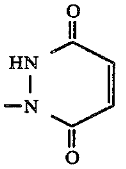 | >200 | 1770, 1710, 1670, 1630 | 3.43 (2H, bs, $C_2$—H), 3.67 (2H, bs, 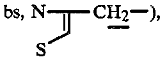), 5.08 (2H, bs, 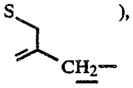), 5.16 (1H, d, J=5Hz, $C_6$—H), 5.78 (1H, dd, J=5Hz, J=8Hz, $C_7$—H), 6.76 (1H, s, 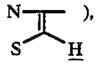), 7.01, 7.14 (2H, ABq, J=10Hz, 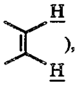), 9.29 (1H, d, J=8Hz, —CONH—) |

EXAMPLE 14

In 48 ml of N,N-dimethylacetamide were dissolved 6.82 g of diphenylmethyl 7-(4-bromo-3-oxobutyramido)-3-{[1-(4-ethyl-2,3-dioxo-1,2,3,4-tetrahydropyrazinyl)]methyl}-$\Delta^3$-cephem-4-carboxylate and 1 g of thiourea, and the mixture was subjected to reaction at room temperature for 2 hours. After completion of the reaction, the reaction mixture was poured into a mixed solvent of 500 ml of water and 500 ml of ethyl acetate, and the mixture was adjusted to pH 6.7 with sodium hydrogencarbonate. The organic layer was separated and dried over anhydrous magnesium sulfate, and then the solvent was removed by distillation under reduced pressure. Subsequently, the residue was dissolved in 33 ml of trifluoroacetic acid and 8 ml of anisole, and the mixture was subjected to reaction at room temperature for 1 hour. After completion of the reaction, the solvent was removed by distillation under reduced pressure. To the residue was added 40 ml of diethyl ether, and the crystals were collected by filtration to obtain 4.50 g (yield, 74.1%) of trifluoroacetic acid salt of 7-[2-(2-aminothiazol-4-yl)acetamido]-3-{[1-(4-ethyl-2,3-dioxo-1,2,3,4-tetrahydropyrazinyl)]methyl}-$\Delta^3$-cephem-4-carboxylic acid having a melting point of 109°-115° C. (dec.).

In a similar manner, the following compound was obtained: Trifluoroacetic acid salt of 7-[2-(2-aminothiazol-4-yl)acetamido]-3-{[1-(3,6-dioxo-1,2,3,6-tetrahydropyridazinyl)]methyl}-$\Delta^3$-cephem-4-carboxylic acid, m.p.: 200° C. or more.

Physical properties (IR, NMR values) of this compound were identical with those in Example 13-(2).

PREPARATION EXAMPLE 1

An aqueous sodium salt solution of 7-[2-(2-aminothiazol-4-yl)-2-(syn)-methoxyiminoacetamido]-3-{[1-

(2,3-dioxo-1,2,3,4-tetrahydropyrazinyl]methyl}-$\Delta^3$-cephem-4-carboxylic acid was treated in a conventional manner to obtain a freeze-dried and sterilized sodium salt. One gram (potency) of the sodium salt was dissolved in 20 ml of physiological saline solution to obtain an injection.

PREPARATION EXAMPLE 2

One gram (potency) of the freeze-dried product obtained in Preparation Example 1 was dissolved in 4 ml of 0.5% (W/V) aqueous lidocaine hydrochloride solution to obtain a dilutable injection.

PREPARATION EXAMPLE 3

One gram (potency) of the freeze-dried product obtained in Preparation Example 1 was dissolved in 20 ml of 5% glucose solution to obtain an injection.

Moreover, the other compounds of the formula [I] can also be formed into the corresponding freeze-dried products (sodium salts) or injections by processing them in the same manner as in Preparation Examples 1 to 3.

What is claimed is:

1. A 7-amino-3-substituted methyl-$\Delta^3$-cephem-4-carboxylic acid derivative represented by the following formula or a salt thereof:

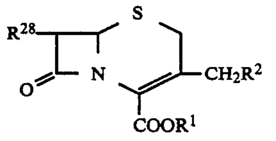

wherein $R^1$ represents a hydrogen atom or a carboxyl-protecting group; $R^2$ represents a group of the formula:

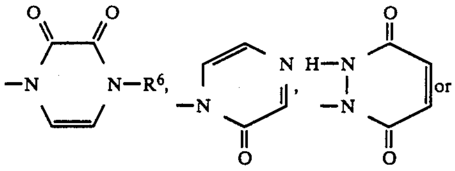

or

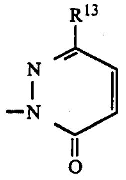

in which $R^6$ represents a hydrogen atom, a $C_{1-5}$ alkyl group or a di-$C_{1-5}$ alkylamino group; $R^{13}$ represents a $C_{1-5}$ alkyl group; and $R^{28}$ represents an amino group.

2. A 7-amino-3-substituted methyl-$\Delta^3$-cephem-4-carboxylic acid derivative or a salt thereof according to claim 1, wherein $R^2$ is a group of the formula,

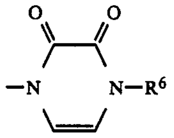

in which $R^6$ has the same meaning as defined in claim 1.

3. A 7-amino-3-substituted methyl-$\Delta^3$-cephem-4-carboxylic acid derivative or a salt thereof according to claim 2, wherein $R^6$ is a hydrogen atom or a $C_{1-5}$ alkyl group.

4. 7-amino-3-{[1-(2,3-dioxo-1,2,3,4-tetrahydropyrazinyl)]methyl}-$\Delta^3$-cephem-4-carboxylic acid, an ester thereof or a salt thereof.

5. 7-amino-3-{[1-(4-methyl-2,3-dioxo-1,2,3,4-tetrahydropyrazinyl)]methyl}-$\Delta^3$-cephem-4-carboxylic acid, an ester thereof or a salt thereof.

6. 7-amino-3-{[1-(4-ethyl-2,3-dioxo-1,2,3,4-tetrahydropyrazinyl)]methyl}-$\Delta^3$-cephem-4-carboxylic acid, an ester thereof or a salt thereof.

* * * * *